US011707536B2

(12) United States Patent
Rottensteiner et al.

(10) Patent No.: US 11,707,536 B2
(45) Date of Patent: Jul. 25, 2023

(54) VIRAL VECTORS ENCODING RECOMBINANT FVIII VARIANTS WITH INCREASED EXPRESSION FOR GENE THERAPY OF HEMOPHILIA A

(71) Applicant: Takeda Pharmaceutical Company Limited, Osaka (JP)

(72) Inventors: Hanspeter Rottensteiner, Vienna (AT); Friedrich Scheiflinger, Vienna (AT)

(73) Assignee: Takeda Pharmaceutical Company Limited, Osaka (JP)

( * ) Notice: Subject to any disclaimer, the term of this patent is extended or adjusted under 35 U.S.C. 154(b) by 273 days.

(21) Appl. No.: 16/743,850

(22) Filed: Jan. 15, 2020

(65) Prior Publication Data

US 2020/0289672 A1 Sep. 17, 2020

Related U.S. Application Data

(60) Provisional application No. 62/793,058, filed on Jan. 16, 2019.

(51) Int. Cl.

| | |
|---|---|
| ***A61K 48/00*** | (2006.01) |
| ***A61K 31/711*** | (2006.01) |
| ***C07K 14/755*** | (2006.01) |
| ***C12N 15/86*** | (2006.01) |

(52) U.S. Cl.

CPC ........ *A61K 48/0058* (2013.01); *A61K 31/711* (2013.01); *C07K 14/755* (2013.01); *C12N 15/86* (2013.01); *C12N 2750/14141* (2013.01)

(58) Field of Classification Search

CPC ......... C12N 15/86; A61K 48/00; A61K 38/37

See application file for complete search history.

(56) References Cited

U.S. PATENT DOCUMENTS

| | | | |
|---|---|---|---|
| 4,797,368 | A | 1/1989 | Carter et al. |
| 4,868,112 | A | 9/1989 | Toole, Jr. |
| 5,112,950 | A | 5/1992 | Meulien et al. |
| 5,139,941 | A | 8/1992 | Muzyczka et al. |
| 5,171,844 | A | 12/1992 | Van Ooyen et al. |
| 5,543,502 | A | 8/1996 | Nordfang et al. |
| 5,595,886 | A | 1/1997 | Chapman et al. |
| 5,610,278 | A | 3/1997 | Nordfang et al. |
| 5,789,203 | A | 4/1998 | Chapman et al. |
| 5,935,935 | A | 8/1999 | Connelly et al. |
| 5,972,885 | A | 10/1999 | Spira et al. |
| 5,994,136 | A | 11/1999 | Naldini et al. |
| 6,013,516 | A | 1/2000 | Verma et al. |
| 6,048,720 | A | 4/2000 | Dalborg et al. |
| 6,060,447 | A | 5/2000 | Chapman et al. |
| 6,114,148 | A | 9/2000 | Seed et al. |
| 6,200,560 | B1 | 3/2001 | Couto et al. |
| 6,228,620 | B1 | 5/2001 | Chapman et al. |
| 6,316,226 | B1 | 11/2001 | Van Ooyen et al. |
| 6,346,513 | B1 | 2/2002 | Van Ooyen et al. |
| 6,458,563 | B1 | 10/2002 | Lollar |
| 6,649,375 | B2 | 11/2003 | Connelly et al. |
| 6,818,439 | B1 | 11/2004 | Jolly et al. |
| 6,924,365 | B1 | 8/2005 | Miller et al. |
| 7,041,635 | B2 | 5/2006 | Kim et al. |
| 7,635,763 | B2 | 12/2009 | Lollar |
| 7,943,374 | B2 | 5/2011 | Hildinger |
| 7,973,374 | B2 | 7/2011 | Jeong |
| 8,188,246 | B2 | 5/2012 | Lollar |
| 8,519,111 | B2 | 8/2013 | Lollar |
| 8,986,991 | B2 | 3/2015 | Denning et al. |
| 9,393,323 | B2 | 7/2016 | Nathwani et al. |
| 9,447,168 | B2 | 9/2016 | Nathwani et al. |
| 9,504,762 | B2 | 11/2016 | Colosi et al. |
| 10,421,798 | B2 | 9/2019 | Schellenberger et al. |
| 2003/0228282 | A1 | 12/2003 | Gao et al. |
| 2006/0099685 | A1 | 5/2006 | Yallop et al. |
| 2011/0184049 | A1 | 7/2011 | Chuah et al. |
| 2012/0178691 | A1 | 7/2012 | Schellenberger et al. |
| 2013/0017997 | A1 | 1/2013 | Schellenberger et al. |
| 2013/0024960 | A1 | 1/2013 | Nathwani et al. |
| 2013/0202596 | A1 | 8/2013 | Salas et al. |
| 2014/0370035 | A1 | 12/2014 | Jiang et al. |
| 2015/0023959 | A1 | 1/2015 | Chhabra et al. |
| 2015/0038421 | A1 | 2/2015 | Schellenberger et al. |
| 2015/0071883 | A1 | 3/2015 | Colosi et al. |
| 2015/0111955 | A1 | 4/2015 | High et al. |
| 2015/0158929 | A1 | 6/2015 | Schellenberger et al. |
| 2015/0158930 | A1 | 6/2015 | Nathwani et al. |
| 2015/0283267 | A1 | 10/2015 | Vandendriessche et al. |

(Continued)

FOREIGN PATENT DOCUMENTS

| | | | |
|---|---|---|---|
| WO | WO 2007/149852 | A2 | 12/2007 |
| WO | WO 2008/077616 | A1 | 7/2008 |

(Continued)

OTHER PUBLICATIONS

Altschul et al. (1990) "Basic local alignment search tool," Journal of molecular biology. 215(3):403-410.

Altschul et al. (1996) "Local alignment statistics," Methods in enzymology. 266(2):460-480.

Altschul et al. (1997) "Gapped BLAST and PSI-BLAST: a new generation of protein database search programs," Nucleic acids research. 25(17):3389-3402.

Aponte-Ubillus et al. (2018) "Molecular design for recombinant adeno-associated virus (rAAV) vector production," Applied microbiology and biotechnology. 102(3):1045-1054.

(Continued)

*Primary Examiner* — Dana H Shin

(74) *Attorney, Agent, or Firm* — Morgan, Lewis & Bockius LLP

(57) ABSTRACT

The present disclosure provides, among other aspects, codon-altered polynucleotides encoding Factor VIII variants for expression in mammalian cells. In some embodiments, the disclosure also provides mammalian gene therapy vectors and methods for treating hemophilia A.

17 Claims, 28 Drawing Sheets

Specification includes a Sequence Listing.

(56) References Cited

U.S. PATENT DOCUMENTS

2015/0361158 A1 12/2015 Tan et al.
2016/0030524 A1 2/2016 Wang et al.
2016/0229904 A1 8/2016 Xiao et al.
2016/0251409 A1 9/2016 Oestergaard et al.
2017/0049859 A1 2/2017 Nathwani et al.
2017/0095538 A1 4/2017 Colosi et al.
2017/0233455 A1 8/2017 Falkner et al.
2017/0233456 A1 8/2017 Sabatino et al.
2018/0071406 A1 3/2018 Chuah et al.
2019/0194295 A1 6/2019 Falkner et al.
2019/0240350 A1 8/2019 Vandendriessche et al.
2021/0403948 A1* 12/2021 Chuah .................. C07K 14/745

FOREIGN PATENT DOCUMENTS

WO WO 2013/016454 A1 1/2013
WO WO 2013151666 A2 10/2013
WO WO 2015/038625 A1 3/2015
WO WO 2017/083762 A1 5/2017

OTHER PUBLICATIONS

Asokan et al. (2012) "The AAV Vector Toolkit: Poised at the Clinical Crossroads," Molecular Therapy. 20(4):699-708.
Bancel et al. (2013) "Human diseases associated protein encoding optimized ORF," EBII Accession No. GSN:BAW43417, 1 page.
Blomer et al. (1997) "Highly Efficient and Sustained Gene Transfer in Adult Neurons with a Lentivirus Vector," Journal of Virology. 71(9):6641-6649.
Bolivar (1979) "Molecular cloning vectors derived from the CoLEI type plasmid pMBI," Life sciences. 25(10):807-817.
Cao et al. (2014)"Abstract #460: A Novel Factor VIII Variant with Enhanced Secretion for Gene Therapy of Hemophilia A," Mol. Ther. 22, Supplement 1, S176, 1 page.
Chuah et al. (2012) "Platelet-directed gene therapy overcomes inhibitory antibodies to factor VIII," Journal of Thrombosis and Haemostasis. 10(8):1566-1569.
Chuah et al. (2012) "Recent progress in gene therapy for hemophilia," Human gene therapy. 23(6):557-565.
Chuah et al. (2013) "Gene therapy for hemophilia," Journal of thrombosis and haemostasis. 11:99-110.
Chuah et al. (2014) "Liver-specific transcriptional modules identified by genome-wide in silico analysis enable efficient gene therapy in mice and non-human primates," Molecular Therapy. 22(9):1605-1613.
Cotten et al. (1992) "High-efficiency receptor-mediated delivery of small and large (48 kilobase gene constructs using the endosome-disruption activity of defective or chemically inactivated adenovirus particles," Proc. Natl. Acad. Sci. 89:6094-6098.
Curiel (1994) "High-efficiency gene transfer employing adenovirus-polylysine-DNA complexes," Natural Immunity. 13:141-164.
Daya et al. (2008) "Gene Therapy Using Adeno-Associated Virus Vectors," Clinical Microbiology Reviews. 21(4):583-593.
Desmet et al. (2005) "Anchor profiles of HLA-specific peptides: analysis by a novel affinity scoring method and experimental validation," Proteins: Structure, Function, and Bioinformatics. 58(1):53-69.
Donath et al. (1995) "Characterization of des-(741-1668)-factor VIII, a single-chain factor VIII variant with a fusion site susceptible to proteolysis by thrombin and factor Xa," Biochem Journal. 312:49-55.
Fagone et al. (2012) "Systemic errors in quantitative polymerase chain reaction titration of self-complementary adeno-associated viral vectors and improved alternative methods," Human Gene Therapy, Part B: Methods. 23(1):1-7.
Fath et al. (2011) "Multiparameter RNA and Codon Optimization: A Standardized Tool to Assess and Enhance Autologous Mammalian Gene Expression," PLoS ONE. 6(3):1-14.
Feng et al. (1987) "Progressive sequence alignment as a prerequisitetto correct phylogenetic trees," Journal of molecular evolution. 25(4):351-360.
Gardinier-Garden et al. (1987) "CpG Islands in vertebrate genomes," Journal of Molecular Biology. 196(2):261-282.
Graw et al. (2005) "Haemophilia A: from mutation analysis to new therapies," Nature Reviews Genetics. 6(6):488-501.
Gray et al. (2011) "Optimizing Promoters for Recombinant Adeno-Associated Virus-Mediated Gene Expression in the Peripheral and Central Nervous System Using Self-Complementary Vectors," Human Gene Therapy. 22:1143-1153.
Grieger et al. (2015) "Production of Recombinant Adeno-associated Virus Vectors Using Suspension HEK293 Cells and Continuous Harvest of Vector From the Culture Media for GMP FIX and FLT1 Clinical Vector," Molecular Therapy. 24(2):287-297.
Grote et al. (2005) "JCat: a novel tool to adapt codon usage of a target gene to its potential expression host," Nucleic Acid Research. 33:W526-W531.
Gupta et al. (2004) "Prediction of N-glycosylation sites in human proteins," DTU Health Tech—Technical University of Denmark. 1:203-206.
Haas et al. (1996) "Codon usage limitation in the expression of HIV-1 envelope glycoprotein," Current Biology. 6(3):315-324.
Higgins et al. (1989) "Fast and sensitive multiple sequence alignments on a microcomputer," Bioinformatics. 5(2):151-153.
High (2012) "The gene therapy journey for hemophilia: are we there yet?" Blood, The Journal of the American Society of Hematology. 120(23):4482-4487.
Hsieh et al. (2009) "Transthyretin-driven oncolytic adenovirus suppresses tumor growth in orthotopic and ascites models of hepatocellular carcinoma," Cancer science. 100(3):537-545.
International Search Report for International Application No. PCT/US2016/061684, dated Feb. 15, 2017, 13 pages.
International Search Report for International Application No. PCT/US2016/061688, dated Feb. 6, 2017, 13 pages.
Karlin et al. (1993) "Applications and statistics for multiple high-scoring segments in molecular sequences," Proceedings of the National Academy of Sciences. 90(12):5873-5877.
Kelleher et al. (1994) "Long-term episomal gene delivery in human lymphoid cells using human and avian adenoviral-assisted transfection," Biotechniques. 17:1110-1117.
Kotin (2011) "Large-scale recombinant adeno-associated virus production," Human molecular genetics. 20(R1):R2-R6.
Kriegler (1990) "Gene Transfer and Expression, A Laboratory Manual," Stockton Press, 10 pages.
Krinner et al. (2014) "CpG domains downstream of TSSs promote high levels of gene expression," Nucleic Acid Research. 42(6):3551-3564.
Kudla et al. (2006) "High Guanine and Cytosine Content Increases mRNA Levels in Mammalian Cells," PLoS Biology. 4(6):0933-0942.
Laupeze et al. (1999) "Differential expression of major histocompatibility complex class Ia, Ib and II molecules on monocytes and monocyte-derived dendritic and macrophagic cells," Human immunology. 60(7):591-597.
Lenting et al. (1998) "The life cycle of coagulation factor VIII in view of its structure and function," Blood, The Journal of the American Society of Hematology. 92(11):3983-3996.
Mann et al. (1983) "Construction of a retrovirus packaging mutant and its use to produce helper-free defective retrovirus," Cell. 33(1):153-159.
Manno et al. (2006) "Successful transduction of liver in hemophilia by AAV-Factor IX and limitations imposed by the host immune response," Nature Medicine. 12:342-347.
Mannucci (2003) "Hemophilia: treatment options in the twenty-first century," Journal of Thrombosis and Haemostasis. 1(7):1349-1355.
Mátrai et al. (2010) "Preclinical and clinical progress in hemophilia gene therapy," Current opinion in hematology. 17(5):387-392.
Mátrai et al. (2010) "Recent advances in lentiviral vector development and applications," Molecular therapy. 18(3):477-490.

(56) References Cited

OTHER PUBLICATIONS

McIntosh et al. (2013) "Therapeutic levels of FVIII following a single peripheral vein administration of rAAV vector encoding a novel human factor VIII variant," Blood Journal. 121(17):3335-3344.
Miao et al. (2004) "Bioengineering of coagulation factor VIII for improved secretion," Blood Journal. 103(9):3412-3419.
Mirsafian et al. (2014) "A Comparative Analysis of Synonymous Codon Usage Bias Pattern in Human Albumin Superfamily," Scientific World Journal. Article 639682, 7 pages.
Murray (1991) "Gene Transfer and Expression Protocols," Methods in Molecular Biology, 7 pages.
Muzyczka (1992) "Use of adeno-associated virus as a general transduction vector for mammalian cells," Current Topics Microbiology and Immunology. 158:97-129.
Nair et al. (2014) "Computationally designed liver-specific transcriptional modules and hyperactive factor IX improve hepatic gene therapy," Blood, The Journal of the American Society of Hematology. 123(20):3195-3199.
Naldini et al. (1996) "In Vivo Gene Delivery and Stable Transduction of Nondividing Cells by a Lentiviral Vector," Science. 272(5259):263-267.
Needleman et al. (1970) "A general method applicable to the search for similarities in the amino acid sequence of two proteins," Journal of molecular biology. 48(3):443-453.
Nicolas et al. (1988) "Retroviral vectors," Vectors. A survey of molecular cloning vectors and their uses. 1:494-513.
Oh et al. (2001) "Purification of Recombinant Human B-Domain-Deleted Factor VIII Using Anti-Factor VIII Monoclonal Antibody Selected by the Surface Plasmon Resonance Biosensor," Biotechnol. Prog. 17:1119-1127.
Pearson et al. (1988) "Improved tools for biological sequence comparison," Proceedings of the National Academy of Sciences. 85(8):2444-2448.
Penaud-Budloo et al. (2018) "Pharmacology of recombinant adeno-associated virus production," Molecular Therapy—Methods & Clinical Development. 8:166-180.
Radcliffe et al. (2008) "Analysis of factor VIII mediated suppression of lentiviral vector titres," Gene Therapy. 15:289-297.
Reipert et al. (2010) "Animal models of inhibitors," Haemophilia. 16:47-53.
Saenko et al. (1999) "Role of activation of the coagulation factor VIII in interaction with vWf, phospholipid, and functioning within the factor Xase complex," Trends in cardiovascular medicine. 9(7):185-192.
Sandberg et al. (2001) "Structural and functional characteristics of the B-domain-deleted recombinant factor VIII, r-VIII SQ," Journal of Thrombosis and Haemostasis. 85:93-100.
Selvaraj et al. (2012) "Bioengineering of coagulation factor VIII for efficient expression through elimination of a dispensable disulfide loop," Journal of Thrombosis and Haemostasis. 10:107-115.
Smith et al. (1981) "Comparison of biosequences," Advances in applied mathematics. 2(4):482-489.
Steentoft et al. (2013) "Precision mapping of the human O-GaINAc glycoproteome through SimpleCell technology," The EMBO journal. 32(10):1478-1488.
Sutcliffe (1978) "Nucleotide sequence of the ampicillin resistance gene of *Escherichia coli* plasmid pBR322," Proceedings of the National Academy of Sciences. 75(8):3737-3741.
Swaaroop et al. (1997) "Mutagenesis of a Potential Immunoglobulin-binding Protein-binding Site Enhances Secretion of Coagulation Factor VIII," Journal of Biological Chemistry. 272(39):24121-24124.
Tats et al. (2008) "Preferred and avoided codon pairs in three domains of life," BMC Genomics. 9(463):1-15.
Temin (1986) "Retrovirus Vectors for Gene Transfer: Efficient Integration into and Expression of Exogenous DNA in Vertebrate Cell Genomes," Gene Transfer. 1:149-188.
Thim et al. (2010) "Purification and characterization of a new recombinant factor VIII (N8)," Haemophilia. 16(2):349-359.
Toschi et al. (2010) "OBI-1, porcine recombinant Factor VIII for the potential treatment of patients with congenital hemophilia A and alloantibodies against human Factor VIII," Current Opinion in Molecular Therapy. 12(5):617-625.
Van Helden et al. (2011) "Maintenance and break of immune tolerance against human factor VIII in a new transgenic hemophilic mouse model," Blood, The Journal of the American Society of Hematology. 118(13):3698-3707.
Vandendriessche et al. (2012) "Clinical progress in gene therapy: sustained partial correction of the bleeding disorder in patients suffering from severe hemophilia B," Human gene therapy. 23(1):4-6.
Varfaj et al. (2007) "Residues Surrounding Arg336 and Arg562 Contribute to the Disparate Rates of Proteolysis of Factor Villa Catalyzed by Activated Protein C," Journal of Biological Chemistry. 282(28):20264-20272.
Verreck et al. (1996) "The generation of SDS-stable HLA DR dimers is independent of efficient peptide binding," International immunology. 8(3):397-404.
Wakabayashi et al. (2002) "Ca(2+) binding to both the heavy and light chains of factor VIII is required for cofactor activity," Biochemistry. 41:8485-8492.
Wakabayashi et al. (2004) "Residues 110-126 in the AI Domain of Factor VIII Contain a Ca2+ Binding Site Required for Cofactor Activity," Journal of Biochemistry. 279(13):12677-12684.
Wakabayashi et al. (2005) "A Glul 13AIa mutation within a factor VIII Ca2+ binding site enhances cofactor interactions in factor Xase," Biochemistry. 44:10298-10304.
Wakabayashi et al. (2008) "Generation of enhanced stability factor VIII variants by replacement of charged residues at the A2 domain interface," Blood. 12(7):2761-2769.
Wakabayashi et al. (2009) "Combining mutations of charged residues at the A2 domain interface enhances factor VIII stability over single point mutations," Journal of Thrombosis and Haemostasis. 7:438-444.
Wakabayashi et al. (2011) "Increasing Hydrophobicity or Disulfide Bridging at the Factor VIII AI and C2 Domain Interface Enhances Procofactor Stability," Journal of Biological Chemistry. 286(29):25748-25755.
Wakabayashi et al. (2012) "Enhancing factor VIII and Villa stability by combining mutations at the A2 domain interface and AI-C2 domain interface," Journal of Thrombosis and Haemostasis. 10:492-495.
Ward et al. (2011) "Codon optimization of human factor VIII cDNAs leads to high-level expression," Blood Journal. 117(3):798-807.
Yan et al. (1990) "Distinct positive and negative elements control the limited hepatocyte and choroid plexus expression of transthyretin in transgenic mice," The EMBO journal. 9(3):869-878.
Zhang et al. (2009) "Factor VIII inhibitors: risk factors and methods for prevention and immune modulation," Clinical reviews in allergy & immunology. 37(2):114-124.
Zollner et al. (2014) "Non-clinical pharmacokinetics and pharmacodynamics of rVIII-SingleChain, a novel recombinant single-chain factor VIII," Thrombosis Research. 134:125-131.
Zufferey et al. (1997) "Multiply attenuated lentiviral vector achieves efficient gene delivery in vivo," Nature Biotechnology. 15:871-875.
Database GenBank (Jun. 7, 1993) "coagulation factor VIII [Mus musculus domesticus]," NCBI Reference Sequence: AAA37385.1, 2 pages.
Database GenBank (Apr. 6, 2016) "coagulation factor VIII [*Homo sapiens*]," NCBI Reference Sequence: AAA52420.1, 3 pages.
Database GenBank (Nov. 8, 1994) "factor VIII [*Homo sapiens*]," NCBI Reference Sequence: AAA52484.1, 3 pages.
Database GenBank (Nov. 8, 1994) "preprocoagulation factor VIII:C [*Homo sapiens*]," NCBI Reference Sequence: AAA52485.1, 4 pages.
Database GenBank (Dec. 31, 1994) "coagulation factor VIII associated protein B [*Homo sapiens*]," NCBI Reference Sequence: AAA58466.1, 1 page.
Database GenBank (Jun. 15, 1997) "clotting factor VIII, partial [*Homo sapiens*]," NCBI Reference Sequence: AAB61261.1, 1 page.

(56) References Cited

OTHER PUBLICATIONS

Database GenBank (Aug. 4, 2008) "Coagulation factor VIII, procoagulant component [*Homo sapiens*]," NCBI Reference Sequence: AAH22513.1, 2 pages.
Database GenBank (Aug. 4, 2008) "Coagulation factor VIII, procoagulant component [*Homo sapiens*]," NCBI Reference Sequence: AAH64380.1, 2 pages.
Database GenBank (Aug. 4, 2008) "Coagulation factor VIII, procoagulant component [Homo sapiens]," NCBI Reference Sequence: AAH98389.1, 2 pages.
Database GenBank (Aug. 4, 2008) "Coagulation factor VIII, procoagulant component [*Homo sapiens*]," NCBI Reference Sequence: AAI11968.1, 2 pages.
Database GenBank (Aug. 4, 2008) "Coagulation factor VIII, procoagulant component [*Homo sapiens*]," NCBI Reference Sequence: AAI11970.1, 2 pages.
Database GenBank (Aug. 13, 2003) "factor VIII [Rattus norvegicus]," NCBI Reference Sequence: AAQ21580.1, 2 pages.
Database GenBank (Dec. 11, 2004) "coagulation factor VIII, procoagulant component (hemophilia A) [*Homo sapiens*]," NCBI Reference Sequence: AAV85964.1, 3 pages.
Database GenBank (Jan. 9, 2008) "unnamed protein product [*Homo sapiens*]," NCBI Reference Sequence: BAF82636.1, 2 pages.
Database GenBank (May 24, 2008) "unnamed protein product [*Homo sapiens*]," NCBI Reference Sequence: BAG36452.1, 2 pages.
Database GenBank (Jan. 29, 2011) "HS14F12r HS *Hordeum vulgare* subsp. *vulgare* cDNA clone HS14F12 5-PRIME, mRNA sequence," NCBI Reference Sequence: CA003404.1, 1 page.
Database GenBank (Oct. 7, 2008) "unnamed protein product [*Homo sapiens*]," NCBI Reference Sequence: CAA25619.1, 4 pages.
Database GenBank (Jan. 15, 2009) "coagulation factor VIII, procoagulant component [*Homo sapiens*]," NCBI Reference Sequence: CAI41660.1, 3 pages.
Database GenBank (Jan. 15, 2009) "coagulation factor VIII, procoagulant component [*Homo sapiens*]," NCBI Reference Sequence: CAI41666.1, 3 pages.
Database GenBank (Jan. 15, 2009) "coagulation factor VIII, procoagulant component [*Homo sapiens*]," NCBI Reference Sequence: CAI41672.1, 3 pages.
Database GenBank (Jan. 15, 2009) "coagulation factor VIII, procoagulant component [*Homo sapiens*]," NCBI Reference Sequence: CAI43241.1, 3 pages.
Database GenBank (May 3, 2008) "coagulation factor VIII [Mus musculus]," NCBI Reference Sequence: CAM15581.1, 2 pages.
Database GenBank (Jan. 15, 2009) "coagulation factor VIII [Mus musculus]," NCBI Reference Sequence: CAM26492.1, 3 pages.
Database GenBank (Mar. 23, 2015) "coagulation factor VIII, procoagulant component (hemophilia A), isoform CRA_a [*Homo sapiens*]," NCBI Reference Sequence: EAW72645.1, 2 pages.
Database GenBank (Jul. 26, 2016) "coagulation factor VIII [Mus musculus]," NCBI Reference Sequence: EDL29229.1, 3 pages.
Database GenBank (Nov. 8, 1994) "Human coagulation factor VIII:C mRNA, complete cds," NCBI Reference Sequence: M14113.1, 4 pages.
Database GenBank (Apr. 23, 2019) "*Homo sapiens* serpin family A member 1 (SERPINA1), transcript variant 1, mRNA," NCBI Reference Sequence: NM_000295.4, 5 pages.
Database UniProt (May 3, 2011) "ull=Coagulation factor VIII {ECG:0000313|Ensembl:ENSSSCP00000013628}" NCBI Reference Sequence: F1RZ36, 2 pages.
Database UniProt (Jan. 9, 2013) "Full=Coagulation factor VIII {ECG:0000313|Ensembl:ENSSSCP00000031036}" NCBI Reference Sequence: F1RZ36, 1 page.
Database UniProt (Nov. 13, 2019) "RecName: Full=Coagulation factor VIII; AltName: Full=Antihemophilic factor; Short=AHF; AltName: Full=Procoagulant component; Contains: RecName: Full=Factor Villa heavy chain, 200 kDa isoform; Contains: RecName: Full=Factor Villa heavy chain, 92 kDa isoform; Co . . . ," NCBI Reference Sequence: P00451.1, 61 pages.
Database UniProt (Oct. 16, 2019) "RecName: Full=Coagulation factor IX; AltName: Full=Christmas factor; AltName: Full=Plasma thromboplastin component; Short=PTC; Contains: RecName: Full=Coagulation factor IXa light chain; Contains: RecName: Full=Coagulation factor IXa heavy chain; Flags: Precursor" NCBI Reference Sequence: P00740.2, 36 pages.
Tsuzuki et al: "The Journal of Biological Chemistry 0 1985 by The American Society of Biological Chemists Structure of the Human Prealbumin Gene*", Oct. 5, 1985 (Oct. 5, 1985), pp. 12224-12227, XP55685725, Retrieved from the Internet: URL:https://www.jbc.org/content/260/22/12224.full.pdf#page=l&view-FitH.

* cited by examiner

CS12-FL-NA atgcagattgagctgagcacctgcttcttcctgtgcctgctgaggttctgcttctctgccaccagga
gatactacctggggggctgtggagctttcttgggactacatgcagtctgacctggggggagctgcctgt
ggatgccaggttcccacccagagtgcccaaatccttcccattcaacacctctgtggtctacaagaag
accctctttgtggagttcactgaccacctgttcaacattgccaaacccaggccaccctggatgggac
tcctgggacccaccattcaggctgaggtgtatgacactgtggtcgtcaccctcaagaacatggcctc
ccaccctgtgagcctgcatgctgtgggggtcagctactggaagtcctctgaggggggctgagtatgat
gaccagacctcccagagggagaaggaggatgacaaagtgttccctgggaagagccacacctatgtgt
ggcaggtcctcaaggagaatggccccactgcctctgacccaccctgcctgacctactcctacctttc
tcatgtggacctggtcaaggacctcaactctggactgattggggccctgctggtgtgcagggagggc
tccctggccaaagagaagacccagaccctgcacaagttcattctcctgtttgctgtctttgatgagg
gcaagagctggcactctgaaaccaagaactccctgatgcaggacagggatgctgcctctgccagggc
ctggcccaagatgcacactgtgaatggctatgtgaacaggagcctgcctggactcattggctgccac
aggaaatctgtctactggcatgtgattggcatggggacaacccctgaggtgcactccattttcctgg
agggccacaccttcctggtcaggaaccacagacaggccagcctggagatcagccccatcaccttcct
cactgcccagaccctgctgatggacctcggacagttcctgctgttctgccacatcagctcccaccag
catgatggcatggaggcctatgtcaaggtggacagctgccctgaggagccacagctcaggatgaaga
acaatgaggaggctgaggactatgatgatgacctgactgactctgagatggatgtggtccgctttga
tgatgacaacagcccatccttcattcagatcaggtctgtggccaagaaacaccccaagacctgggtg
cactacattgctgctgaggaggaggactgggactatgccccactggtcctggcccctgatgacagga
gctacaagagccagtacctcaacaatggcccacagaggattggacgcaagtacaagaaagtcaggtt
catggcctacactgatgaaaccttcaagaccagggaggccattcagcatgagtctggcatcctgggc
ccactcctgtatggggaggtgggggacaccctgctcatcatcttcaagaaccaggcctccaggccct
acaacatctacccacatggcatcactgatgtcaggcccctgtacagccgcaggctgccaaaggggt
gaaacacctcaaggacttccccattctgcctggggagatcttcaagtacaagtggactgtcactgtg
gaggatggaccaaccaaatctgaccccaggtgcctcaccagatactactccagctttgtgaacatgg
agagggacctggcctctggcctgattggcccactgctcatctgctacaaggagtctgtggaccagag
gggaaaccagatcatgtctgacaagaggaatgtgattctgttctctgtctttgatgagaacaggagc
tggtacctgactgagaacattcagcgcttcctgcccaaccctgctggggtgcagctggaggaccctg
agttccaggccagcaacatcatgcactccatcaatggctatgtgtttgacagcctccagctttctgt
ctgcctgcatgaggtggcctactggtacattctttctattggggcccagactgacttcctttctgtc
ttcttctctggctacaccttcaaacacaagatggtgtatgaggacaccctgaccctcttcccattct
ctggggagactgtgttcatgagcatggagaaccctggcctgtggattctgggatgccacaactctga
cttccgcaacaggggcatgactgccctgctcaaagtctcctcctgtgacaagaacactggggactac
tatgaggacagctatgaggacatctctgcctacctgctcagcaagaacaatgccattgagcccagga
gcttcagccagaatgtgagcaataatgccaccaacccacctgtcctgaaacgccaccagagggagat
caccaggaccaccctccagtctgaccaggaggagattgactatgatgacaccatttctgtggagatg
aagaaagaggactttgacatctatgacgaggacgagaaccagagcccaaggagcttccagaagaaga
ccaggcaCtacttcattgctgctgtggagcgcctgtgggactatggcatgagctccagcccccatgt
cctcaggaacagggcccagtctggctctgtgccacagttcaagaaagtggtcttccaagagttcact (Continued)

Figure 1A gatggcagcttcacccagcccctgtacagaggggagctgaatgagcacctgggactcctgggcccat
acatcagggctgaggtggaggacaacatcatggtgaccttccgcaaccaggcctccaggccctacag
cttctacagctccctcatcagctatgaggaggaccagaggcaggggctgagccacgcaagaacttt
gtgaaacccaatgaaaccaagacctacttctggaaagtccagcaccacatggcccccaccaaggatg
agtttgactgcaaggcctgggcctacttctctgatgtggacctggagaaggatgtgcactctggcct
gattggccccactcctggtctgccacaccaacaccctgaaccctgcccatggaaggcaagtgactgtg
caggagtttgccctcttcttcaccatctttgatgaaaccaagagctggtacttcactgagaacatgg
agcgcaactgcagggccccatgcaacattcagatggaggaccccaccttcaaagagaactaccgctt
ccatgccatcaatggctacatcatggacaccctgcctgggcttgtcatggcccaggaccagaggatc
aggtggtacctgctttctatgggctccaatgagaacattcactccatccacttctctgggcatgtct
tcactgtgcgcaagaaggaggagtacaagatggccctgtacaacctctaccctggggtctttgagac
tgtggagatgctgccctccaaagctggcatctggagggtggagtgcctcattggggagcacctgcat
gctggcatgagcaccctgttcctggtctacagcaacaagtgccagacccccctgggaatggcctctg
gccacatcagggacttccagatcactgcctctggccagtatggccagtgggcccccaagctggccag
gctccactactctggatccatcaatgcctggagcaccaaggagccattcagctggatcaaagtggac
ctgctggcccccatgatcatccatggcatcaagacccagggggccaggcagaagttctccagcctgt
acatcagccagttcatcatcatgtacagcctggatggcaagaaatggcagacctacagaggcaactc
cactggaacactcatggtcttctttggcaatgtggacagctctggcatcaagcacaacatcttcaac
cccccaatcatcgccagatacatcaggctgcaccccacccactacagcatccgcagcaccctcagga
tggagctgatgggctgtgacctgaactcctgcagcatgcccctgggcatggagagcaaggccatttc
tgatgcccagatcactgcctccagctacttcaccaacatgtttgccacctggagcccaagcaaggcc
aggctgcacctccagggaaggagcaatgcctggaggccccaggtcaacaacccaaaggagtggctgc
aggtggacttccagaagaccatgaaggtcactggggtgaccacccaggggtcaagagcctgctcac
cagcatgtatgtgaaggagttcctgatcagctccagccaggatggccaccagtggaccctcttcttc
cagaatggcaaggtcaaggtgttccagggcaaccaggacagcttCacccctgtggtgaacagcctgg
acccccccctcctgaccagatacctgaggattcacccccagagctgggtccaccagattgccctgag
gatggaggtcctgggatgtgaggcccaggacctgtac (SEQ ID NO:1)

```
MQIELSTCFFLCLLRFCFSATRRYYLGAVELSWDYMQSDLGELPVDARFPPRVPKSFPFN
TSVVYKKTLFVEFTDHLFNIAKPRPPWMGLLGPTIQAEVYDTVVVTLKNMASHPVSLHAV
GVSYWKSSEGAEYDDQTSQREKEDDKVFPGKSHTYVWQVLKENGPTASDPPCLTYSYLSH
VDLVKDLNSGLIGALLVCREGSLAKEKTQTLHKFILLFAVFDEGKSWHSETKNSLMQDRD
AASARAWPKMHTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPEEPQLRMKNNE
EAEDYDDDLTDSEMDVVRFDDDNSPSFIQIRSVAKKHPKTWVHYIAAEEEDWDYAPLVLA
PDDRSYKSQYLNNGPQRIGRKYKKVRFMAYTDETFKTREAIQHESGILGPLLYGEVGDTL
LIIFKNQASRPYNIYPHGITDVRPLYSRRLPKGVKHLKDFPILPGEIFKYKWTVTVEDGP
TKSDPRCLTRYYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRG
MTALLKVSSCDKNTGDYYEDSYEDISAYLLSKNNAIEPRSFSQNVSNNATNPPVLKRHQR
EITRTTLQSDQEEIDYDDTISVEMKKEDFDIYDEDENQSPRSFQKKTRHYFIAAVERLWD
YGMSSSPHVLRNRAQSGSVPQFKKVVFQEFTDGSFTQPLYRGELNEHLGLLGPYIRAEVE
DNIMVTFRNQASRPYSFYSSLISYEEDQRQGAEPRKNFVKPNETKTYFWKVQHHMAPTKD
EFDCKAWAYFSDVDLEKDVHSGLIGPLLVCHTNTLNPAHGRQVTVQEFALFFTIFDETKS
WYFTENMERNCRAPCNIQMEDPTFKENYRFHAINGYIMDTLPGLVMAQDQRIRWYLLSMG
SNENIHSIHFSGHVFTVRKKEEYKMALYNLYPGVFETVEMLPSKAGIWRVECLIGEHLHA
GMSTLFLVYSNKCQTPLGMASGHIRDFQITASGQYGQWAPKLARLHYSGSINAWSTKEPF
SWIKVDLLAPMIIHGIKTQGARQKFSSLYISQFIIMYSLDGKKWQTYRGNSTGTLMVFFG
NVDSSGIKHNIFNPPIIARYIRLHPTHYSIRSTLRMELMGCDLNSCSMPLGMESKAISDA
QITASSYFTNMFATWSPSKARLHLQGRSNAWRPQVNNPKEWLQVDFQKTMKVTGVTTQGV
KSLLTSMYVKEFLISSSQDGHQWTLFFQNGKVKVFQGNQDSFTPVVNSLDPPLLTRYLRI
HPQSWVHQIALRMEVLGCEAQDLY (SEQ ID NO:2)
```

Figure 2

CS12-CRM8.2-Vr

```
ttggccactccctctctgcgcgctcgctcgctcactgaggccgggcgaccaaaggtcgcccgacgcc
cgggctttgcccgggcggcctcagtgagcgagcgagcgcgcagagagggagtggccaactccatcac
taggggttcctggggaggctgctggtgaatattaaccaaggtcaccccagttatcggaggagcaaa
caggggctaagtccaccggggaggctgctggtgaatattaaccaaggtcaccccagttatcggagg
agcaaacaggggctaagtccacaaatgacctattaagaatatttcatagaacgaatgttccgatgct
ctaatctctctagacaaggttcatatttgtatgggttacttattctctctttgttgactaagtcaat
aatcagaatcagcaggtttgcagtcagattggcagggataagcagcctagctcaggagaagtgagta
taaaagccccaggctgggagcagccatcacagaagtccactcattcttggcaggccaccatgcagat
tgagctgagcacctgcttcttcctgtgcctgctgaggttctgcttctctgccaccaggagatactac
ctgggggctgtggagctttcttgggactacatgcagtctgacctgggggagctgcctgtggatgcca
ggttcccacccagagtgcccaaatccttcccattcaacacctctgtggtctacaagaagaccctctt
tgtggagttcactgaccacctgttcaacattgccaaacccaggccaccctggatgggactcctggga
cccaccattcaggctgaggtgtatgacactgtggtcgtcaccctcaagaacatggcctcccaccctg
tgagcctgcatgctgtgggggtcagctactggaagtcctctgagggggctgagtatgatgaccagac
ctcccagagggagaaggaggatgacaaagtgttccctgggaagagccacacctatgtgtggcaggtc
ctcaaggagaatggccccactgcctctgacccaccctgcctgacctactcctacctttctcatgtgg
acctggtcaaggacctcaactctggactgattggggccctgctggtgtgcagggagggctccctggc
caaagagaagacccagaccctgcacaagttcattctcctgtttgctgtctttgatgagggcaagagc
tggcactctgaaaccaagaactccctgatgcaggacagggatgctgcctctgccagggcctggccca
agatgcacactgtgaatggctatgtgaacaggagcctgcctggactcattggctgccacaggaaatc
tgtctactggcatgtgattggcatggggacaacccctgaggtgcactccattttcctggagggccac
accttcctggtcaggaaccacagacaggccagcctggagatcagccccatcaccttcctcactgccc
agaccctgctgatggacctcggacagttcctgctgttctgccacatcagctcccaccagcatgatgg
catggaggcctatgtcaaggtggacagctgccctgaggagccacagctcaggatgaagaacaatgag
gaggctgaggactatgatgatgacctgactgactctgagatggatgtggtccgctttgatgatgaca
acagcccatccttcattcagatcaggtctgtggccaagaaacaccccaagacctgggtgcactacat
tgctgctgaggaggaggactgggactatgccccactggtcctggcccctgatgacaggagctacaag
agccagtacctcaacaatggcccacagaggattggacgcaagtacaagaaagtcaggttcatggcct
acactgatgaaaccttcaagaccagggaggccattcagcatgagtctggcatcctgggcccactcct
gtatggggaggtgggggacaccctgctcatcatcttcaagaaccaggcctccaggccctacaacatc
tacccacatggcatcactgatgtcaggcccctgtacagccgcaggctgccaaaggggtgaaacacc
tcaaggacttccccattctgcctggggagatcttcaagtacaagtggactgtcactgtggaggatgg
accaaccaaatctgaccccaggtgcctcaccagatactactccagctttgtgaacatggagagggac
ctggcctctggcctgattggcccactgctcatctgctacaaggagtctgtggaccagaggggaaacc
agatcatgtctgacaagaggaatgtgattctgttctctgtctttgatgagaacaggagctggtacct
gactgagaacattcagcgcttcctgcccaaccctgctggggtgcagctggaggaccctgagttccag
gccagcaacatcatgcactccatcaatggctatgtgtttgacagcctccagctttctgtctgcctgc
atgaggtggcctactggtacattctttctattggggcccagactgacttcctttctgtcttcttctc
```

(Continued)

Figure 3A tggctacaccttcaaacacaagatggtgtatgaggacaccctgaccctcttcccattctctggggag
actgtgttcatgagcatggagaaccctggcctgtggattctgggatgccacaactctgacttccgca
acaggggcatgactgccctgctcaaagtctcctcctgtgacaagaacactggggactactatgagga
cagctatgaggacatctctgcctacctgctcagcaagaacaatgccattgagcccaggagcttcagc
cagaatgtgagcaataatgccaccaacccacctgtcctgaaacgccaccagagggagatcaccagga
ccaccctccagtctgaccaggaggagattgactatgatgacaccatttctgtggagatgaagaaaga
ggactttgacatctatgacgaggacgagaaccagagcccaaggagcttccagaagaagaccaggcac
tacttcattgctgctgtggagcgcctgtgggactatggcatgagctccagccccatgtcctcagga
acagggcccagtctggctctgtgccacagttcaagaaagtggtcttccaagagttcactgatggcag
cttcacccagcccctgtacagaggggagctgaatgagcacctgggactcctgggcccatacatcagg
gctgaggtggaggacaacatcatggtgaccttccgcaaccaggcctccaggccctacagcttctaca
gctccctcatcagctatgaggaggaccagaggcaggggctgagccacgcaagaactttgtgaaacc
caatgaaaccaagacctacttctggaaagtccagcaccacatggcccccaccaaggatgagtttgac
tgcaaggcctgggcctacttctctgatgtggacctggagaaggatgtgcactctggcctgattggcc
cactcctggtctgccacaccaacaccctgaaccctgcccatggaaggcaagtgactgtgcaggagtt
tgccctcttcttcaccatctttgatgaaaccaagagctggtacttcactgagaacatggagcgcaac
tgcagggccccatgcaacattcagatggaggaccccaccttcaaagagaactaccgcttccatgcca
tcaatggctacatcatggacaccctgcctgggcttgtcatggcccaggaccagaggatcaggtggta
cctgctttctatgggctccaatgagaacattcactccatccacttctctgggcatgtcttcactgtg
cgcaagaaggaggagtacaagatggccctgtacaacctctaccctggggtctttgagactgtggaga
tgctgccctccaaagctggcatctggagggtggagtgcctcattggggagcacctgcatgctggcat
gagcaccctgttcctggtctacagcaacaagtgccagacccccctgggaatggcctctggccacatc
agggacttccagatcactgcctctggccagtatggccagtgggcccccaagctggccaggctccact
actctggatccatcaatgcctggagcaccaaggagcccttcagctggatcaaagtggacctgctggc
cccatgatcatccatggcatcaagacccaggggccaggcagaagttctccagcctgtacatcagc
cagttcatcatcatgtacagcctggatggcaagaaatggcagacctacagaggcaactccactggaa
cactcatggtcttctttggcaatgtggacagctctggcatcaagcacaacatcttcaacccccccaat
catcgccagatacatcaggctgcaccccacccactacagcatccgcagcaccctcaggatggagctg
atgggctgtgacctgaactcctgcagcatgcccctgggcatggagagcaaggccatttctgatgccc
agatcactgcctccagctacttcaccaacatgtttgccacctggagcccaagcaaggccaggctgca
cctccagggaaggagcaatgcctggaggccccaggtcaacaacccaaaggagtggctgcaggtggac
ttccagaagaccatgaaggtcactggggtgaccacccaggggggtcaagagcctgctcaccagcatgt
atgtgaaggagttcctgatcagctccagccaggatggccaccagtggaccctcttcttccagaatgg
caaggtcaaggtgttccagggcaaccaggacagcttcacccctgtggtgaacagcctggacccccc
ctcctgaccagatacctgaggattcacccccagagctgggtccaccagattgccctgaggatggagg
tcctgggatgtgaggcccaggacctgtactgatgaaataaaagatctttattttcattagatctgtg
tgttggtttttgtgtgaggaacccctagtgatggAgttggccactccctctctgcgcgctcgctcg
ctcactgaggccgggcgaccaaaggtcgcccgacgcccgggctttgcccgggcggcctcagtgagcg
agcgagcgcgcagagagggagtggccaa (SEQ ID NO:3)

Figure 3B

5'-ITR ttggccactccctctctgcgcgctcgctcgctcactgaggccgggcgaccaaaggtcgcccgacgcc
cgggctttgcccgggcggcctcagtgagcgagcgagcgcgcagagagggagtggccaactccatcac
taggggttcct (SEQ ID NO:4)

CRM8 ggggaggctgctggtgaatattaaccaaggtcaccccagttatcggaggagcaaacaggggctaag
tccac (SEQ ID NO:5)

hTTR-Pro aaatgacctattaagaatatttcatagaacgaatgttccgatgctctaatctctctagacaaggttc
atatttgtatgggttacttattctctctttgttgactaagtcaataatcagaatcagcaggtttgca
gtcagattggcagggataagcagcctagctcaggagaagtgagtataaaagccccaggctgggagca
gccatcacagaagtccactcattcttggcagg (SEQ ID NO:6)

Kozak ccacc (SEQ ID NO:7)

Poly-A aataaaagatctttattttcattagatctgtgtgttggttttttgtgtg (SEQ ID NO:8)

3'-ITR aggaacccctagtgatggAgttggccactccctctctgcgcgctcgctcgctcactgaggccgggcg
accaaaggtcgcccgacgcccgggctttgcccgggcggcctcagtgagcgagcgagcgcgcagagag
ggagtggccaa (SEQ ID NO:9)

Figure 4

CS12-CRM8.2-Vrp ttggccactccctctctgcgcgctcgctcgctcactgaggccgggcgaccaaaggtcgcccgacgcc
cgggctttgcccgggcggcctcagtgagcgagcgagcgcgcagagagggagtggccaactccatcac
taggggttcctggggaggctgctggtgaatattaaccaaggtcaccccagttatcggaggagcaaa
caggggctaagtccaccggggaggctgctggtgaatattaaccaaggtcaccccagttatcggagg
agcaaacaggggctaagtccacaaatgacctattaagaatatttcatagaacgaatgttccgatgct
ctaatctctctagacaaggttcatatttgtatgggttacttattctctctttgttgactaagtcaat
aatcagaatcagcaggtttgcagtcagattggcagggataagcagcctagctcaggagaagtgagta
taaaagccccaggctgggagcagccatcacagaagtccactcattcttggcaggccaccatgcagat
tgagctgagcacctgcttcttcctgtgcctgctgaggttctgcttctctgccaccaggagatactac
ctgggggctgtggagctttcttgggactacatgcagtctgacctgggggagctgcctgtggatgcca
ggttcccacccagagtgcccaaatccttcccattcaacacctctgtggtctacaagaagaccctctt
tgtggagttcactgaccacctgttcaacattgccaaacccaggccaccctggatgggactcctggga
cccaccattcaggctgaggtgtatgacactgtggtcgtcaccctcaagaacatggcctcccaccctg
tgagcctgcatgctgtgggggtcagctactggaagtcctctgaggggctgagtatgatgaccagac
ctcccagagggagaaggaggatgacaaagtgttccctgggaagagccacacctatgtgtggcaggtc
ctcaaggagaatggccccactgcctctgacccaccctgcctgacctactcctacctttctcatgtgg
acctggtcaaggacctcaactctggactgattggggccctgctggtgtgcagggagggctccctggc
caaagagaagacccagaccctgcacaagttcattctcctgtttgctgtctttgatgagggcaagagc
tggcactctgaaaccaagaactccctgatgcaggacagggatgctgcctctgccagggcctggccca
agatgcacactgtgaatggctatgtgaacaggagcctgcctggactcattggctgccacaggaaatc
tgtctactggcatgtgattggcatggggacaaccccctgaggtgcactccattttcctggagggccac
accttcctggtcaggaaccacagacaggccagcctggagatcagccccatcaccttcctcactgccc
agaccctgctgatggacctcggacagttcctgctgttctgccacatcagctcccaccagcatgatgg
catggaggcctatgtcaaggtggacagctgccctgaggagccacagctcaggatgaagaacaatgag
gaggctgaggactatgatgatgacctgactgactctgagatggatgtggtccgctttgatgatgaca
acagcccatccttcattcagatcaggtctgtggccaagaaacaccccaagacctgggtgcactacat
tgctgctgaggaggaggactgggactatgccccactggtcctggcccctgatgacaggagctacaag
agccagtacctcaacaatggcccacagaggattggacgcaagtacaagaaagtcaggttcatggcct
acactgatgaaaccttcaagaccagggaggccattcagcatgagtctggcatcctgggcccactcct
gtatggggaggtgggggacaccctgctcatcatcttcaagaaccaggcctccaggccctacaacatc
tacccacatggcatcactgatgtcaggcccctgtacagccgcaggctgccaaaggggggtgaaacacc
tcaaggacttccccattctgcctggggagatcttcaagtacaagtggactgtcactgtggaggatgg
accaaccaaatctgaccccaggtgcctcaccagatactactccagctttgtgaacatggagagggac
ctggcctctggcctgattggcccactgctcatctgctacaaggagtctgtggaccagaggggaaacc
agatcatgtctgacaagaggaatgtgattctgttctctgtctttgatgagaacaggagctggtacct
gactgagaacattcagcgcttcctgcccaaccctgctggggtgcagctggaggaccctgagttccag
gccagcaacatcatgcactccatcaatggctatgtgtttgacagcctccagctttctgtctgcctgc
atgaggtggcctactggtacattctttctattggggcccagactgacttcctttctgtcttcttctc (Continued)

Figure 5A tggctacaccttcaaacacaagatggtgtatgaggacaccctgaccctcttcccattctctggggag
actgtgttcatgagcatggagaaccctggcctgtggattctgggatgccacaactctgacttccgca
acaggggcatgactgccctgctcaaagtctcctcctgtgacaagaacactggggactactatgagga
cagctatgaggacatctctgcctacctgctcagcaagaacaatgccattgagcccaggagcttcagc
cagaatgtgagcaataatgccaccaacccacctgtcctgaaacgccaccagagggagatcaccagga
ccaccctccagtctgaccaggaggagattgactatgatgacaccatttctgtggagatgaagaaaga
ggactttgacatctatgacgaggacgagaaccagagcccaaggagcttccagaagaagaccaggcac
tacttcattgctgctgtggagcgcctgtgggactatggcatgagctccagcccccatgtcctcagga
acagggcccagtctggctctgtgccacagttcaagaaagtggtcttccaagagttcactgatggcag
cttcacccagcccctgtacagaggggagctgaatgagcacctgggactcctgggcccatacatcagg
gctgaggtggaggacaacatcatggtgaccttccgcaaccaggcctccaggccctacagcttctaca
gctccctcatcagctatgaggaggaccagaggcaggggctgagccacgcaagaactttgtgaaacc
caatgaaaccaagacctacttctggaaagtccagcaccacatggcccccaccaaggatgagtttgac
tgcaaggcctgggcctacttctctgatgtggacctggagaaggatgtgcactctggcctgattggcc
cactcctggtctgccacaccaacaccctgaaccctgcccatggaaggcaagtgactgtgcaggagtt
tgccctcttcttcaccatctttgatgaaaccaagagctggtacttcactgagaacatggagcgcaac
tgcagggccccatgcaacattcagatggaggaccccaccttcaaagagaactaccgcttccatgcca
tcaatggctacatcatggacaccctgcctgggcttgtcatggcccaggaccagaggatcaggtggta
cctgctttctatgggctccaatgagaacattcactccatccacttctctgggcatgtcttcactgtg
cgcaagaaggaggagtacaagatggccctgtacaacctctaccctggggtctttgagactgtggaga
tgctgccctccaaagctggcatctggagggtggagtgcctcattggggagcacctgcatgctggcat
gagcaccctgttcctggtctacagcaacaagtgccagacccccctgggaatggcctctggccacatc
agggacttccagatcactgcctctggccagtatggccagtgggcccccaagctggccaggctccact
actctggatccatcaatgcctggagcaccaaggagccattcagctggatcaaagtggacctgctggc
cccatgatcatccatggcatcaagacccaggggggccaggcagaagttctccagcctgtacatcagc
cagttcatcatcatgtacagcctggatggcaagaaatggcagacctacagaggcaactccactggaa
cactcatggtcttctttggcaatgtggacagctctggcatcaagcacaacatcttcaacccccccaat
catcgccagatacatcaggctgcaccccacccactacagcatccgcagcaccctcaggatggagctg
atgggctgtgacctgaactcctgcagcatgcccctgggcatggagagcaaggccatttctgatgccc
agatcactgcctccagctacttcaccaacatgtttgccacctggagcccaagcaaggccaggctgca
cctccagggaaggagcaatgcctggaggccccaggtcaacaacccaaaggagtggctgcaggtggac
ttccagaagaccatgaaggtcactggggtgaccacccaggggtcaagagcctgctcaccagcatgt
atgtgaaggagttcctgatcagctccagccaggatggccaccagtggaccctcttcttccagaatgg
caaggtcaaggtgttccagggcaaccaggacagcttcacccctgtggtgaacagcctggaccccccc
ctcctgaccagatacctgaggattcacccccagagctgggtccaccagattgccctgaggatggagg
tcctgggatgtgaggcccaggacctgtactgatgaaataaaagatctttattttcattagatctgtg
tgttggtttttgtgtgaggaacccctagtgatggAgttggccactccctctctgcgcgctcgctcg
ctcactgaggccgggcgaccaaaggtcgcccgacgcccgggctttgcccgggcggcctcagtgagcg
agcgagcgcgcagagagggagtggccaagacgatttaaatgacaagcttggcgtaatcatggtcata
gctgtttcctgtgtgaaattgttatccgctcacaattccacacaacatacgagccggaagcataaag
tgtaaagCctggggtgcctaatgagtgagctaactcacattaattgcgttgcgctcactgcccgctt
tccagtcgggaaacctgtcgtgccagctgcattaatgaatcggccaacgcgcggggagaggcggttt (Continued)

Figure 5B gcgtattgggcgctcttccgcttcctcgctcactgactcgctgcgctcggtcgttcggctgcggcga
gcggtatcagctcactcaaaggcggtaatacggttatccacagaatcaggggataacgcaggaaaga
acatgtgagcaaaaggccagcaaaaggccaggaaccgtaaaaaggccgcgttgctggcgtttttcca
taggctccgcccccctgacgagcatcacaaaaatcgacgctcaagtcagaggtggcgaaacccgaca
ggactataaagataccaggcgtttccccctggaagctccctcgtgcgctctcctgttccgaccctgc
cgcttaccggatacctgtccgcctttctcccttcgggaagcgtggcgctttctcatagctcacgctg
taggtatctcagttcggtgtaggtcgttcgctccaagctgggctgtgtgcacgaaccccccgttcag
cccgaccgctgcgccttatccggtaactatcgtcttgagtccaacccggtaagacacgacttatcgc
cactggcagcagccactggtaacaggattagcagagcgaggtatgtaggcggtgctacagagttctt
gaagtggtggcctaactacggctacactagaagaacagtatttggtatctgcgctctgctgaagcca
gttaccttcggaaaaagagttggtagctcttgatccggcaaacaaaccaccgctggtagcggtggtt
tttttgtttgcaagcagcagattacgcgcagaaaaaaaggatctcaagaagatcctttgatcttttc
tacggggtctgacgctcagtggaacgaaaactcacgttaagggattttggtcatgagattatcaaaa
aggatcttcacctagatccttttaaattaaaaatgaagttttaaatcaatctaaagtatatatgagt
aaacttggtctgacagttaccaatgcttaatcagtgaggcacctatctcagcgatctgtctatttcg
ttcatccatagttgcctgactccccgtcgtgtagataactacgatacgggagggcttaccatctggc
cccagtgctgcaatgataccgcgagacccacgctcaccggctccagatttatcagcaataaaccagc
cagccggaagggccgagcgcagaagtggtcctgcaactttatccgcctccatccagtctattaattg
ttgccgggaagctagagtaagtagttcgccagttaatagtttgcgcaacgttgttgccattgctaca
ggcatcgtggtgtcacgctcgtcgtttggtatggcttcattcagctccggttcccaacgatcaaggc
gagttacatgatcccccatgttgtgcaaaaaagcggttagctccttcggtcctccgatcgttgtcag
aagtaagttggccgcagtgttatcactcatggttatggcagcactgcataattctcttactgtcatg
ccatccgtaagatgcttttctgtgactggtgagtactcaaccaagtcattctgagaatagtgtatgc
ggcgaccgagttgctcttgcccggcgtcaatacgggataataccgcgccacatagcagaactttaaa
agtgctcatcattggaaaacgttcttcggggcgaaaactctcaaggatcttaccgctgttgagatcc
agttcgatgtaacccactcgtgcacccaactgatcttcagcatcttttactttcaccagcgtttctg
ggtgagcaaaaacaggaaggcaaaatgccgcaaaaaagggaataagggcgacacggaaatgttgaat
actcatactcttcctttttcaatattattgaagcatttatcagggttattgtctcatgagcggatac
atatttgaatgtatttagaaaaataaacaaataggggttccgcgcacatttccccgaaaagtgccac
ctgacgtctaagaaaccattattatcatgacattaacctataaaaataggcgtatcacgaggccctt
tcgtctcgcgcgtttcggtgatgacggtgaaaacctctgacacatgcagctcccggagacggtcaca
gcttgtctgtaagcggatgccgggagcagacaagcccgtcagggcgcgtcagcgggtgttggcgggt
gtcggggctggcttaactatgcggcatcagagcagattgtactgagagtgcaccatatgcggtgtga
aataccgcacagatgcgtaaggagaaaataccgcatcaggcgccattcgccattcaggctgcgcaac
tgttgggaagggcgatcggtgcgggcctcttcgctattacgccagctggcgaaagggggatgtgctg
caaggcgattaagttgggtaacgccagggttttcccagtcacgacgttgtaaaacgacggccagtga
attcctcgagatttaaatgacg (SEQ ID NO:10)

Figure 5C

CS12-CRM8.2-V ttggccactccctctctgcgcgctcgctcgctcactgaggccgggcgaccaaaggtcgcccgacgcc
cgggctttgcccgggcggcctcagtgagcgagcgagcgcgcagagagggagtggccaactccatcac
taggggttcctgagtttaaacttcgtcgacggggaggctgctggtgaatattaaccaaggtcaccc
cagttatcggaggagcaaacaggggctaagtccaccggggaggctgctggtgaatattaaccaagg
tcaccccagttatcggaggagcaaacaggggctaagtccacaaatgacctattaagaatatttcata
gaacgaatgttccgatgctctaatctctctagacaaggttcatatttgtatgggttacttattctct
ctttgttgactaagtcaataatcagaatcagcaggtttgcagtcagattggcagggataagcagcct
agctcaggagaagtgagtataaaagccccaggctgggagcagccatcacagaagtccactcattctt
ggcaggggcgcgccgccaccatgcagattgagctgagcacctgcttcttcctgtgcctgctgaggtt
ctgcttctctgccaccaggagatactacctgggggctgtggagctttcttgggactacatgcagtct
gacctgggggagctgcctgtggatgccaggttcccacccagagtgcccaaatccttcccattcaaca
cctctgtggtctacaagaagaccctctttgtggagttcactgaccacctgttcaacattgccaaacc
caggccaccctggatgggactcctgggacccaccattcaggctgaggtgtatgacactgtggtcgtc
accctcaagaacatggcctcccaccctgtgagcctgcatgctgtgggggtcagctactggaagtcct
ctgagggggctgagtatgatgaccagacctcccagagggagaaggaggatgacaaagtgttccctgg
gaagagccacacctatgtgtggcaggtcctcaaggagaatggccccactgcctctgacccaccctgc
ctgacctactcctacctttctcatgtggacctggtcaaggacctcaactctggactgattggggccc
tgctggtgtgcagggagggctccctggccaaagagaagacccagaccctgcacaagttcattctcct
gtttgctgtctttgatgagggcaagagctggcactctgaaaccaagaactccctgatgcaggacagg
gatgctgcctctgccagggcctggcccaagatgcacactgtgaatggctatgtgaacaggagcctgc
ctggactcattggctgccacaggaaatctgtctactggcatgtgattggcatggggacaacccctga
ggtgcactccattttcctggagggccacaccttcctggtcaggaaccacagacaggccagcctggag
atcagccccatcaccttcctcactgcccagaccctgctgatggacctcggacagttcctgctgttct
gccacatcagctcccaccagcatgatggcatggaggcctatgtcaaggtggacagctgccctgagga
gccacagctcaggatgaagaacaatgaggaggctgaggactatgatgatgacctgactgactctgag
atggatgtggtccgctttgatgatgacaacagcccatccttcattcagatcaggtctgtggccaaga
aacaccccaagacctgggtgcactacattgctgctgaggaggaggactgggactatgccccactggt
cctggcccctgatgacaggagctacaagagccagtacctcaacaatggcccacagaggattggacgc
aagtacaagaaagtcaggttcatggcctacactgatgaaaccttcaagaccagggaggccattcagc
atgagtctggcatcctgggcccactcctgtatggggaggtgggggacaccctgctcatcatcttcaa
gaaccaggcctccaggccctacaacatctacccacatggcatcactgatgtcaggcccctgtacagc
cgcaggctgccaaaggggggtgaaacacctcaaggacttccccattctgcctggggagatcttcaagt
acaagtggactgtcactgtggaggatggaccaaccaaatctgaccccaggtgcctcaccagatacta
ctccagctttgtgaacatggagagggacctggcctctggcctgattggcccactgctcatctgctac
aaggagtctgtggaccagaggggaaaccagatcatgtctgacaagaggaatgtgattctgttctctg
tctttgatgagaacaggagctggtacctgactgagaacattcagcgcttcctgcccaaccctgctgg
ggtgcagctggaggaccctgagttccaggccagcaacatcatgcactccatcaatggctatgtgttt
gacagcctccagctttctgtctgcctgcatgaggtggcctactggtacattctttctattggggccc
agactgacttcctttctgtcttcttctctggctacaccttcaaacacaagatggtgtatgaggacac
cctgaccctcttcccattctctggggagactgtgttcatgagcatggagaaccctggcctgtggatt
ctgggatgccacaactctgacttccgcaacaggggcatgactgccctgctcaaagtctcctcctgtg
(Continued)

Figure 6A acaagaacactggggactactatgaggacagctatgaggacatctctgcctacctgctcagcaagaa
caatgccattgagcccaggagcttcagccagaatgtgagcaataatgccaccaacccacctgtcctg
aaacgccaccagagggagatcaccaggaccaccctccagtctgaccaggaggagattgactatgatg
acaccatttctgtggagatgaagaaagaggactttgacatctatgacgaggacgagaaccagagccc
aaggagcttccagaagaagaccaggcactacttcattgctgctgtggagcgcctgtgggactatggc
atgagctccagccccccatgtcctcaggaacagggcccagtctggctctgtgccacagttcaagaaag
tggtcttccaagagttcactgatggcagcttcacccagcccctgtacagaggggagctgaatgagca
cctgggactcctgggcccatacatcagggctgaggtggaggacaacatcatggtgaccttccgcaac
caggcctccaggccctacagcttctacagctccctcatcagctatgaggaggaccagaggcagggg
ctgagccacgcaagaactttgtgaaacccaatgaaaccaagacctacttctggaaagtccagcacca
catggcccccaccaaggatgagtttgactgcaaggcctgggcctacttctctgatgtggacctggag
aaggatgtgcactctggcctgattggcccactcctggtctgccacaccaacaccctgaaccctgccc
atggaaggcaagtgactgtgcaggagtttgccctcttcttcaccatctttgatgaaaccaagagctg
gtacttcactgagaacatggagcgcaactgcagggccccatgcaacattcagatggaggaccccacc
ttcaaagagaactaccgcttccatgccatcaatggctacatcatggacaccctgcctgggcttgtca
tggcccaggaccagaggatcaggtggtacctgctttctatgggctccaatgagaacattcactccat
ccacttctctgggcatgtcttcactgtgcgcaagaaggaggagtacaagatggccctgtacaacctc
taccctggggtctttgagactgtggagatgctgccctccaaagctggcatctggagggtggagtgcc
tcattggggagcacctgcatgctggcatgagcaccctgttcctggtctacagcaacaagtgccagac
ccccctgggaatggcctctggccacatcagggacttccagatcactgcctctggccagtatggccag
tgggcccccaagctggccaggctccactactctggatccatcaatgcctggagcaccaaggagccat
tcagctggatcaaagtggacctgctggcccccatgatcatccatggcatcaagacccaggggggccag
gcagaagttctccagcctgtacatcagccagttcatcatcatgtacagcctggatggcaagaaatgg
cagacctacagaggcaactccactggaacactcatggtcttctttggcaatgtggacagctctggca
tcaagcacaacatcttcaacccccccaatcatcgccagatacatcaggctgcaccccacccactacag
catccgcagcaccctcaggatggagctgatgggctgtgacctgaactcctgcagcatgcccctgggc
atggagagcaaggccatttctgatgcccagatcactgcctccagctacttcaccaacatgtttgcca
cctggagcccaagcaaggccaggctgcacctccagggaaggagcaatgcctggaggccccaggtcaa
caacccaaaggagtggctgcaggtggacttccagaagaccatgaaggtcactggggtgaccacccag
gggggtcaagagcctgctcaccagcatgtatgtgaaggagttcctgatcagctccagccaggatggcc
accagtggaccctcttcttccagaatggcaaggtcaaggtgttccagggcaaccaggacagcttcac
ccctgtggtgaacagcctggaccccccctcctgaccagatacctgaggattcaccccccagagctgg
gtccaccagattgccctgaggatggaggtcctgggatgtgaggcccaggacctgtactgatgagcgg
ccgctcttagtagcagtatcgataataaaagatctttattttcattagatctgtgtgttggtttttt
gtgtgttaattaagctcgcgaaggaacccctagtgatggAgttggccactccctctctgcgcgctcg
ctcgctcactgaggccgggcgaccaaaggtcgcccgacgcccgggctttgcccgggcggcctcagtg
agcgagcgagcgcgcagagagggagtggccaa (SEQ ID NO:38)

Figure 6B

CS04-FL-NA atgcagattgagctgagcacctgcttcttcctgtgcctgctgaggttctgcttctctgccaccagga
gatactacctggggggctgtggagctttcttgggactacatgcagtctgacctgggggagctgcctgt
ggatgccaggttcccacccagagtgcccaaatccttcccattcaacacctctgtggtctacaagaag
accctctttgtggagttcactgaccacctgttcaacattgccaaacccaggccaccctggatgggac
tcctgggacccaccattcaggctgaggtgtatgacactgtggtcatcaccctcaagaacatggcctc
ccaccctgtgagcctgcatgctgtgggggtcagctactggaaggcctctgagggggctgagtatgat
gaccagacctcccagagggagaaggaggatgacaaagtgttccctgggggcagccacacctatgtgt
ggcaggtcctcaaggagaatggccccatggcctctgacccactctgcctgacctactcctacctttc
tcatgtggacctggtcaaggacctcaactctggactgattggggccctgctggtgtgcagggagggc
tccctggccaaagagaagacccagaccctgcacaagttcattctcctgtttgctgtctttgatgagg
gcaagagctggcactctgaaaccaagaactccctgatgcaggacagggatgctgcctctgccagggc
ctggcccaagatgcacactgtgaatggctatgtgaacaggagcctgcctggactcattggctgccac
aggaaatctgtctactggcatgtgattggcatggggacaacccctgaggtgcactccattttcctgg
agggccacaccttcctggtcaggaaccacagacaggccagcctggagatcagccccatcaccttcct
cactgcccagaccctgctgatggacctcggacagttcctgctgttctgccacatcagctcccaccag
catgatggcatggaggcctatgtcaaggtggacagctgccctgaggagccacagctcaggatgaaga
acaatgaggaggctgaggactatgatgatgacctgactgactctgagatggatgtggtccgctttga
tgatgacaacagcccatccttcattcagatcaggtctgtggccaagaaacaccccaagacctgggtg
cactacattgctgctgaggaggaggactgggactatgccccactggtcctggcccctgatgacagga
gctacaagagccagtacctcaacaatggcccacagaggattggacgcaagtacaagaaagtcaggtt
catggcctacactgatgaaaccttcaagaccagggaggccattcagcatgagtctggcatcctgggc
ccactcctgtatggggaggtgggggacaccctgctcatcatcttcaagaaccaggcctccaggccct
acaacatctacccacatggcatcactgatgtcaggcccctgtacagccgcaggctgccaaaggggt
gaaacacctcaaggacttccccattctgcctggggagatcttcaagtacaagtggactgtcactgtg
gaggatggaccaaccaaatctgaccccaggtgcctcaccagatactactccagctttgtgaacatgg
agagggacctggcctctggcctgattggcccactgctcatctgctacaaggagtctgtggaccagag
gggaaaccagatcatgtctgacaagaggaatgtgattctgttctctgtctttgatgagaacaggagc
tggtacctgactgagaacattcagcgcttcctgcccaaccctgctggggtgcagctggaggaccctg
agttccaggccagcaacatcatgcactccatcaatggctatgtgtttgacagcctccagctttctgt
ctgcctgcatgaggtggcctactggtacattctttctattggggcccagactgacttcctttctgtc
ttcttctctggctacaccttcaaacacaagatggtgtatgaggacaccctgaccctcttcccattct
ctggggagactgtgttcatgagcatggagaaccctggcctgtggattctgggatgccacaactctga
cttccgcaacaggggcatgactgccctgctcaaagtctcctcctgtgacaagaacactggggactac
tatgaggacagctatgaggacatctctgcctacctgctcagcaagaacaatgccattgagcccagga
gcttcagccagaatccacctgtcctgaaacgccaccagagggagatcaccaggaccaccctccagtc
tgaccaggaggagattgactatgatgacaccatttctgtggagatgaagaaagaggactttgacatc
tatgacgaggacgagaaccagagcccaaggagcttccagaagaagaccaggcactacttcattgctg
ctgtggagcgcctgtgggactatggcatgagctccagcccccatgtcctcaggaacagggcccagtc
tggctctgtgccacagttcaagaaagtggtcttccaagagttcactgatggcagcttcacccagccc
ctgtacagaggggagctgaatgagcacctgggactcctgggcccatacatcagggctgaggtggagg
acaacatcatggtgaccttccgcaaccaggcctccaggccctacagcttctacagctccctcatcag
ctatgagGaggaccagaggcaggggctgagccacgcaagaactttgtgaaacccaatgaaaccaag
acctacttctggaaagtccagcaccacatggcccccaccaaggatgagtttgactgcaaggcctggg (Continued)

Figure 7A cctacttctctgatgtggacctggagaaggatgtgcactctggcctgattggcccactcctggtc
tgccacaccaacaccctgaaccctgcccatggaaggcaagtgactgtgcaggagtttgccctctt
cttcaccatctttgatgaaaccaagagctggtacttcactgagaacatggagcgcaactgcaggg
ccccatgcaacattcagatggaggaccccaccttcaaagagaactaccgcttccatgccatcaat
ggctacatcatggacaccctgcctgggcttgtcatggcccaggaccagaggatcaggtggtacct
gctttctatgggctccaatgagaacattcactccatccacttctctgggcatgtcttcactgtgc
gcaagaaggaggagtacaagatggccctgtacaacctctaccctggggtctttgagactgtggag
atgctgccctccaaagctggcatctggagggtggagtgcctcattggggagcacctgcatgctgg
catgagcaccctgttcctggtctacagcaacaagtgccagacccccctgggaatggcctctggcc
acatcagggacttccagatcactgcctctggccagtatggccagtgggcccccaagctggccagg
ctccactactctggatccatcaatgcctggagcaccaaggagccattcagctggatcaaagtgga
cctgctggcccccatgatcatccatggcatcaagacccaggggggccaggcagaagttctccagcc
tgtacatcagccagttcatcatcatgtacagcctggatggcaagaaatggcagacctacagaggc
aactccactggaacactcatggtcttctttggcaatgtggacagctctggcatcaagcacaacat
cttcaacccccccaatcatcgccagatacatcaggctgcaccccacccactacagcatccgcagca
ccctcaggatggagctgatgggctgtgacctgaactcctgcagcatgcccctgggcatggagagc
aaggccatttctgatgcccagatcactgcctccagctacttcaccaacatgtttgccacctggag
cccaagcaaggccaggctgcacctccagggaaggagcaatgcctggaggccccaggtcaacaacc
caaaggagtggctgcaggtggacttccagaagaccatgaaggtcactggggtgaccacccagggg
gtcaagagcctgctcaccagcatgtatgtgaaggagttcctgatcagctccagccaggatggcca
ccagtggaccctcttcttccagaatggcaaggtcaaggtgttccagggcaaccaggacagcttca
cCcctgtggtgaacagcctggacccccccctcctgaccagatacctgaggattcacccccagagc
tgggtccaccagattgccctgaggatggaggtcctgggatgtgaggcccaggacctgtactga
(SEQ ID NO:37)

Figure 7B

```
NG1:  V   S   N   N   V   S   N   N   A   T   N   N   A   T   N  (SEQ ID NO:11)
     GTG AGC AAC AAT GTG AGC AAC AAT GCC ACC AAT AAT GCT ACC AAC (SEQ ID NO:12)

NG4:  V   S   N   N   A   T   N   N   V   S   N  (SEQ ID NO:13)
     GTG AGC AAC AAT GCC ACC AAC AAT GTG AGC AAC (SEQ ID NO:14)

NG5:  V   S   N   N   A   T   N  (SEQ ID NO:15)
     GTG AGC AAT AAT GCC ACC AAC (SEQ ID NO:16)

NG6:  V   S   N   N  (SEQ ID NO:17)
     GTG AGC AAT AAT (SEQ ID NO:18)

NG9:  R   S   L  (SEQ ID NO:19)
     AGG AGC CTG (SEQ ID NO:20)

NG10: A   T   N   V   S   N   N   S   A   T   S   A   D   S   A   V   S  (SEQ ID NO:21)
     GCC ACT AAT GTG TCT AAC AAC TCT GCT ACC TCT GCT GAC TCT GCT GTG AGC (SEQ ID NO:22)

NG16: A   T   N   Y   V   N   R   S   L  (SEQ ID NO:23)
     GCC ACC AAC TAT GTG AAC AGG AGC CTG (SEQ ID NO:24)
```

Figure 8A

```
NG17: A   T   N   Y   V   N   R   S   L   S   A   T   S   A   D   S   A   V   S   Q   N   (SEQ ID NO:25)
      GCC ACC AAC TAT GTG AAC AGG AGC CTG TCT GCC ACC TCT GCT GAC TCT GCT GTG AGC CAG AAT (SEQ ID NO:26)

NG18: V   S   N   N   V   S   N   A   V   S   A   V   S   A   (SEQ ID NO:27)
      GTG AGC AAC AAT GTG AGC AAT GCT GTG TCT GCT GTG TCT GCT (SEQ ID NO:28)

NG19: I   T   V   A   S   A   T   S   N   I   T   V   A   S   A   D   (SEQ ID NO:29)
      ATC ACT GTG GCC TCT GCC ACC TCT AAC ATC ACT GTG GCC TCT GCT GAC (SEQ ID NO:30)

NG20: I   T   V   T   N   I   T   V   T   A   (SEQ ID NO:31)
      ATC ACT GTG ACC AAC ATC ACT GTG ACT GCC (SEQ ID NO:32)

NG21: Q   T   V   T   N   I   T   V   T   A   (SEQ ID NO:33)
      CAG ACT GTG ACC AAC ATC ACT GTG ACT GCC (SEQ ID NO:34)

NGV:  A   T   N   V   S   N   N   S   N   T   S   N   D   S   N   V   S   (SEQ ID NO:35)
      GCC ACT AAT GTG TCT AAC AAC AGC AAC ACC AGC AAT GAC AGC AAT GTG TCT (SEQ ID NO:36)
```

Figure 8B

| | | | | In vivo biopotency ("Line E" mice) | | | | In vitro biopotency (HepG2 cells) | | |
|---|---|---|---|---|---|---|---|---|---|---|
| Vector | Promoter | CDS | Sequence modi-fication(s) | Number of mice | Average FVIII Expression at day 14 [IU/mL] | Standard Deviation | Fold expression increase | BPU | Standard Deviation | Fold expression increase* |
| vCS04 | mTTR promoter/enhancer | CS04 | - | 44 | 2.1 | 1.7 | **1.0 (ref.)** | 1.0 | 0.6 | **1.0 (ref.)** |
| vCS115 | 1xCRM8/hTTR | CS04 | - | 8 | 2.5 | 0.9 | **1.2** | 2.1 | n.a. | **2.2** |
| vCS116 | 2xCRM8/hTTR | CS04 | - | 8 | 1.9 | 0.6 | **0.9** | 3.6 | n.a. | **3.7** |
| vNG5/CS04 | mTTR promoter/enhancer | CS04 | NG5 | 8 | 4.0 | 2.6 | **1.9** | 0.6 | n.a. | **0.6** |
| vNG5/CS117 | 1xCRM8/hTTR | CS04 | NG5 | 7 | 3.2 | 1.0 | **1.5** | 1.5 | 0.1 | **1.5** |
| vNG5/CS118 | 2xCRM8/hTTR | CS04 | NG5 | 7 | 2.9 | 1.8 | **1.4** | 2.3 | n.a. | **2.4** |
| vX5/CS24 | mTTR promoter/enhancer | CS04 | X5 | 16 | 6.5 | 2.1 | **3.1** | 3.8 | 1.9 | **4.0** |
| vX5/CS101 | 1xCRM8/hTTR | CS04 | X5 | 7 | 5.2 | 3.2 | **2.5** | 7.0 | n.a. | **7.3** |
| vX5/CS105 | 2xCRM8/hTTR | CS04 | X5 | 8 | 5.1 | 2.8 | **2.5** | 20.3 | n.a. | **21.2** |
| vX5/NG5/CS125 | mTTR promoter/enhancer | CS04 | NG / X5 | 8 | 9.3 | 2.8 | **4.5** | 3.0 | 1.0 | **3.2** |
| vX5/NG5/CS119 | 1xCRM8/hTTR | CS04 | NG / X5 | 8 | 7.6 | 5.8 | **3.6** | 13.6 | 4.4 | **14.2** |
| vX5/NG5/CS120 | 2xCRM8/hTTR | CS04 | NG / X5 | 8 | 11.4 | 5.0 | **5.5** | 19.0 | n.a. | **19.8** |

Figure 12

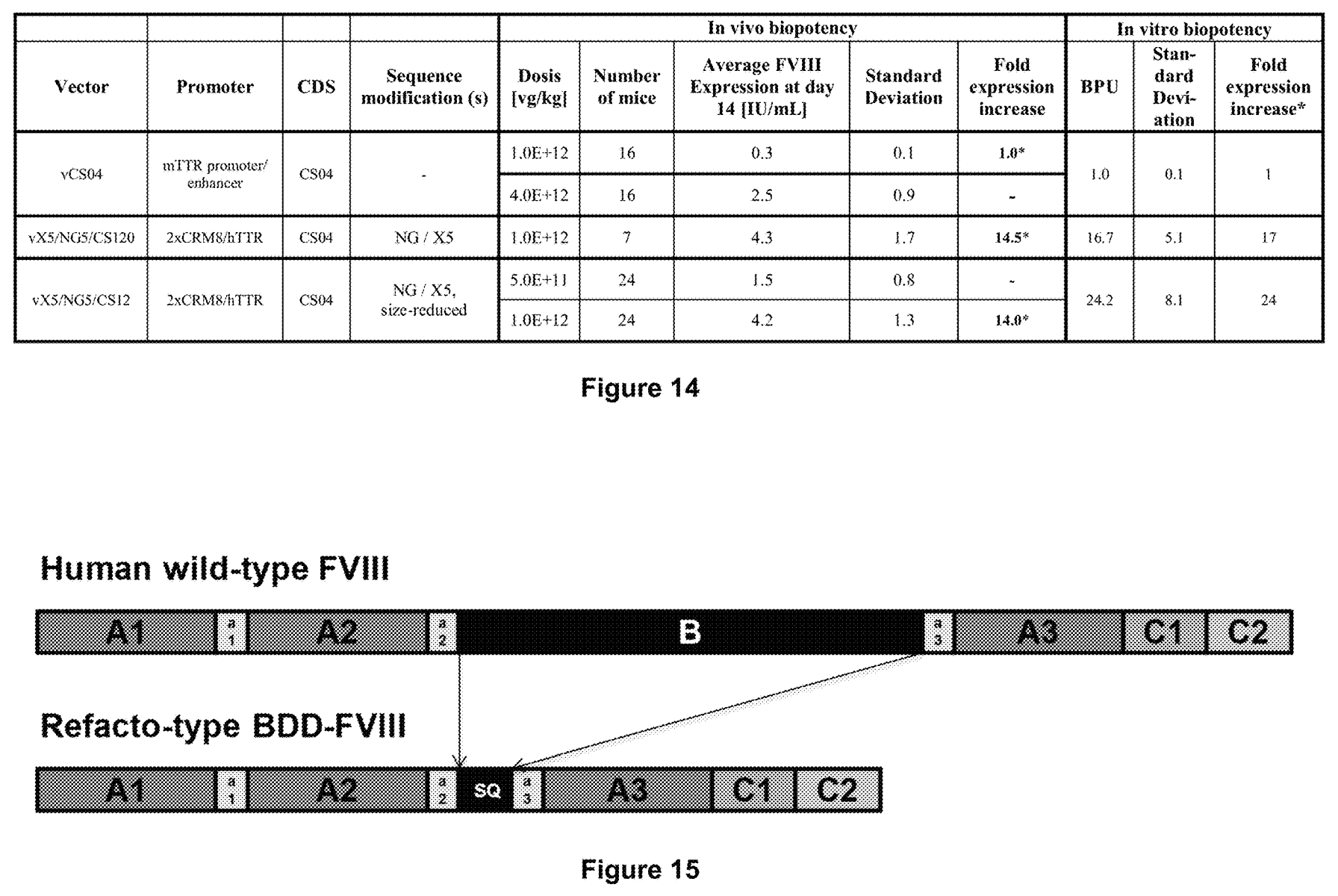

| Vector | Promoter | CDS | Sequence modification (s) | In vivo biopotency | | | | | In vitro biopotency | | |
|---|---|---|---|---|---|---|---|---|---|---|---|
| | | | | Dosis [vg/kg] | Number of mice | Average FVIII Expression at day 14 [IU/mL] | Standard Deviation | Fold expression increase | BPU | Standard Deviation | Fold expression increase* |
| vCS04 | mTTR promoter/ enhancer | CS04 | - | 1.0E+12 | 16 | 0.3 | 0.1 | **1.0*** | 1.0 | 0.1 | 1 |
| | | | | 4.0E+12 | 16 | 2.5 | 0.9 | - | | | |
| vX5/NG5/CS120 | 2xCRM8/hTTR | CS04 | NG / X5 | 1.0E+12 | 7 | 4.3 | 1.7 | **14.5*** | 16.7 | 5.1 | 17 |
| vX5/NG5/CS12 | 2xCRM8/hTTR | CS04 | NG / X5, size-reduced | 5.0E+11 | 24 | 1.5 | 0.8 | - | 24.2 | 8.1 | 24 |
| | | | | 1.0E+12 | 24 | 4.2 | 1.3 | **14.0*** | | | |

Figure 14

Human wild-type FVIII

A1 a1 A2 a2 B a3 A3 C1 C2

Refacto-type BDD-FVIII

A1 a1 A2 a2 SQ a3 A3 C1 C2

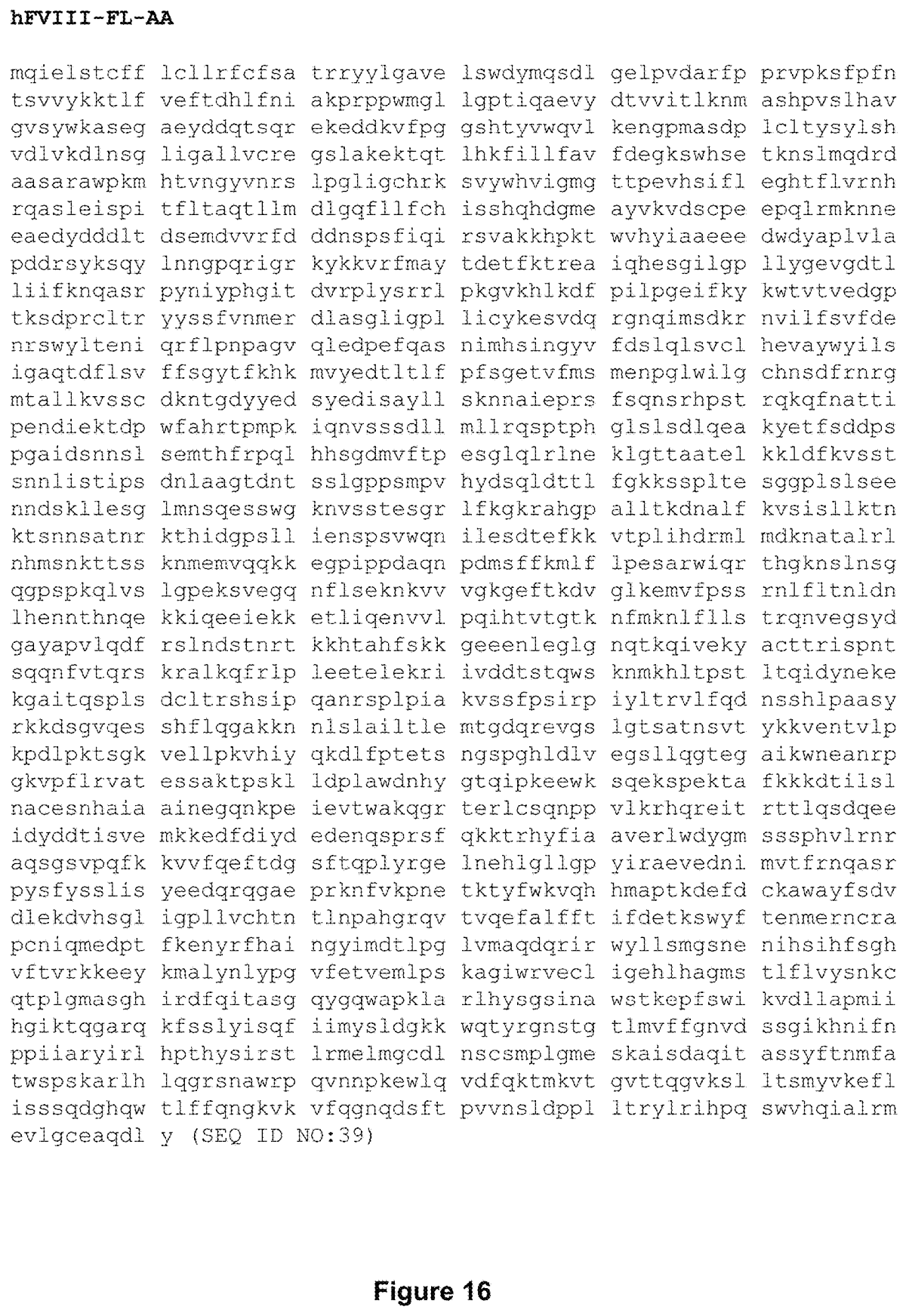

Figure 15 hFVIII-FL-AA mqielstcff lcllrfcfsa trryylgave lswdymqsdl gelpvdarfp prvpksfpfn
tsvvykktlf veftdhlfni akprppwmgl lgptiqaevy dtvvitlknm ashpvslhav
gvsywkaseg aeyddqtsqr ekeddkvfpg gshtyvwqvl kengpmasdp lcltysylsh
vdlvkdlnsg ligallvcre gslakektqt lhkfillfav fdegkswhse tknslmqdrd
aasarawpkm htvngyvnrs lpgligchrk svywhvigmg ttpevhsifl eghtflvrnh
rqasleispi tfltaqtllm dlgqfllfch isshqhdgme ayvkvdscpe epqlrmknne
eaedydddlt dsemdvvrfd ddnspsfiqi rsvakkhpkt wvhyiaaeee dwdyaplvla
pddrsyksqy lnngpqrigr kykkvrfmay tdetfktrea iqhesgilgp llygevgdtl
liifknqasr pyniyphgit dvrplysrrl pkgvkhlkdf pilpgeifky kwtvtvedgp
tksdprcltr yyssfvnmer dlasgligpl licykesvdq rgnqimsdkr nvilfsvfde
nrswylteni qrflpnpagv qledpefqas nimhsingyv fdslqlsvcl hevaywyils
igaqtdflsv ffsgytfkhk mvyedtltlf pfsgetvfms menpglwilg chnsdfrnrg
mtallkvssc dkntgdyyed syedisayll sknnaieprs fsqnsrhpst rqkqfnatti
pendiektdp wfahrtpmpk iqnvsssdll mllrqsptph glslsdlqea kyetfsddps
pgaidsnnsl semthfrpql hhsgdmvftp esglqlrlne klgttaatel kkldfkvsst
snnlistips dnlaagtdnt sslgppsmpv hydsqldttl fgkkssplte sggplslsee
nndskllesg lmnsqesswg knvsstesgr lfkgkrahgp alltkdnalf kvsisllktn
ktsnnsatnr kthidgpsll ienspsvwqn ilesdtefkk vtplihdrml mdknatalrl
nhmsnkttss knmemvqqkk egpippdaqn pdmsffkmlf lpesarwiqr thgknslnsg
qgpspkqlvs lgpeksvegq nflseknkvv vgkgeftkdv glkemvfpss rnlfltnldn
lhennthnqe kkiqeeiekk etliqenvvl pqihtvtgtk nfmknlflls trqnvegsyd
gayapvlqdf rslndstnrt kkhtahfskk geeenleglg nqtkqiveky acttrispnt
sqqnfvtqrs kralkqfrlp leetelekri ivddtstqws knmkhltpst ltqidyneke
kgaitqspls dcltrshsip qanrsplpia kvssfpsirp iyltrvlfqd nsshlpaasy
rkkdsgvqes shflqgakkn nlslailtle mtgdqrevgs lgtsatnsvt ykkventvlp
kpdlpktsgk vellpkvhiy qkdlfptets ngspghldlv egsllqgteg aikwneanrp
gkvpflrvat essaktpskl ldplawdnhy gtqipkeewk sqekspekta fkkkdtilsl
nacesnhaia ainegqnkpe ievtwakqgr terlcsqnpp vlkrhqreit rttlqsdqee
idyddtisve mkkedfdiyd edenqsprsf qkktrhyfia averlwdygm sssphvlrnr
aqsgsvpqfk kvvfqeftdg sftqplyrge lnehlgllgp yiraevedni mvtfrnqasr
pysfysslis yeedqrqgae prknfvkpne tktyfwkvqh hmaptkdefd ckawayfsdv
dlekdvhsgl igpllvchtn tlnpahgrqv tvqefalfft ifdetkswyf tenmerncra
pcniqmedpt fkenyrfhai ngyimdtlpg lvmaqdqrir wyllsmgsne nihsihfsgh
vftvrkkeey kmalynlypg vfetvemlps kagiwrvecl igehlhagms tlflvysnkc
qtplgmasgh irdfqitasg qygqwapkla rlhysgsina wstkepfswi kvdllapmii
hgiktqgarq kfsslyisqf iimysldgkk wqtyrgnstg tlmvffgnvd ssgikhnifn
ppiiaryirl hpthysirst lrmelmgcdl nscsmplgme skaisdaqit assyftnmfa
twspskarlh lqgrsnawrp qvnnpkewlq vdfqktmkvt gvttqgvksl ltsmyvkefl
isssqdghqw tlffqngkvk vfqgnqdsft pvvnsldppl ltrylrihpq swvhqialrm
evlgceaqdl y (SEQ ID NO:39)

Figure 16

BDLO04 - agc ttcagccaga atccacctgt cctgaaacgc caccagagg (SEQ ID NO:40)

BDLNG1 - agcttcagccagaatGTGAGCAACAATGTGAGCAACAATGCCACCAATAATGCTACCAACccacctgtcctgaaacgccaccagagg (SEQ ID NO:41)

BDLNG4 - agcttcagccagaatGTGAGCAACAATGCCACCAACAATGTGAGCAACccacctgtcctgaaacgccaccagagg (SEQ ID NO:42)

BDLNG5 - agcttcagccagaatGTGAGCAATAATGCCACCAACccacctgtcctgaaacgccaccagagg (SEQ ID NO:43)

BDLNG6 - agcttcagccagaatGTGAGCAATAATccacctgtcctgaaacgccaccagagg (SEQ ID NO:44)

BDLNG9 - agcttcagccagaatAGGAGCCTGccacctgtcctgaaacgccaccagagg (SEQ ID NO:45)

BDLNG10 - agcttcagccagaatGCCACTAATGTGTCTAACAACTCTGCTACCTCTGCTGACTCTGCTGTGAGCccacctgtcctgaaacgccaccagagg (SEQ ID NO:46)

BDLNG16 - agcttcagccagaatGCCACCAACTATGTGAACAGGAGCCTGccacctgtcctgaaacgccaccagagg (SEQ ID NO:47)

BDLNG17 - agcttcagccagaatGCCACCAACTATGTGAACAGGAGCCTGTCTGCCACCTCTGCTGACTCTGCTGTGAGCCAGAATccacctgtcctgaaacgccaccagagg(SEQ ID NO:48)

BDLNG18 - agcttcagccagaatGTGAGCAACAATGTGAGCAATGCTGTGTCTGCTGTGTCTGCTccacctgtcctgaaacgccaccagagg (SEQ ID NO:49)

BDLNG19 - agcttcagccagaatATCACTGTGGCCTCTGCCACCTCTAACATCACTGTGGCCTCTGCTGACccacctgtcctgaaacgccaccagagg (SEQ ID NO:50)

BDLNG20 - agcttcagccagaatATCACTGTGACCAACATCACTGTGACTGCCccacctgtcctgaaacgccaccagagg (SEQ ID NO:51)

BDLNG21 - agcttcagccagaatCAGACTGTGACCAACATCACTGTGACTGCCccacctgtcctgaaacgccaccagagg (SEQ ID NO:52)

BDLNGV - agcttcagccagaatGCCACTAATGTGTCTAACAACAGCAACACCAGCAATGACAGCAATGTGTCTccacctgtcctgaaacgccaccagagg (SEQ ID NO:53)

Figure 17

Plasmid backbone of CS12-CRM8.2-Vrp gacgatttaaatgacaagcttggcgtaatcatggtcatagctgtttcctgtgtgaaattgttatccg
ctcacaattccacacaacatacgagccggaagcataaagtgtaaagcctggggtgcctaatgagtga
gctaactcacattaattgcgttgcgctcactgcccgctttccagtcgggaaacctgtcgtgccagct
gcattaatgaatcggccaacgcgcggggagaggcggtttgcgtattgggcgctcttccgcttcctcg
ctcactgactcgctgcgctcggtcgttcggctgcggcgagcggtatcagctcactcaaaggcggtaa
tacggttatccacagaatcaggggataacgcaggaaagaacatgtgagcaaaaggccagcaaaaggc
caggaaccgtaaaaaggccgcgttgctggcgtttttccataggctccgcccccctgacgagcatcac
aaaaatcgacgctcaagtcagaggtggcgaaacccgacaggactataaagataccaggcgtttcccc
ctggaagctccctcgtgcgctctcctgttccgaccctgccgcttaccggatacctgtccgcctttct
cccttcgggaagcgtggcgctttctcatagctcacgctgtaggtatctcagttcggtgtaggtcgtt
cgctccaagctgggctgtgtgcacgaaccccccgttcagcccgaccgctgcgccttatccggtaact
atcgtcttgagtccaacccggtaagacacgacttatcgccactggcagcagccactggtaacaggat
tagcagagcgaggtatgtaggcggtgctacagagttcttgaagtggtggcctaactacggctacact
agaagaacagtatttggtatctgcgctctgctgaagccagttaccttcggaaaaagagttggtagct
cttgatccggcaaacaaaccaccgctggtagcggtggtttttttgtttgcaagcagcagattacgcg
cagaaaaaaaggatctcaagaagatcctttgatcttttctacggggtctgacgctcagtggaacgaa
aactcacgttaagggattttggtcatgagattatcaaaaaggatcttcacctagatccttttaaatt
aaaaatgaagttttaaatcaatctaaagtatatatgagtaaacttggtctgacagttaccaatgctt
aatcagtgaggcacctatctcagcgatctgtctatttcgttcatccatagttgcctgactccccgtc
gtgtagataactacgatacgggagggcttaccatctggccccagtgctgcaatgataccgcgagacc
cacgctcaccggctccagatttatcagcaataaaccagccagccggaagggccgagcgcagaagtgg
tcctgcaactttatccgcctccatccagtctattaattgttgccgggaagctagagtaagtagttcg
ccagttaatagtttgcgcaacgttgttgccattgctacaggcatcgtggtgtcacgctcgtcgtttg
gtatggcttcattcagctccggttcccaacgatcaaggcgagttacatgatcccccatgttgtgcaa
aaaagcggttagctccttcggtcctccgatcgttgtcagaagtaagttggccgcagtgttatcactc
atggttatggcagcactgcataattctcttactgtcatgccatccgtaagatgcttttctgtgactg
gtgagtactcaaccaagtcattctgagaatagtgtatgcggcgaccgagttgctcttgcccggcgtc
aatacgggataataccgcgccacatagcagaactttaaaagtgctcatcattggaaaacgttcttcg
gggcgaaaactctcaaggatcttaccgctgttgagatccagttcgatgtaacccactcgtgcaccca
actgatcttcagcatcttttactttcaccagcgtttctgggtgagcaaaaacaggaaggcaaaatgc
cgcaaaaaagggaataagggcgacacggaaatgttgaatactcatactcttcctttttcaatattat
tgaagcatttatcagggttattgtctcatgagcggatacatatttgaatgtatttagaaaaataaac
aaataggggttccgcgcacatttccccgaaaagtgccacctgacgtctaagaaaccattattatcat
gacattaacctataaaaataggcgtatcacgaggccctttcgtctcgcgcgtttcggtgatgacggt
gaaaacctctgacacatgcagctcccggagacggtcacagcttgtctgtaagcggatgccgggagca
gacaagcccgtcagggcgcgtcagcgggtgttggcgggtgtcggggctggcttaactatgcggcatc
agagcagattgtactgagagtgcaccatatgcggtgtgaaataccgcacagatgcgtaaggagaaaa
taccgcatcaggcgccattcgccattcaggctgcgcaactgttgggaagggcgatcggtgcgggcct
cTtcgctattacgccagctggcgaaagggggatgtgctgcaaggcgattaagttgggtaacgccagg
gttttcccagtcacgacgttgtaaaacgacggccagtgaattcctcgagatttaaatgacg (SEQ ID NO:54)

Figure 18 pMB1 Replicon tggcgtaatc atggtcatag ctgtttcctg tgtgaaattg ttatccgctc acaattccac
acaacatacg agccggaagc ataaagtgta aagcctgggg tgcctaatga gtgagctaac
tcacattaat tgcgttgcgc tcactgcccg ctttccagtc gggaaacctg tcgtgccagc
tgcattaatg aatcggccaa cgcgcgggga gaggcggttt gcgtattggg cgctcttccg
cttcctcgct cactgactcg ctgcgctcgg tcgttcggct gcggcgagcg gtatcagctc
actcaaaggc ggtaatacgg ttatccacag aatcagggga taacgcagga aagaacatgt
gagcaaaagg ccagcaaaag gccaggaacc gtaaaaaggc cgcgttgctg gcgtttttcc
ataggctccg cccccctgac gagcatcaca aaaatcgacg ctcaagtcag aggtggcgaa
acccgacagg actataaaga taccaggcgt ttccccctgg aagctccctc gtgcgctctc
ctgttccgac cctgccgctt accggatacc tgtccgcctt tctcccttcg ggaagcgtgg
cgctttctca tagctcacgc tgtaggtatc tcagttcggt gtaggtcgtt cgctccaagc
tgggctgtgt gcacgaaccc cccgttcagc ccgaccgctg cgccttatcc ggtaactatc
gtcttgagtc caacccggta agacacgact tatcgccact ggcagcagcc actggtaaca
ggattagcag agcgaggtat gtaggcggtg ctacagagtt cttgaagtgg tggcctaact
acggctacac tagaagaaca gtatttggta tctgcgctct gctgaagcca gttaccttcg
gaaaaagagt tggtagctct tgatccggca aacaaaccac cgctggtagc ggtggttttt
ttgtttgcaa gcagcagatt acgcgcagaa aaaaaggatc tcaagaagat ccttt
(SEQ ID NO:55)

Bla(ApR)

ttacca atgcttaatc agtgaggcac ctatctcagc gatctgtcta tttcgttcat
ccatagttgc ctgactcccc gtcgtgtaga taactacgat acgggagggc ttaccatctg
gccccagtgc tgcaatgata ccgcgagacc cacgctcacc ggctccagat ttatcagcaa
taaaccagcc agccggaagg gccgagcgca gaagtggtcc tgcaacttta tccgcctcca
tccagtctat taattgttgc cgggaagcta gagtaagtag ttcgccagtt aatagtttgc
gcaacgttgt tgccattgct acaggcatcg tggtgtcacg ctcgtcgttt ggtatggctt
cattcagctc cggttcccaa cgatcaaggc gagttacatg atcccccatg ttgtgcaaaa
aagcggttag ctccttcggt cctccgatcg ttgtcagaag taagttggcc gcagtgttat
cactcatggt tatggcagca ctgcataatt ctcttactgt catgccatcc gtaagatgct
tttctgtgac tggtgagtac tcaaccaagt cattctgaga atagtgtatg cggcgaccga
gttgctcttg cccggcgtca atacgggata ataccgcgcc acatagcaga actttaaaag
tgctcatcat tggaaaacgt tcttcggggc gaaaactctc aaggatctta ccgctgttga
gatccagttc gatgtaaccc actcgtgcac ccaactgatc ttcagcatct tttactttca
ccagcgtttc tgggtgagca aaaacaggaa ggcaaaatgc cgcaaaaaag ggaataaggg
cgacacggaa atgttgaata ctcat (SEQ ID NO:56)

Figure 19

CS12-CRM8.2-Vp tcgcgcgtttcggtgatgacggtgaaaacctctgacacatgcagctcccggagacggtcacagcttg
tctgtaagcggatgccgggagcagacaagcccgtcagggcgcgtcagcgggtgttggcgggtgtcgg
ggctggcttaactatgcggcatcagagcagattgtactgagagtgcaccatatgcggtgtgaaatac
cgcacagatgcgtaaggagaaaataccgcatcaggcgccattcgccattcaggctgcgcaactgttg
ggaagggcgatcggtgcgggcctcttcgctattacgccagctggcgaaagggggatgtgctgcaagg
cgattaagttgggtaacgccagggttttcccagtcacgacgttgtaaaacgacggccagtgaattcc
tcgagatttaaatgacgttggccactccctctctgcgcgctcgctcgctcactgaggccgggcgacc
aaaggtcgcccgacgcccgggctttgcccgggcggcctcagtgagcgagcgagcgcgcagagaggga
gtggccaactccatcactaggggttcctgagtttaaacttcgtcgacgggggaggctgctggtgaat
attaaccaaggtcaccccagttatcggaggagcaaacaggggctaagtccaccgggggaggctgctg
gtgaatattaaccaaggtcaccccagttatcggaggagcaaacaggggctaagtccacaaatgacct
attaagaatatttcatagaacgaatgttccgatgctctaatctctctagacaaggttcatatttgta
tgggttacttattctctctttgttgactaagtcaataatcagaatcagcaggtttgcagtcagattg
gcagggataagcagcctagctcaggagaagtgagtataaaagccccaggctgggagcagccatcaca
gaagtccactcattcttggcaggggcgcgccgccaccatgcagattgagctgagcacctgcttcttc
ctgtgcctgctgaggttctgcttctctgccaccaggagatactacctgggggctgtggagctttctt
gggactacatgcagtctgacctgggggagctgcctgtggatgccaggttcccacccagagtgcccaa
atccttcccattcaacacctctgtggtctacaagaagaccctctttgtggagttcactgaccacctg
ttcaacattgccaaacccaggccaccctggatgggactcctgggacccaccattcaggctgaggtgt
atgacactgtggtcgtcaccctcaagaacatggcctcccaccctgtgagcctgcatgctgtggggt
cagctactggaagtcctctgagggggctgagtatgatgaccagacctcccagagggagaaggaggat
gacaaagtgttccctgggaagagccacacctatgtgtggcaggtcctcaaggagaatggccccactg
cctctgacccaccctgcctgacctactcctacctttctcatgtggacctggtcaaggacctcaactc
tggactgattggggccctgctggtgtgcagggagggctccctggccaaagagaagacccagaccctg
cacaagttcattctcctgtttgctgtctttgatgagggcaagagctggcactctgaaaccaagaact
ccctgatgcaggacagggatgctgcctctgccagggcctggcccaagatgcacactgtgaatggcta
tgtgaacaggagcctgcctggactcattggctgccacaggaaatctgtctactggcatgtgattggc
atggggacaacccctgaggtgcactccattttcctggagggccacaccttcctggtcaggaaccaca
gacaggccagcctggagatcagccccatcaccttcctcactgcccagaccctgctgatggacctcgg
acagttcctgctgttctgccacatcagctcccaccagcatgatggcatggaggcctatgtcaaggtg
gacagctgccctgaggagccacagctcaggatgaagaacaatgaggaggctgaggactatgatgatg
acctgactgactctgagatggatgtggtccgctttgatgatgacaacagcccatccttcattcagat
caggtctgtggccaagaaacaccccaagacctgggtgcactacattgctgctgaggaggaggactgg
gactatgccccactggtcctggcccctgatgacaggagctacaagagccagtacctcaacaatggcc
cacagaggattggacgcaagtacaagaaagtcaggttcatggcctacactgatgaaaccttcaagac (Continued)

Figure 20A cagggaggccattcagcatgagtctggcatcctgggcccactcctgtatggggaggtgggggacacc
ctgctcatcatcttcaagaaccaggcctccaggccctacaacatctacccacatggcatcactgatg
tcaggcccctgtacagccgcaggctgccaaaggggtgaaacacctcaaggacttccccattctgcc
tggggagatcttcaagtacaagtggactgtcactgtggaggatggaccaaccaaatctgaccccagg
tgcctcaccagatactactccagctttgtgaacatggagagggacctggcctctggcctgattggcc
cactgctcatctgctacaaggagtctgtggaccagaggggaaaccagatcatgtctgacaagaggaa
tgtgattctgttctctgtctttgatgagaacaggagctggtacctgactgagaacattcagcgcttc
ctgcccaaccctgctggggtgcagctggaggaccctgagttccaggccagcaacatcatgcactcca
tcaatggctatgtgtttgacagcctccagctttctgtctgcctgcatgaggtggcctactggtacat
tctttctattgggcccagactgacttcctttctgtcttcttctctggctacaccttcaaacacaag
atggtgtatgaggacaccctgaccctcttcccattctctggggagactgtgttcatgagcatggaga
accctggcctgtggattctgggatgccacaactctgacttccgcaacaggggcatgactgccctgct
caaagtctcctcctgtgacaagaacactggggactactatgaggacagctatgaggacatctctgcc
tacctgctcagcaagaacaatgccattgagcccaggagcttcagccagaatgtgagcaataatgcca
ccaacccacctgtcctgaaacgccaccagagggagatcaccaggaccaccctccagtctgaccagga
ggagattgactatgatgacaccatttctgtggagatgaagaaagaggactttgacatctatgacgag
gacgagaaccagagcccaaggagcttccagaagaagaccaggcactacttcattgctgctgtggagc
gcctgtgggactatggcatgagctccagccccatgtcctcaggaacagggcccagtctggctctgt
gccacagttcaagaaagtggtcttccaagagttcactgatggcagcttcacccagcccctgtacaga
ggggagctgaatgagcacctgggactcctgggcccatacatcagggctgaggtggaggacaacatca
tggtgaccttccgcaaccaggcctccaggccctacagcttctacagctccctcatcagctatgagga
ggaccagaggcaggggctgagccacgcaagaactttgtgaaacccaatgaaaccaagacctacttc
tggaaagtccagcaccacatggcccccaccaaggatgagtttgactgcaaggcctgggcctacttct
ctgatgtggacctggagaaggatgtgcactctggcctgattggcccactcctggtctgccacaccaa
caccctgaaccctgcccatggaaggcaagtgactgtgcaggagtttgccctcttcttcaccatcttt
gatgaaaccaagagctggtacttcactgagaacatggagcgcaactgcagggccccatgcaacattc
agatggaggaccccaccttcaaagagaactaccgcttccatgccatcaatggctacatcatggacac
cctgcctgggcttgtcatggcccaggaccagaggatcaggtggtacctgctttctatgggctccaat
gagaacattcactccatccacttctctgggcatgtcttcactgtgcgcaagaaggaggagtacaaga
tggccctgtacaacctctaccctggggtctttgagactgtggagatgctgccctccaaagctggcat
ctggagggtggagtgcctcattggggagcacctgcatgctggcatgagcaccctgttcctggtctac
agcaacaagtgccagacccccctgggaatggcctctggccacatcagggacttccagatcactgcct
ctggccagtatggccagtgggcccccaagctggccaggctccactactctggatccatcaatgcctg
gagcaccaaggagccattcagctggatcaaagtggacctgctggcccccatgatcatccatggcatc
aagacccaggggggccaggcagaagttctccagcctgtacatcagccagttcatcatcatgtacagcc
tggatggcaagaaatggcagacctacagaggcaactccactggaacactcatggtcttctttggcaa
tgtggacagctctggcatcaagcacaacatcttcaacccccccaatcatcgccagatacatcaggctg
caccccacccactacagcatccgcagcaccctcaggatggagctgatgggctgtgacctgaactcct
gcagcatgcccctgggcatggagagcaaggccatttctgatgcccagatcactgcctccagctactt
caccaacatgtttgccacctggagcccaagcaaggccaggctgcacctccagggaaggagcaatgcc
tggaggccccaggtcaacaacccaaaggagtggctgcaggtggacttccagaagaccatgaaggtca
ctggggtgaccacccagggggtcaagagcctgctcaccagcatgtatgtgaaggagttcctgatcag
ctccagccaggatggccaccagtggaccctcttcttccagaatggcaaggtcaaggtgttccagggc (Continued)

Figure 20B aaccaggacagcttcacccctgtggtgaacagcctggaccccccctcctgaccagatacctgagga
ttcacccccagagctgggtccaccagattgccctgaggatggaggtcctgggatgtgaggcccagga
cctgtactgatgagcggccgctcttagtagcagtatcgataataaaagatctttattttcattagat
ctgtgtgttggttttttgtgtgttaattaagctcgcgaaggaacccctagtgatggagttggccact
ccctctctgcgcgctcgctcgctcactgaggccgggcgaccaaaggtcgcccgacgcccgggctttg
cccgggcggcctcagtgagcgagcgagcgcgcagagagggagtggccaagacgatttaaatgacaag
cttggcgtaatcatggtcatagctgtttcctgtgtgaaattgttatccgctcacaattccacacaac
atacgagccggaagcataaagtgtaaagcctggggtgcctaatgagtgagctaactcacattaattg
cgttgcgctcactgcccgctttccagtcgggaaacctgtcgtgccagctgcattaatgaatcggcca
acgcgcggggagaggcggtttgcgtattgggcgctcttccgcttcctcgctcactgactcgctgcgc
tcggtcgttcggctgcggcgagcggtatcagctcactcaaaggcggtaatacggttatccacagaat
caggggataacgcaggaaagaacatgtgagcaaaaggccagcaaaaggccaggaaccgtaaaaaggc
cgcgttgctggcgtttttccataggctccgcccccctgacgagcatcacaaaaatcgacgctcaagt
cagaggtggcgaaacccgacaggactataaagataccaggcgtttccccctggaagctccctcgtgc
gctctcctgttccgaccctgccgcttaccggatacctgtccgcctttctcccttcgggaagcgtggc
gctttctcatagctcacgctgtaggtatctcagttcggtgtaggtcgttcgctccaagctgggctgt
gtgcacgaaccccccgttcagcccgaccgctgcgccttatccggtaactatcgtcttgagtccaacc
cggtaagacacgacttatcgccactggcagcagccactggtaacaggattagcagagcgaggtatgt
aggcggtgctacagagttcttgaagtggtggcctaactacggctacactagaagaacagtatttggt
atctgcgctctgctgaagccagttaccttcggaaaaagagttggtagctcttgatccggcaaacaaa
ccaccgctggtagcggtggtttttttgtttgcaagcagcagattacgcgcagaaaaaaaggatctca
agaagatcctttgatcttttctacggggtctgacgctcagtggaacgaaaactcacgttaagggatt
ttggtcatgagattatcaaaaaggatcttcacctagatccttttaaattaaaaatgaagttttaaat
caatctaaagtatatatgagtaaacttggtctgacagttaccaatgcttaatcagtgaggcacctat
ctcagcgatctgtctatttcgttcatccatagttgcctgactccccgtcgtgtagataactacgata
cgggagggcttaccatctggccccagtgctgcaatgataccgcgagacccacgctcaccggctccag
atttatcagcaataaaccagccagccggaagggccgagcgcagaagtggtcctgcaactttatccgc
ctccatccagtctattaattgttgccgggaagctagagtaagtagttcgccagttaatagtttgcgc
aacgttgttgccattgctacaggcatcgtggtgtcacgctcgtcgtttggtatggcttcattcagct
ccggttcccaacgatcaaggcgagttacatgatcccccatgttgtgcaaaaaagcggttagctcctt
cggtcctccgatcgttgtcagaagtaagttggccgcagtgttatcactcatggttatggcagcactg
cataattctcttactgtcatgccatccgtaagatgcttttctgtgactggtgagtactcaaccaagt
cattctgagaatagtgtatgcggcgaccgagttgctcttgcccggcgtcaatacgggataataccgc
gccacatagcagaactttaaaagtgctcatcattggaaaacgttcttcggggcgaaaactctcaagg
atcttaccgctgttgagatccagttcgatgtaacccactcgtgcacccaactgatcttcagcatctt
ttactttcaccagcgtttctgggtgagcaaaaacaggaaggcaaaatgccgcaaaaaagggaataag
ggcgacacggaaatgttgaatactcatactcttcctttttcaatattattgaagcatttatcagggt
tattgtctcatgagcggatacatatttgaatgtatttagaaaaataaacaaataggggttccgcgca
catttccccgaaaagtgccacctgacgtctaagaaaccattattatcatgacattaacctataaaaa
taggcgtatcacgaggccctttcgtc (SEQ ID NO:57)

Figure 20C

SEQUENCE LISTING

<160> NUMBER OF SEQ ID NOS: 57

<210> SEQ ID NO 1
<211> LENGTH: 4392
<212> TYPE: DNA
<213> ORGANISM: Artificial Sequence
<220> FEATURE:
<223> OTHER INFORMATION: Synthetic

<400> SEQUENCE: 1

```
atgcagattg agctgagcac ctgcttcttc ctgtgcctgc tgaggttctg cttctctgcc     60

accaggagat actacctggg ggctgtggag ctttcttggg actacatgca gtctgacctg    120

ggggagctgc ctgtggatgc caggttccca cccagagtgc ccaaatcctt cccattcaac    180

acctctgtgg tctacaagaa gaccctcttt gtggagttca ctgaccacct gttcaacatt    240

gccaaaccca ggccaccctg gatgggactc ctgggaccca ccattcaggc tgaggtgtat    300

gacactgtgg tcgtcaccct caagaacatg gcctcccacc ctgtgagcct gcatgctgtg    360

ggggtcagct actggaagtc ctctgagggg gctgagtatg atgaccagac ctcccagagg    420

gagaaggagg atgacaaagt gttccctggg aagagccaca cctatgtgtg gcaggtcctc    480

aaggagaatg gccccactgc ctctgaccca ccctgcctga cctactccta cctttctcat    540

gtggacctgg tcaaggacct caactctgga ctgattgggg ccctgctggt gtgcagggag    600

ggctccctgg ccaaagagaa gacccagacc ctgcacaagt tcattctcct gtttgctgtc    660

tttgatgagg gcaagagctg gcactctgaa accaagaact ccctgatgca ggacagggat    720

gctgcctctg ccagggcctg gcccaagatg cacactgtga atggctatgt gaacaggagc    780

ctgcctggac tcattggctg ccacaggaaa tctgtctact ggcatgtgat tggcatgggg    840

acaacccctg aggtgcactc cattttcctg gagggccaca ccttcctggt caggaaccac    900

agacaggcca gcctggagat cagccccatc accttcctca ctgcccagac cctgctgatg    960

gacctcggac agttcctgct gttctgccac atcagctccc accagcatga tggcatggag   1020

gcctatgtca aggtggacag ctgccctgag gagccacagc tcaggatgaa gaacaatgag   1080

gaggctgagg actatgatga tgacctgact gactctgaga tggatgtggt ccgctttgat   1140

gatgacaaca gcccatcctt cattcagatc aggtctgtgg ccaagaaaca ccccaagacc   1200

tgggtgcact acattgctgc tgaggaggag gactgggact atgccccact ggtcctggcc   1260

cctgatgaca ggagctacaa gagccagtac ctcaacaatg gcccacagag gattggacgc   1320

aagtacaaga aagtcaggtt catggcctac actgatgaaa ccttcaagac cagggaggcc   1380

attcagcatg agtctggcat cctgggccca ctcctgtatg gggaggtggg ggacaccctg   1440

ctcatcatct tcaagaacca ggcctccagg ccctacaaca tctacccaca tggcatcact   1500

gatgtcaggc ccctgtacag ccgcaggctg ccaaaggggg tgaaacacct caaggacttc   1560

cccattctgc ctggggagat cttcaagtac aagtggactg tcactgtgga ggatggacca   1620

accaaatctg accccaggtg cctcaccaga tactactcca gctttgtgaa catggagagg   1680

gacctggcct ctggcctgat tggcccactg ctcatctgct acaaggagtc tgtggaccag   1740

aggggaaacc agatcatgtc tgacaagagg aatgtgattc tgttctctgt ctttgatgag   1800

aacaggagct ggtacctgac tgagaacatt cagcgcttcc tgcccaaccc tgctggggtg   1860

cagctggagg accctgagtt ccaggccagc aacatcatgc actccatcaa tggctatgtg   1920

tttgacagcc tccagctttc tgtctgcctg catgaggtgg cctactggta cattctttct   1980

attggggccc agactgactt cctttctgtc ttcttctctg gctacacctt caaacacaag   2040
```

```
atggtgtatg aggacaccct gaccctcttc ccattctctg ggagactgt gttcatgagc   2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca atgccattga gcccaggagc   2280
ttcagccaga atgtgagcaa taatgccacc aacccacctg tcctgaaacg ccaccagagg   2340
gagatcacca ggaccaccct ccagtctgac caggaggaga ttgactatga tgacaccatt   2400
tctgtggaga tgaagaaaga ggactttgac atctatgacg aggacgagaa ccagagccca   2460
aggagcttcc agaagaagac caggcactac ttcattgctg ctgtggagcg cctgtgggac   2520
tatggcatga gctccagccc ccatgtcctc aggaacaggg cccagtctgg ctctgtgcca   2580
cagttcaaga aagtggtctt ccaagagttc actgatggca gcttcaccca gcccctgtac   2640
agaggggagc tgaatgagca cctgggactc ctgggcccat acatcagggc tgaggtggag   2700
gacaacatca tggtgacctt ccgcaaccag gcctccaggc cctacagctt ctacagctcc   2760
ctcatcagct atgaggagga ccagaggcag gggggctgagc cacgcaagaa ctttgtgaaa   2820
cccaatgaaa ccaagaccta cttctggaaa gtccagcacc acatggcccc caccaaggat   2880
gagtttgact gcaaggcctg ggcctacttc tctgatgtgg acctggagaa ggatgtgcac   2940
tctggcctga ttggcccact cctggtctgc cacaccaaca ccctgaaccc tgcccatgga   3000
aggcaagtga ctgtgcagga gtttgccctc ttcttcacca tctttgatga aaccaagagc   3060
tggtacttca ctgagaacat ggagcgcaac tgcagggccc catgcaacat tcagatggag   3120
gaccccacct tcaaagagaa ctaccgcttc catgccatca atggctacat catggacacc   3180
ctgcctgggc ttgtcatggc ccaggaccag aggatcaggt ggtacctgct ttctatgggc   3240
tccaatgaga acattcactc catccacttc tctgggcatg tcttcactgt gcgcaagaag   3300
gaggagtaca agatggccct gtacaacctc taccctgggg tctttgagac tgtggagatg   3360
ctgccctcca aagctggcat ctggagggtg gagtgcctca ttggggagca cctgcatgct   3420
ggcatgagca ccctgttcct ggtctacagc aacaagtgcc agaccccccct gggaatggcc   3480
tctggccaca tcagggactt ccagatcact gcctctggcc agtatggcca gtgggccccc   3540
aagctggcca ggctccacta ctctggatcc atcaatgcct ggagcaccaa ggagccattc   3600
agctggatca aagtggacct gctggccccc atgatcatcc atggcatcaa gacccagggg   3660
gccaggcaga agttctccag cctgtacatc agccagttca tcatcatgta cagcctggat   3720
ggcaagaaat ggcagaccta cagaggcaac tccactggaa cactcatggt cttctttggc   3780
aatgtggaca gctctggcat caagcacaac atcttcaacc ccccaatcat cgccagatac   3840
atcaggctgc accccaccca ctacagcatc cgcagcaccc tcaggatgga gctgatgggc   3900
tgtgacctga actcctgcag catgcccctg ggcatggaga gcaaggccat ttctgatgcc   3960
cagatcactg cctccagcta cttcaccaac atgtttgcca cctggagccc aagcaaggcc   4020
aggctgcacc tccagggaag gagcaatgcc tggaggcccc aggtcaacaa cccaaaggag   4080
tggctgcagg tggacttcca gaagaccatg aaggtcactg gggtgaccac ccagggggtc   4140
aagagcctgc tcaccagcat gtatgtgaag gagttcctga tcagctccag ccaggatggc   4200
caccagtgga ccctcttctt ccagaatggc aaggtcaagg tgttccaggg caaccaggac   4260
agcttcaccc ctgtggtgaa cagcctggac ccccccctcc tgaccagata cctgaggatt   4320
cacccccaga gctgggtcca ccagattgcc ctgaggatgg aggtcctggg atgtgaggcc   4380
```

caggacctgt ac 4392

<210> SEQ ID NO 2
<211> LENGTH: 1470
<212> TYPE: PRT
<213> ORGANISM: Artificial Sequence
<220> FEATURE:
<223> OTHER INFORMATION: Synthetic

<400> SEQUENCE: 2

```
Cys Ser Phe Leu Ala Ala Met Gln Ile Glu Leu Ser Thr Cys Phe Phe
1               5                   10                  15

Leu Cys Leu Leu Arg Phe Cys Phe Ser Ala Thr Arg Arg Tyr Tyr Leu
            20                  25                  30

Gly Ala Val Glu Leu Ser Trp Asp Tyr Met Gln Ser Asp Leu Gly Glu
        35                  40                  45

Leu Pro Val Asp Ala Arg Phe Pro Pro Arg Val Pro Lys Ser Phe Pro
    50                  55                  60

Phe Asn Thr Ser Val Val Tyr Lys Lys Thr Leu Phe Val Glu Phe Thr
65                  70                  75                  80

Asp His Leu Phe Asn Ile Ala Lys Pro Arg Pro Pro Trp Met Gly Leu
                85                  90                  95

Leu Gly Pro Thr Ile Gln Ala Glu Val Tyr Asp Thr Val Val Val Thr
            100                 105                 110

Leu Lys Asn Met Ala Ser His Pro Val Ser Leu His Ala Val Gly Val
        115                 120                 125

Ser Tyr Trp Lys Ser Ser Glu Gly Ala Glu Tyr Asp Asp Gln Thr Ser
    130                 135                 140

Gln Arg Glu Lys Glu Asp Asp Lys Val Phe Pro Gly Lys Ser His Thr
145                 150                 155                 160

Tyr Val Trp Gln Val Leu Lys Glu Asn Gly Pro Thr Ala Ser Asp Pro
                165                 170                 175

Pro Cys Leu Thr Tyr Ser Tyr Leu Ser His Val Asp Leu Val Lys Asp
            180                 185                 190

Leu Asn Ser Gly Leu Ile Gly Ala Leu Leu Val Cys Arg Glu Gly Ser
        195                 200                 205

Leu Ala Lys Glu Lys Thr Gln Thr Leu His Lys Phe Ile Leu Leu Phe
    210                 215                 220

Ala Val Phe Asp Glu Gly Lys Ser Trp His Ser Glu Thr Lys Asn Ser
225                 230                 235                 240

Leu Met Gln Asp Arg Asp Ala Ala Ser Ala Arg Ala Trp Pro Lys Met
                245                 250                 255

His Thr Val Asn Gly Tyr Val Asn Arg Ser Leu Pro Gly Leu Ile Gly
            260                 265                 270

Cys His Arg Lys Ser Val Tyr Trp His Val Ile Gly Met Gly Thr Thr
        275                 280                 285

Pro Glu Val His Ser Ile Phe Leu Glu Gly His Thr Phe Leu Val Arg
    290                 295                 300

Asn His Arg Gln Ala Ser Leu Glu Ile Ser Pro Ile Thr Phe Leu Thr
305                 310                 315                 320

Ala Gln Thr Leu Leu Met Asp Leu Gly Gln Phe Leu Leu Phe Cys His
                325                 330                 335

Ile Ser Ser His Gln His Asp Gly Met Glu Ala Tyr Val Lys Val Asp
            340                 345                 350

Ser Cys Pro Glu Glu Pro Gln Leu Arg Met Lys Asn Asn Glu Glu Ala
```

```
        355                 360                 365

Glu Asp Tyr Asp Asp Asp Leu Thr Asp Ser Glu Met Asp Val Val Arg
    370                 375                 380

Phe Asp Asp Asp Asn Ser Pro Ser Phe Ile Gln Ile Arg Ser Val Ala
385                 390                 395                 400

Lys Lys His Pro Lys Thr Trp Val His Tyr Ile Ala Ala Glu Glu Glu
                405                 410                 415

Asp Trp Asp Tyr Ala Pro Leu Val Leu Ala Pro Asp Asp Arg Ser Tyr
            420                 425                 430

Lys Ser Gln Tyr Leu Asn Asn Gly Pro Gln Arg Ile Gly Arg Lys Tyr
        435                 440                 445

Lys Lys Val Arg Phe Met Ala Tyr Thr Asp Glu Thr Phe Lys Thr Arg
    450                 455                 460

Glu Ala Ile Gln His Glu Ser Gly Ile Leu Gly Pro Leu Leu Tyr Gly
465                 470                 475                 480

Glu Val Gly Asp Thr Leu Leu Ile Ile Phe Lys Asn Gln Ala Ser Arg
                485                 490                 495

Pro Tyr Asn Ile Tyr Pro His Gly Ile Thr Asp Val Arg Pro Leu Tyr
            500                 505                 510

Ser Arg Arg Leu Pro Lys Gly Val Lys His Leu Lys Asp Phe Pro Ile
        515                 520                 525

Leu Pro Gly Glu Ile Phe Lys Tyr Lys Trp Thr Val Thr Val Glu Asp
    530                 535                 540

Gly Pro Thr Lys Ser Asp Pro Arg Cys Leu Thr Arg Tyr Tyr Ser Ser
545                 550                 555                 560

Phe Val Asn Met Glu Arg Asp Leu Ala Ser Gly Leu Ile Gly Pro Leu
                565                 570                 575

Leu Ile Cys Tyr Lys Glu Ser Val Asp Gln Arg Gly Asn Gln Ile Met
            580                 585                 590

Ser Asp Lys Arg Asn Val Ile Leu Phe Ser Val Phe Asp Glu Asn Arg
        595                 600                 605

Ser Trp Tyr Leu Thr Glu Asn Ile Gln Arg Phe Leu Pro Asn Pro Ala
    610                 615                 620

Gly Val Gln Leu Glu Asp Pro Glu Phe Gln Ala Ser Asn Ile Met His
625                 630                 635                 640

Ser Ile Asn Gly Tyr Val Phe Asp Ser Leu Gln Leu Ser Val Cys Leu
                645                 650                 655

His Glu Val Ala Tyr Trp Tyr Ile Leu Ser Ile Gly Ala Gln Thr Asp
            660                 665                 670

Phe Leu Ser Val Phe Phe Ser Gly Tyr Thr Phe Lys His Lys Met Val
        675                 680                 685

Tyr Glu Asp Thr Leu Thr Leu Phe Pro Phe Ser Gly Glu Thr Val Phe
    690                 695                 700

Met Ser Met Glu Asn Pro Gly Leu Trp Ile Leu Gly Cys His Asn Ser
705                 710                 715                 720

Asp Phe Arg Asn Arg Gly Met Thr Ala Leu Leu Lys Val Ser Ser Cys
                725                 730                 735

Asp Lys Asn Thr Gly Asp Tyr Tyr Glu Asp Ser Tyr Glu Asp Ile Ser
            740                 745                 750

Ala Tyr Leu Leu Ser Lys Asn Asn Ala Ile Glu Pro Arg Ser Phe Ser
        755                 760                 765

Gln Asn Val Ser Asn Asn Ala Thr Asn Pro Pro Val Leu Lys Arg His
    770                 775                 780
```

```
Gln Arg Glu Ile Thr Arg Thr Thr Leu Gln Ser Asp Gln Glu Glu Ile
785                 790                 795                 800

Asp Tyr Asp Asp Thr Ile Ser Val Glu Met Lys Lys Glu Asp Phe Asp
                805                 810                 815

Ile Tyr Asp Glu Asp Glu Asn Gln Ser Pro Arg Ser Phe Gln Lys Lys
            820                 825                 830

Thr Arg His Tyr Phe Ile Ala Ala Val Glu Arg Leu Trp Asp Tyr Gly
        835                 840                 845

Met Ser Ser Ser Pro His Val Leu Arg Asn Arg Ala Gln Ser Gly Ser
    850                 855                 860

Val Pro Gln Phe Lys Lys Val Val Phe Gln Glu Phe Thr Asp Gly Ser
865                 870                 875                 880

Phe Thr Gln Pro Leu Tyr Arg Gly Glu Leu Asn Glu His Leu Gly Leu
                885                 890                 895

Leu Gly Pro Tyr Ile Arg Ala Glu Val Glu Asp Asn Ile Met Val Thr
            900                 905                 910

Phe Arg Asn Gln Ala Ser Arg Pro Tyr Ser Phe Tyr Ser Ser Leu Ile
        915                 920                 925

Ser Tyr Glu Glu Asp Gln Arg Gln Gly Ala Glu Pro Arg Lys Asn Phe
    930                 935                 940

Val Lys Pro Asn Glu Thr Lys Thr Tyr Phe Trp Lys Val Gln His His
945                 950                 955                 960

Met Ala Pro Thr Lys Asp Glu Phe Asp Cys Lys Ala Trp Ala Tyr Phe
                965                 970                 975

Ser Asp Val Asp Leu Glu Lys Asp Val His Ser Gly Leu Ile Gly Pro
            980                 985                 990

Leu Leu Val Cys His Thr Asn Thr  Leu Asn Pro Ala His  Gly Arg Gln
        995                 1000                 1005

Val Thr  Val Gln Glu Phe Ala  Leu Phe Phe Thr Ile  Phe Asp Glu
    1010                 1015                 1020

Thr Lys  Ser Trp Tyr Phe Thr  Glu Asn Met Glu Arg  Asn Cys Arg
    1025                 1030                 1035

Ala Pro  Cys Asn Ile Gln Met  Glu Asp Pro Thr Phe  Lys Glu Asn
    1040                 1045                 1050

Tyr Arg  Phe His Ala Ile Asn  Gly Tyr Ile Met Asp  Thr Leu Pro
    1055                 1060                 1065

Gly Leu  Val Met Ala Gln Asp  Gln Arg Ile Arg Trp  Tyr Leu Leu
    1070                 1075                 1080

Ser Met  Gly Ser Asn Glu Asn  Ile His Ser Ile His  Phe Ser Gly
    1085                 1090                 1095

His Val  Phe Thr Val Arg Lys  Lys Glu Glu Tyr Lys  Met Ala Leu
    1100                 1105                 1110

Tyr Asn  Leu Tyr Pro Gly Val  Phe Glu Thr Val Glu  Met Leu Pro
    1115                 1120                 1125

Ser Lys  Ala Gly Ile Trp Arg  Val Glu Cys Leu Ile  Gly Glu His
    1130                 1135                 1140

Leu His  Ala Gly Met Ser Thr  Leu Phe Leu Val Tyr  Ser Asn Lys
    1145                 1150                 1155

Cys Gln  Thr Pro Leu Gly Met  Ala Ser Gly His Ile  Arg Asp Phe
    1160                 1165                 1170

Gln Ile  Thr Ala Ser Gly Gln  Tyr Gly Gln Trp Ala  Pro Lys Leu
    1175                 1180                 1185
```

```
Ala Arg  Leu His Tyr Ser Gly  Ser Ile Asn Ala Trp  Ser Thr Lys
    1190                 1195                 1200

Glu Pro  Phe Ser Trp Ile Lys  Val Asp Leu Leu Ala  Pro Met Ile
    1205                 1210                 1215

Ile His  Gly Ile Lys Thr Gln  Gly Ala Arg Gln Lys  Phe Ser Ser
    1220                 1225                 1230

Leu Tyr  Ile Ser Gln Phe Ile  Ile Met Tyr Ser Leu  Asp Gly Lys
    1235                 1240                 1245

Lys Trp  Gln Thr Tyr Arg Gly  Asn Ser Thr Gly Thr  Leu Met Val
    1250                 1255                 1260

Phe Phe  Gly Asn Val Asp Ser  Ser Gly Ile Lys His  Asn Ile Phe
    1265                 1270                 1275

Asn Pro  Pro Ile Ile Ala Arg  Tyr Ile Arg Leu His  Pro Thr His
    1280                 1285                 1290

Tyr Ser  Ile Arg Ser Thr Leu  Arg Met Glu Leu Met  Gly Cys Asp
    1295                 1300                 1305

Leu Asn  Ser Cys Ser Met Pro  Leu Gly Met Glu Ser  Lys Ala Ile
    1310                 1315                 1320

Ser Asp  Ala Gln Ile Thr Ala  Ser Ser Tyr Phe Thr  Asn Met Phe
    1325                 1330                 1335

Ala Thr  Trp Ser Pro Ser Lys  Ala Arg Leu His Leu  Gln Gly Arg
    1340                 1345                 1350

Ser Asn  Ala Trp Arg Pro Gln  Val Asn Asn Pro Lys  Glu Trp Leu
    1355                 1360                 1365

Gln Val  Asp Phe Gln Lys Thr  Met Lys Val Thr Gly  Val Thr Thr
    1370                 1375                 1380

Gln Gly  Val Lys Ser Leu Leu  Thr Ser Met Tyr Val  Lys Glu Phe
    1385                 1390                 1395

Leu Ile  Ser Ser Ser Gln Asp  Gly His Gln Trp Thr  Leu Phe Phe
    1400                 1405                 1410

Gln Asn  Gly Lys Val Lys Val  Phe Gln Gly Asn Gln  Asp Ser Phe
    1415                 1420                 1425

Thr Pro  Val Val Asn Ser Leu  Asp Pro Pro Leu Leu  Thr Arg Tyr
    1430                 1435                 1440

Leu Arg  Ile His Pro Gln Ser  Trp Val His Gln Ile  Ala Leu Arg
    1445                 1450                 1455

Met Glu  Val Leu Gly Cys Glu  Ala Gln Asp Leu Tyr
    1460                 1465                 1470
```

<210> SEQ ID NO 3
<211> LENGTH: 5120
<212> TYPE: DNA
<213> ORGANISM: Artificial Sequence
<220> FEATURE:
<223> OTHER INFORMATION: Synthetic

<400> SEQUENCE: 3

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggggg aggctgctgg tgaatattaa ccaaggtcac    180

cccagttatc ggaggagcaa acaggggcta agtccaccgg gggaggctgc tggtgaatat    240

taaccaaggt caccccagtt atcggaggag caaacagggg ctaagtccac aaatgaccta    300

ttaagaatat ttcatagaac gaatgttccg atgctctaat ctctctagac aaggttcata    360
```

```
tttgtatggg ttacttattc tctctttgtt gactaagtca ataatcagaa tcagcaggtt    420
tgcagtcaga ttggcaggga taagcagcct agctcaggag aagtgagtat aaaagcccca    480
ggctgggagc agccatcaca gaagtccact cattcttggc aggccaccat gcagattgag    540
ctgagcacct gcttcttcct gtgcctgctg aggttctgct tctctgccac caggagatac    600
tacctggggg ctgtggagct ttcttgggac tacatgcagt ctgacctggg ggagctgcct    660
gtggatgcca ggttcccacc cagagtgccc aaatccttcc cattcaacac ctctgtggtc    720
tacaagaaga ccctctttgt ggagttcact gaccacctgt tcaacattgc caaacccagg    780
ccaccctgga tgggactcct gggacccacc attcaggctg aggtgtatga cactgtggtc    840
gtcaccctca agaacatggc ctcccaccct gtgagcctgc atgctgtggg ggtcagctac    900
tggaagtcct ctgagggggc tgagtatgat gaccagacct cccagaggga gaaggaggat    960
gacaaagtgt tccctgggaa gagccacacc tatgtgtggc aggtcctcaa ggagaatggc   1020
cccactgcct ctgacccacc ctgcctgacc tactcctacc tttctcatgt ggacctggtc   1080
aaggacctca actctggact gattggggcc ctgctggtgt gcagggaggg ctccctggcc   1140
aaagagaaga cccagaccct gcacaagttc attctcctgt ttgctgtctt tgatgagggc   1200
aagagctggc actctgaaac caagaactcc ctgatgcagg acagggatgc tgcctctgcc   1260
agggcctggc ccaagatgca cactgtgaat ggctatgtga acaggagcct gcctggactc   1320
attggctgcc acaggaaatc tgtctactgg catgtgattg gcatggggac aacccctgag   1380
gtgcactcca ttttcctgga gggccacacc ttcctggtca ggaaccacag acaggccagc   1440
ctggagatca gccccatcac cttcctcact gcccagaccc tgctgatgga cctcggacag   1500
ttcctgctgt tctgccacat cagctcccac cagcatgatg gcatggaggc ctatgtcaag   1560
gtggacagct gccctgagga gccacagctc aggatgaaga acaatgagga ggctgaggac   1620
tatgatgatg acctgactga ctctgagatg gatgtggtcc gctttgatga tgacaacagc   1680
ccatccttca ttcagatcag gtctgtggcc aagaaacacc ccaagacctg ggtgcactac   1740
attgctgctg aggaggagga ctgggactat gccccactgg tcctggcccc tgatgacagg   1800
agctacaaga gccagtacct caacaatggc ccacagagga ttggacgcaa gtacaagaaa   1860
gtcaggttca tggcctacac tgatgaaacc ttcaagacca gggaggccat tcagcatgag   1920
tctggcatcc tgggcccact cctgtatggg gaggtggggg acaccctgct catcatcttc   1980
aagaaccagg cctccaggcc ctacaacatc tacccacatg gcatcactga tgtcaggccc   2040
ctgtacagcc gcaggctgcc aaagggggtg aaacacctca aggacttccc cattctgcct   2100
ggggagatct tcaagtacaa gtggactgtc actgtggagg atggaccaac caaatctgac   2160
cccaggtgcc tcaccagata ctactccagc tttgtgaaca tggagaggga cctggcctct   2220
ggcctgattg gcccactgct catctgctac aaggagtctg tggaccagag gggaaaccag   2280
atcatgtctg acaagaggaa tgtgattctg ttctctgtct ttgatgagaa caggagctgg   2340
tacctgactg agaacattca gcgcttcctg cccaaccctg ctggggtgca gctggaggac   2400
cctgagttcc aggccagcaa catcatgcac tccatcaatg gctatgtgtt tgacagcctc   2460
cagctttctg tctgcctgca tgaggtggcc tactggtaca ttctttctat tggggcccag   2520
actgacttcc tttctgtctt cttctctggc tacaccttca aacacaagat ggtgtatgag   2580
gacaccctga ccctcttccc attctctggg gagactgtgt tcatgagcat ggagaaccct   2640
ggcctgtgga ttctgggatg ccacaactct gacttccgca acaggggcat gactgccctg   2700
ctcaaagtct cctcctgtga caagaacact ggggactact atgaggacag ctatgaggac   2760
```

```
atctctgcct acctgctcag caagaacaat gccattgagc ccaggagctt cagccagaat   2820
gtgagcaata atgccaccaa cccacctgtc ctgaaacgcc accagaggga gatcaccagg   2880
accaccctcc agtctgacca ggaggagatt gactatgatg acaccatttc tgtggagatg   2940
aagaaagagg actttgacat ctatgacgag gacgagaacc agagcccaag gagcttccag   3000
aagaagacca ggcactactt cattgctgct gtggagcgcc tgtgggacta tggcatgagc   3060
tccagccccc atgtcctcag gaacagggcc cagtctggct ctgtgccaca gttcaagaaa   3120
gtggtcttcc aagagttcac tgatggcagc ttcacccagc ccctgtacag aggggagctg   3180
aatgagcacc tgggactcct gggcccatac atcagggctg aggtggagga caacatcatg   3240
gtgaccttcc gcaaccaggc ctccaggccc tacagcttct acagctccct catcagctat   3300
gaggaggacc agaggcaggg ggctgagcca cgcaagaact ttgtgaaacc caatgaaacc   3360
aagacctact tctggaaagt ccagcaccac atggccccca ccaaggatga gtttgactgc   3420
aaggcctggg cctacttctc tgatgtggac ctggagaagg atgtgcactc tggcctgatt   3480
ggcccactcc tggtctgcca caccaacacc ctgaaccctg cccatggaag gcaagtgact   3540
gtgcaggagt ttgccctctt cttcaccatc tttgatgaaa ccaagagctg gtacttcact   3600
gagaacatgg agcgcaactg cagggcccca tgcaacattc agatggagga ccccaccttc   3660
aaagagaact accgcttcca tgccatcaat ggctacatca tggacaccct gcctgggctt   3720
gtcatggccc aggaccagag gatcaggtgg tacctgcttt ctatgggctc caatgagaac   3780
attcactcca tccacttctc tgggcatgtc ttcactgtgc gcaagaagga ggagtacaag   3840
atggccctgt acaacctcta ccctggggtc tttgagactg tggagatgct gccctccaaa   3900
gctggcatct ggagggtgga gtgcctcatt ggggagcacc tgcatgctgg catgagcacc   3960
ctgttcctgg tctacagcaa caagtgccag accccccctgg gaatggcctc tggccacatc   4020
agggacttcc agatcactgc ctctggccag tatggccagt gggcccccaa gctggccagg   4080
ctccactact ctggatccat caatgcctgg agcaccaagg agccattcag ctggatcaaa   4140
gtggacctgc tggcccccat gatcatccat ggcatcaaga cccagggggc caggcagaag   4200
ttctccagcc tgtacatcag ccagttcatc atcatgtaca gcctggatgg caagaaatgg   4260
cagacctaca gaggcaactc cactggaaca ctcatggtct tctttggcaa tgtggacagc   4320
tctggcatca agcacaacat cttcaacccc ccaatcatcg ccagatacat caggctgcac   4380
cccacccact acagcatccg cagcaccctc aggatggagc tgatgggctg tgacctgaac   4440
tcctgcagca tgcccctggg catggagagc aaggccattt ctgatgccca gatcactgcc   4500
tccagctact tcaccaacat gtttgccacc tggagcccaa gcaaggccag gctgcacctc   4560
cagggaagga gcaatgcctg gaggccccag gtcaacaacc caaaggagtg gctgcaggtg   4620
gacttccaga agaccatgaa ggtcactggg gtgaccaccc agggggtcaa gagcctgctc   4680
accagcatgt atgtgaagga gttcctgatc agctccagcc aggatggcca ccagtggacc   4740
ctcttcttcc agaatggcaa ggtcaaggtg ttccagggca accaggacag cttcacccct   4800
gtggtgaaca gcctggaccc ccccctcctg accagatacc tgaggattca cccccagagc   4860
tgggtccacc agattgccct gaggatggag gtcctgggat gtgaggccca ggacctgtac   4920
tgatgaaata aaagatcttt attttcatta gatctgtgtg ttggtttttt gtgtgaggaa   4980
cccctagtga tggagttggc cactccctct ctgcgcgctc gctcgctcac tgaggccggg   5040
cgaccaaagg tcgcccgacg cccgggcttt gcccgggcgg cctcagtgag cgagcgagcg   5100
```

cgcagagagg gagtggccaa 5120

<210> SEQ ID NO 4
<211> LENGTH: 145
<212> TYPE: DNA
<213> ORGANISM: Artificial Sequence
<220> FEATURE:
<223> OTHER INFORMATION: Synthetic

<400> SEQUENCE: 4
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcct 145

<210> SEQ ID NO 5
<211> LENGTH: 72
<212> TYPE: DNA
<213> ORGANISM: Artificial Sequence
<220> FEATURE:
<223> OTHER INFORMATION: Synthetic

<400> SEQUENCE: 5
gggggaggct gctggtgaat attaaccaag gtcaccccag ttatcggagg agcaaacagg 60
ggctaagtcc ac 72

<210> SEQ ID NO 6
<211> LENGTH: 233
<212> TYPE: DNA
<213> ORGANISM: Artificial Sequence
<220> FEATURE:
<223> OTHER INFORMATION: Synthetic

<400> SEQUENCE: 6
aaatgaccta ttaagaatat ttcatagaac gaatgttccg atgctctaat ctctctagac 60
aaggttcata tttgtatggg ttacttattc tctctttgtt gactaagtca ataatcagaa 120
tcagcaggtt tgcagtcaga ttggcaggga taagcagcct agctcaggag aagtgagtat 180
aaaagcccca ggctgggagc agccatcaca gaagtccact cattcttggc agg 233

<210> SEQ ID NO 7
<211> LENGTH: 5
<212> TYPE: DNA
<213> ORGANISM: Artificial Sequence
<220> FEATURE:
<223> OTHER INFORMATION: Synthetic

<400> SEQUENCE: 7 ccacc 5

<210> SEQ ID NO 8
<211> LENGTH: 49
<212> TYPE: DNA
<213> ORGANISM: Artificial Sequence
<220> FEATURE:
<223> OTHER INFORMATION: Synthetic

<400> SEQUENCE: 8
aataaaagat ctttattttc attagatctg tgtgttggtt ttttgtgtg 49

<210> SEQ ID NO 9
<211> LENGTH: 145
<212> TYPE: DNA
<213> ORGANISM: Artificial Sequence

```
<220> FEATURE:
<223> OTHER INFORMATION: Synthetic

<400> SEQUENCE: 9

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag agagggagtg gccaa                                          145


<210> SEQ ID NO 10
<211> LENGTH: 7794
<212> TYPE: DNA
<213> ORGANISM: Artificial Sequence
<220> FEATURE:
<223> OTHER INFORMATION: Synthetic

<400> SEQUENCE: 10

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggggg aggctgctgg tgaatattaa ccaaggtcac    180

cccagttatc ggaggagcaa acaggggcta agtccaccgg gggaggctgc tggtgaatat    240

taaccaaggt caccccagtt atcggaggag caaacagggg ctaagtccac aaatgaccta    300

ttaagaatat ttcatagaac gaatgttccg atgctctaat ctctctagac aaggttcata    360

tttgtatggg ttacttattc tctctttgtt gactaagtca ataatcagaa tcagcaggtt    420

tgcagtcaga ttggcaggga taagcagcct agctcaggag aagtgagtat aaaagcccca    480

ggctgggagc agccatcaca gaagtccact cattcttggc aggccaccat gcagattgag    540

ctgagcacct gcttcttcct gtgcctgctg aggttctgct tctctgccac caggagatac    600

tacctggggg ctgtggagct ttcttgggac tacatgcagt ctgacctggg ggagctgcct    660

gtggatgcca ggttcccacc cagagtgccc aaatccttcc cattcaacac ctctgtggtc    720

tacaagaaga ccctctttgt ggagttcact gaccacctgt tcaacattgc caaacccagg    780

ccaccctgga tgggactcct gggacccacc attcaggctg aggtgtatga cactgtggtc    840

gtcaccctca agaacatggc ctcccaccct gtgagcctgc atgctgtggg ggtcagctac    900

tggaagtcct ctgagggggc tgagtatgat gaccagacct cccagaggga gaaggaggat    960

gacaaagtgt tccctgggaa gagccacacc tatgtgtggc aggtcctcaa ggagaatggc   1020

cccactgcct ctgacccacc ctgcctgacc tactcctacc tttctcatgt ggacctggtc   1080

aaggacctca actctggact gattggggcc ctgctggtgt gcagggaggg ctccctggcc   1140

aaagagaaga cccagaccct gcacaagttc attctcctgt ttgctgtctt tgatgagggc   1200

aagagctggc actctgaaac caagaactcc ctgatgcagg acagggatgc tgcctctgcc   1260

agggcctggc ccaagatgca cactgtgaat ggctatgtga acaggagcct gcctggactc   1320

attggctgcc acaggaaatc tgtctactgg catgtgattg gcatggggac aacccctgag   1380

gtgcactcca ttttcctgga gggccacacc ttcctggtca ggaaccacag acaggccagc   1440

ctggagatca gccccatcac cttcctcact gcccagaccc tgctgatgga cctcggacag   1500

ttcctgctgt tctgccacat cagctcccac cagcatgatg gcatggaggc ctatgtcaag   1560

gtggacagct gccctgagga gccacagctc aggatgaaga acaatgagga ggctgaggac   1620

tatgatgatg acctgactga ctctgagatg gatgtggtcc gctttgatga tgacaacagc   1680

ccatccttca ttcagatcag gtctgtggcc aagaaacacc ccaagacctg ggtgcactac   1740
```

-continued

```
attgctgctg aggaggagga ctgggactat gccccactgg tcctggcccc tgatgacagg   1800
agctacaaga gccagtacct caacaatggc ccacagagga ttggacgcaa gtacaagaaa   1860
gtcaggttca tggcctacac tgatgaaacc ttcaagacca gggaggccat tcagcatgag   1920
tctggcatcc tgggcccact cctgtatggg gaggtggggg acaccctgct catcatcttc   1980
aagaaccagg cctccaggcc ctacaacatc tacccacatg gcatcactga tgtcaggccc   2040
ctgtacagcc gcaggctgcc aaagggggtg aaacacctca aggacttccc cattctgcct   2100
ggggagatct tcaagtacaa gtggactgtc actgtggagg atggaccaac caaatctgac   2160
cccaggtgcc tcaccagata ctactccagc tttgtgaaca tggagaggga cctggcctct   2220
ggcctgattg gcccactgct catctgctac aaggagtctg tggaccagag gggaaaccag   2280
atcatgtctg acaagaggaa tgtgattctg ttctctgtct ttgatgagaa caggagctgg   2340
tacctgactg agaacattca gcgcttcctg cccaaccctg ctggggtgca gctggaggac   2400
cctgagttcc aggccagcaa catcatgcac tccatcaatg gctatgtgtt tgacagcctc   2460
cagctttctg tctgcctgca tgaggtggcc tactggtaca ttctttctat tggggcccag   2520
actgacttcc tttctgtctt cttctctggc tacaccttca aacacaagat ggtgtatgag   2580
gacaccctga ccctcttccc attctctggg gagactgtgt tcatgagcat ggagaaccct   2640
ggcctgtgga ttctgggatg ccacaactct gacttccgca acaggggcat gactgccctg   2700
ctcaaagtct cctcctgtga caagaacact ggggactact atgaggacag ctatgaggac   2760
atctctgcct acctgctcag caagaacaat gccattgagc ccaggagctt cagccagaat   2820
gtgagcaata atgccaccaa cccacctgtc ctgaaacgcc accagaggga gatcaccagg   2880
accaccctcc agtctgacca ggaggagatt gactatgatg acaccatttc tgtggagatg   2940
aagaaagagg actttgacat ctatgacgag gacgagaacc agagcccaag gagcttccag   3000
aagaagacca ggcactactt cattgctgct gtggagcgcc tgtgggacta tggcatgagc   3060
tccagccccc atgtcctcag gaacagggcc cagtctggct ctgtgccaca gttcaagaaa   3120
gtggtcttcc aagagttcac tgatggcagc ttcacccagc ccctgtacag aggggagctg   3180
aatgagcacc tgggactcct gggcccatac atcagggctg aggtggagga caacatcatg   3240
gtgaccttcc gcaaccaggc ctccaggccc tacagcttct acagctccct catcagctat   3300
gaggaggacc agaggcaggg ggctgagcca cgcaagaact ttgtgaaacc caatgaaacc   3360
aagacctact tctggaaagt ccagcaccac atggccccca ccaaggatga gtttgactgc   3420
aaggcctggg cctacttctc tgatgtggac ctggagaagg atgtgcactc tggcctgatt   3480
ggcccactcc tggtctgcca caccaacacc ctgaaccctg cccatggaag gcaagtgact   3540
gtgcaggagt ttgccctctt cttcaccatc tttgatgaaa ccaagagctg gtacttcact   3600
gagaacatgg agcgcaactg cagggcccca tgcaacattc agatggagga ccccaccttc   3660
aaagagaact accgcttcca tgccatcaat ggctacatca tggacaccct gcctgggctt   3720
gtcatggccc aggaccagag gatcaggtgg tacctgcttt ctatgggctc caatgagaac   3780
attcactcca tccacttctc tgggcatgtc ttcactgtgc gcaagaagga ggagtacaag   3840
atggccctgt acaacctcta ccctggggtc tttgagactg tggagatgct gccctccaaa   3900
gctggcatct ggagggtgga gtgcctcatt ggggagcacc tgcatgctgg catgagcacc   3960
ctgttcctgg tctacagcaa caagtgccag accccccctgg gaatggcctc tggccacatc  4020
agggacttcc agatcactgc ctctggccag tatggccagt gggcccccaa gctggccagg   4080
ctccactact ctggatccat caatgcctgg agcaccaagg agccattcag ctggatcaaa   4140
```

```
gtggacctgc tggcccccat gatcatccat ggcatcaaga cccagggggc caggcagaag   4200
ttctccagcc tgtacatcag ccagttcatc atcatgtaca gcctggatgg caagaaatgg   4260
cagacctaca gaggcaactc cactggaaca ctcatggtct tctttggcaa tgtggacagc   4320
tctggcatca agcacaacat cttcaacccc ccaatcatcg ccagatacat caggctgcac   4380
cccacccact acagcatccg cagcaccctc aggatggagc tgatgggctg tgacctgaac   4440
tcctgcagca tgcccctggg catggagagc aaggccattt ctgatgccca gatcactgcc   4500
tccagctact tcaccaacat gtttgccacc tggagcccaa gcaaggccag gctgcacctc   4560
cagggaagga gcaatgcctg gaggccccag gtcaacaacc caaaggagtg gctgcaggtg   4620
gacttccaga agaccatgaa ggtcactggg gtgaccaccc aggggtcaa gagcctgctc   4680
accagcatgt atgtgaagga gttcctgatc agctccagcc aggatggcca ccagtggacc   4740
ctcttcttcc agaatggcaa ggtcaaggtg ttccagggca accaggacag cttcacccct   4800
gtggtgaaca gcctggaccc ccccctcctg accagatacc tgaggattca cccccagagc   4860
tgggtccacc agattgccct gaggatggag gtcctgggat gtgaggccca ggacctgtac   4920
tgatgaaata aaagatcttt attttcatta gatctgtgtg ttggtttttt gtgtgaggaa   4980
cccctagtga tggagttggc cactccctct ctgcgcgctc gctcgctcac tgaggccggg   5040
cgaccaaagg tcgcccgacg cccgggcttt gcccgggcgg cctcagtgag cgagcgagcg   5100
cgcagagagg gagtggccaa gacgatttaa atgacaagct tggcgtaatc atggtcatag   5160
ctgtttcctg tgtgaaattg ttatccgctc acaattccac acaacatacg agccggaagc   5220
ataaagtgta aagcctgggg tgcctaatga gtgagctaac tcacattaat tgcgttgcgc   5280
tcactgcccg ctttccagtc gggaaacctg tcgtgccagc tgcattaatg aatcggccaa   5340
cgcgcgggga gaggcggttt gcgtattggg cgctcttccg cttcctcgct cactgactcg   5400
ctgcgctcgg tcgttcggct gcggcgagcg gtatcagctc actcaaaggc ggtaatacgg   5460
ttatccacag aatcagggga taacgcagga aagaacatgt gagcaaaagg ccagcaaaag   5520
gccaggaacc gtaaaaaggc cgcgttgctg gcgtttttcc ataggctccg cccccctgac   5580
gagcatcaca aaaatcgacg ctcaagtcag aggtggcgaa acccgacagg actataaaga   5640
taccaggcgt ttccccctgg aagctccctc gtgcgctctc ctgttccgac cctgccgctt   5700
accggatacc tgtccgcctt tctcccttcg ggaagcgtgg cgctttctca tagctcacgc   5760
tgtaggtatc tcagttcggt gtaggtcgtt cgctccaagc tgggctgtgt gcacgaaccc   5820
cccgttcagc ccgaccgctg cgccttatcc ggtaactatc gtcttgagtc caacccggta   5880
agacacgact tatcgccact ggcagcagcc actggtaaca ggattagcag agcgaggtat   5940
gtaggcggtg ctacagagtt cttgaagtgg tggcctaact acggctacac tagaagaaca   6000
gtatttggta tctgcgctct gctgaagcca gttaccttcg gaaaaagagt tggtagctct   6060
tgatccggca aacaaaccac cgctggtagc ggtggttttt ttgtttgcaa gcagcagatt   6120
acgcgcagaa aaaaaggatc tcaagaagat cctttgatct tttctacggg gtctgacgct   6180
cagtggaacg aaaactcacg ttaagggatt ttggtcatga gattatcaaa aaggatcttc   6240
acctagatcc ttttaaatta aaaatgaagt tttaaatcaa tctaaagtat atatgagtaa   6300
acttggtctg acagttacca atgcttaatc agtgaggcac ctatctcagc gatctgtcta   6360
tttcgttcat ccatagttgc ctgactcccc gtcgtgtaga taactacgat acgggagggc   6420
ttaccatctg gccccagtgc tgcaatgata ccgcgagacc cacgctcacc ggctccagat   6480
```

```
ttatcagcaa taaaccagcc agccggaagg gccgagcgca gaagtggtcc tgcaacttta   6540

tccgcctcca tccagtctat taattgttgc cgggaagcta gagtaagtag ttcgccagtt   6600

aatagtttgc gcaacgttgt tgccattgct acaggcatcg tggtgtcacg ctcgtcgttt   6660

ggtatggctt cattcagctc cggttcccaa cgatcaaggc gagttacatg atcccccatg   6720

ttgtgcaaaa aagcggttag ctccttcggt cctccgatcg ttgtcagaag taagttggcc   6780

gcagtgttat cactcatggt tatggcagca ctgcataatt ctcttactgt catgccatcc   6840

gtaagatgct tttctgtgac tggtgagtac tcaaccaagt cattctgaga atagtgtatg   6900

cggcgaccga gttgctcttg cccggcgtca atacgggata ataccgcgcc acatagcaga   6960

actttaaaag tgctcatcat tggaaaacgt tcttcggggc gaaaactctc aaggatctta   7020

ccgctgttga gatccagttc gatgtaaccc actcgtgcac ccaactgatc ttcagcatct   7080

tttactttca ccagcgtttc tgggtgagca aaaacaggaa ggcaaaatgc cgcaaaaaag   7140

ggaataaggg cgacacggaa atgttgaata ctcatactct tcctttttca atattattga   7200

agcatttatc agggttattg tctcatgagc ggatacatat ttgaatgtat ttagaaaaat   7260

aaacaaatag gggttccgcg cacatttccc cgaaaagtgc cacctgacgt ctaagaaacc   7320

attattatca tgacattaac ctataaaaat aggcgtatca cgaggccctt tcgtctcgcg   7380

cgtttcggtg atgacggtga aaacctctga cacatgcagc tcccggagac ggtcacagct   7440

tgtctgtaag cggatgccgg gagcagacaa gcccgtcagg gcgcgtcagc gggtgttggc   7500

gggtgtcggg gctggcttaa ctatgcggca tcagagcaga ttgtactgag agtgcaccat   7560

atgcggtgtg aaataccgca cagatgcgta aggagaaaat accgcatcag gcgccattcg   7620

ccattcaggc tgcgcaactg ttgggaaggg cgatcggtgc gggcctcttc gctattacgc   7680

cagctggcga aagggggatg tgctgcaagg cgattaagtt gggtaacgcc agggttttcc   7740

cagtcacgac gttgtaaaac gacggccagt gaattcctcg agatttaaat gacg         7794
```

```
<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Val Ser Asn Asn Val Ser Asn Asn Ala Thr Asn Asn Ala Thr Asn
1               5                   10                  15


<210> SEQ ID NO 12
<211> LENGTH: 45
<212> TYPE: DNA
<213> ORGANISM: Artificial Sequence
<220> FEATURE:
<223> OTHER INFORMATION: Synthetic

<400> SEQUENCE: 12

gtgagcaaca atgtgagcaa caatgccacc aataatgcta ccaac                    45


<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13
```

Val Ser Asn Asn Ala Thr Asn Asn Val Ser Asn
1 5 10

<210> SEQ ID NO 14
<211> LENGTH: 33
<212> TYPE: DNA
<213> ORGANISM: Artificial Sequence
<220> FEATURE:
<223> OTHER INFORMATION: Synthetic

<400> SEQUENCE: 14
gtgagcaaca atgccaccaa caatgtgagc aac 33

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Val Ser Asn Asn Ala Thr Asn
1 5

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
gtgagcaata atgccaccaa c 21

<210> SEQ ID NO 17
<211> LENGTH: 4
<212> TYPE: PRT
<213> ORGANISM: Artificial Sequence
<220> FEATURE:
<223> OTHER INFORMATION: Synthetic

<400> SEQUENCE: 17

Val Ser Asn Asn
1

<210> SEQ ID NO 18
<211> LENGTH: 12
<212> TYPE: DNA
<213> ORGANISM: Artificial Sequence
<220> FEATURE:
<223> OTHER INFORMATION: Synthetic

<400> SEQUENCE: 18
gtgagcaata at 12

<210> SEQ ID NO 19
<211> LENGTH: 3
<212> TYPE: PRT
<213> ORGANISM: Artificial Sequence
<220> FEATURE:
<223> OTHER INFORMATION: Synthetic

<400> SEQUENCE: 19

Arg Ser Leu
1

<210> SEQ ID NO 20
<211> LENGTH: 9
<212> TYPE: DNA
<213> ORGANISM: Artificial Sequence
<220> FEATURE:
<223> OTHER INFORMATION: Synthetic

<400> SEQUENCE: 20 aggagcctg 9

<210> SEQ ID NO 21
<211> LENGTH: 17
<212> TYPE: PRT
<213> ORGANISM: Artificial Sequence
<220> FEATURE:
<223> OTHER INFORMATION: Synthetic

<400> SEQUENCE: 21

Ala Thr Asn Val Ser Asn Asn Ser Ala Thr Ser Ala Asp Ser Ala Val
1 5 10 15

Ser

<210> SEQ ID NO 22
<211> LENGTH: 51
<212> TYPE: DNA
<213> ORGANISM: Artificial Sequence
<220> FEATURE:
<223> OTHER INFORMATION: Synthetic

<400> SEQUENCE: 22
gccactaatg tgtctaacaa ctctgctacc tctgctgact ctgctgtgag c 51

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Ala Thr Asn Tyr Val Asn Arg Ser Leu
1 5

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24
gccaccaact atgtgaacag gagcctg 27

<210> SEQ ID NO 25
<211> LENGTH: 21
<212> TYPE: PRT
<213> ORGANISM: Artificial Sequence
<220> FEATURE:
<223> OTHER INFORMATION: Synthetic

<400> SEQUENCE: 25

Ala Thr Asn Tyr Val Asn Arg Ser Leu Ser Ala Thr Ser Ala Asp Ser
1 5 10 15

Ala Val Ser Gln Asn
20

<210> SEQ ID NO 26
<211> LENGTH: 63
<212> TYPE: PRT
<213> ORGANISM: Artificial Sequence
<220> FEATURE:
<223> OTHER INFORMATION: Synthetic

<400> SEQUENCE: 26

```
Gly Cys Cys Ala Cys Cys Ala Ala Cys Thr Ala Thr Gly Thr Gly Ala
1               5                   10                  15

Ala Cys Ala Gly Gly Ala Gly Cys Cys Thr Gly Thr Cys Thr Gly Cys
            20                  25                  30

Cys Ala Cys Cys Thr Cys Thr Gly Cys Thr Gly Ala Cys Thr Cys Thr
        35                  40                  45

Gly Cys Thr Gly Thr Gly Ala Gly Cys Cys Ala Gly Ala Ala Thr
    50                  55                  60
```

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

```
Val Ser Asn Asn Val Ser Asn Ala Val Ser Ala Val Ser Ala
1               5                   10
```

<210> SEQ ID NO 28
<211> LENGTH: 42
<212> TYPE: DNA
<213> ORGANISM: Artificial Sequence
<220> FEATURE:
<223> OTHER INFORMATION: Synthetic

<400> SEQUENCE: 28

```
gtgagcaaca atgtgagcaa tgctgtgtct gctgtgtctg ct                        42
```

<210> SEQ ID NO 29
<211> LENGTH: 16
<212> TYPE: PRT
<213> ORGANISM: Artificial Sequence
<220> FEATURE:
<223> OTHER INFORMATION: Synthetic

<400> SEQUENCE: 29

```
Ile Thr Val Ala Ser Ala Thr Ser Asn Ile Thr Val Ala Ser Ala Asp
1               5                   10                  15
```

<210> SEQ ID NO 30
<211> LENGTH: 48
<212> TYPE: DNA
<213> ORGANISM: Artificial Sequence
<220> FEATURE:
<223> OTHER INFORMATION: Synthetic

<400> SEQUENCE: 30

```
atcactgtgg cctctgccac ctctaacatc actgtggcct ctgctgac                  48
```

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Ile Thr Val Thr Asn Ile Thr Val Thr Ala
1 5 10

<210> SEQ ID NO 32
<211> LENGTH: 30
<212> TYPE: DNA
<213> ORGANISM: Artificial Sequence
<220> FEATURE:
<223> OTHER INFORMATION: Synthetic

<400> SEQUENCE: 32
atcactgtga ccaacatcac tgtgactgcc 30

<210> SEQ ID NO 33
<211> LENGTH: 10
<212> TYPE: PRT
<213> ORGANISM: Artificial Sequence
<220> FEATURE:
<223> OTHER INFORMATION: Synthetic

<400> SEQUENCE: 33

Gln Thr Val Thr Asn Ile Thr Val Thr Ala
1 5 10

<210> SEQ ID NO 34
<211> LENGTH: 30
<212> TYPE: DNA
<213> ORGANISM: Artificial Sequence
<220> FEATURE:
<223> OTHER INFORMATION: Synthetic

<400> SEQUENCE: 34
cagactgtga ccaacatcac tgtgactgcc 30

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Ala Thr Asn Val Ser Asn Asn Ser Asn Thr Ser Asn Asp Ser Asn Val
1 5 10 15

Ser

<210> SEQ ID NO 36
<211> LENGTH: 51
<212> TYPE: DNA
<213> ORGANISM: Artificial Sequence
<220> FEATURE:
<223> OTHER INFORMATION: Synthetic

<400> SEQUENCE: 36
gccactaatg tgtctaacaa cagcaacacc agcaatgaca gcaatgtgtc t 51

<210> SEQ ID NO 37
<211> LENGTH: 4374
<212> TYPE: DNA
<213> ORGANISM: Artificial Sequence
<220> FEATURE:
<223> OTHER INFORMATION: Synthetic

<400> SEQUENCE: 37

```
atgcagattg agctgagcac ctgcttcttc ctgtgcctgc tgaggttctg cttctctgcc     60
accaggagat actacctggg ggctgtggag ctttcttggg actacatgca gtctgacctg    120
ggggagctgc ctgtggatgc caggttccca cccagagtgc ccaaatcctt cccattcaac    180
acctctgtgg tctacaagaa gaccctcttt gtggagttca ctgaccacct gttcaacatt    240
gccaaaccca ggccaccctg gatgggactc ctgggaccca ccattcaggc tgaggtgtat    300
gacactgtgg tcatcaccct caagaacatg gcctcccacc ctgtgagcct gcatgctgtg    360
ggggtcagct actggaaggc ctctgagggg gctgagtatg atgaccagac ctcccagagg    420
gagaaggagg atgacaaagt gttccctggg ggcagccaca cctatgtgtg gcaggtcctc    480
aaggagaatg gccccatggc ctctgaccca ctctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaacccctg aggtgcactc cattttcctg gagggccaca ccttcctggt caggaaccac    900
agacaggcca gcctggagat cagccccatc accttcctca ctgcccagac cctgctgatg    960
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg gcccacagag gattggacgc   1320
aagtacaaga aagtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc ccctgtacag ccgcaggctg ccaaaggggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattctttct   1980
attggggccc agactgactt cctttctgtc ttcttctctg gctacacctt caaacacaag   2040
atggtgtatg aggacaccct gaccctcttc ccattctctg ggagactgt gttcatgagc    2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca atgccattga gcccaggagc   2280
ttcagccaga atccacctgt cctgaaacgc caccagaggg agatcaccag gaccaccctc   2340
```

```
cagtctgacc aggaggagat tgactatgat gacaccattt ctgtggagat gaagaaagag   2400
gactttgaca tctatgacga ggacgagaac cagagcccaa ggagcttcca gaagaagacc   2460
aggcactact tcattgctgc tgtggagcgc ctgtgggact atggcatgag ctccagcccc   2520
catgtcctca ggaacagggc ccagtctggc tctgtgccac agttcaagaa agtggtcttc   2580
caagagttca ctgatggcag cttcacccag cccctgtaca gaggggagct gaatgagcac   2640
ctgggactcc tgggcccata catcagggct gaggtggagg acaacatcat ggtgaccttc   2700
cgcaaccagg cctccaggcc ctacagcttc tacagctccc tcatcagcta tgaggaggac   2760
cagaggcagg ggctgagcc  acgcaagaac tttgtgaaac ccaatgaaac caagacctac   2820
ttctggaaag tccagcacca catggccccc accaaggatg agtttgactg caaggcctgg   2880
gcctacttct ctgatgtgga cctggagaag gatgtgcact ctggcctgat tggcccactc   2940
ctggtctgcc acaccaacac cctgaaccct gcccatggaa ggcaagtgac tgtgcaggag   3000
tttgccctct tcttcaccat ctttgatgaa accaagagct ggtacttcac tgagaacatg   3060
gagcgcaact gcagggcccc atgcaacatt cagatggagg accccacctt caaagagaac   3120
taccgcttcc atgccatcaa tggctacatc atggacaccc tgcctgggct tgtcatggcc   3180
caggaccaga ggatcaggtg gtacctgctt tctatgggct ccaatgagaa cattcactcc   3240
atccacttct ctgggcatgt cttcactgtg cgcaagaagg aggagtacaa gatggccctg   3300
tacaacctct accctggggt ctttgagact gtggagatgc tgccctccaa agctggcatc   3360
tggagggtgg agtgcctcat tggggagcac ctgcatgctg gcatgagcac cctgttcctg   3420
gtctacagca acaagtgcca gaccccccctg ggaatggcct ctggccacat cagggacttc   3480
cagatcactg cctctggcca gtatggccag tgggccccca agctggccag gctccactac   3540
tctggatcca tcaatgcctg gagcaccaag gagccattca gctggatcaa agtggacctg   3600
ctggccccca tgatcatcca tggcatcaag acccaggggg ccaggcagaa gttctccagc   3660
ctgtacatca gccagttcat catcatgtac agcctggatg gcaagaaatg gcagacctac   3720
agaggcaact ccactggaac actcatggtc ttctttggca atgtggacag ctctggcatc   3780
aagcacaaca tcttcaaccc cccaatcatc gccagataca tcaggctgca ccccacccac   3840
tacagcatcc gcagcaccct caggatggag ctgatgggct gtgacctgaa ctcctgcagc   3900
atgcccctgg gcatggagag caaggccatt tctgatgccc agatcactgc ctccagctac   3960
ttcaccaaca tgtttgccac ctggagccca agcaaggcca ggctgcacct ccagggaagg   4020
agcaatgcct ggaggcccca ggtcaacaac ccaaaggagt ggctgcaggt ggacttccag   4080
aagaccatga aggtcactgg ggtgaccacc caggggtca agagcctgct caccagcatg    4140
tatgtgaagg agttcctgat cagctccagc caggatggcc accagtggac cctcttcttc   4200
cagaatggca aggtcaaggt gttccagggc aaccaggaca gcttcacccc tgtggtgaac   4260
agcctggacc cccccctcct gaccagatac ctgaggattc acccccagag ctgggtccac   4320
cagattgccc tgaggatgga ggtcctggga tgtgaggccc aggacctgta ctga         4374
```

<210> SEQ ID NO 38
<211> LENGTH: 5191
<212> TYPE: DNA
<213> ORGANISM: Artificial Sequence
<220> FEATURE:
<223> OTHER INFORMATION: Synthetic

<400> SEQUENCE: 38

```
ttggccactc cctctctgcg cgctcgctcg ctcactgagg ccgggcgacc aaaggtcgcc     60
```

```
cgacgcccgg gctttgcccg ggcggcctca gtgagcgagc gagcgcgcag agagggagtg    120
gccaactcca tcactagggg ttcctgagtt taaacttcgt cgacggggga ggctgctggt    180
gaatattaac caaggtcacc ccagttatcg gaggagcaaa caggggctaa gtccaccggg    240
ggaggctgct ggtgaatatt aaccaaggtc accccagtta tcggaggagc aaacaggggc    300
taagtccaca aatgacctat taagaatatt tcatagaacg aatgttccga tgctctaatc    360
tctctagaca aggttcatat ttgtatgggt tacttattct ctctttgttg actaagtcaa    420
taatcagaat cagcaggttt gcagtcagat tggcagggat aagcagccta gctcaggaga    480
agtgagtata aaagccccag gctgggagca gccatcacag aagtccactc attcttggca    540
ggggcgcgcc gccaccatgc agattgagct gagcacctgc ttcttcctgt gcctgctgag    600
gttctgcttc tctgccacca ggagatacta cctgggggct gtggagcttt cttgggacta    660
catgcagtct gacctggggg agctgcctgt ggatgccagg ttcccaccca gagtgcccaa    720
atccttccca ttcaacacct ctgtggtcta caagaagacc ctctttgtgg agttcactga    780
ccacctgttc aacattgcca aacccaggcc accctggatg ggactcctgg gacccaccat    840
tcaggctgag gtgtatgaca ctgtggtcgt caccctcaag aacatggcct cccaccctgt    900
gagcctgcat gctgtggggg tcagctactg gaagtcctct gagggggctg agtatgatga    960
ccagacctcc cagagggaga aggaggatga caaagtgttc cctgggaaga gccacaccta   1020
tgtgtggcag gtcctcaagg agaatggccc cactgcctct gacccaccct gcctgaccta   1080
ctcctacctt tctcatgtgg acctggtcaa ggacctcaac tctggactga ttggggccct   1140
gctggtgtgc agggagggct ccctggccaa agagaagacc cagaccctgc acaagttcat   1200
tctcctgttt gctgtctttg atgagggcaa gagctggcac tctgaaacca agaactccct   1260
gatgcaggac agggatgctg cctctgccag ggcctggccc aagatgcaca ctgtgaatgg   1320
ctatgtgaac aggagcctgc ctggactcat tggctgccac aggaaatctg tctactggca   1380
tgtgattggc atggggacaa cccctgaggt gcactccatt ttcctggagg gccacacctt   1440
cctggtcagg aaccacagac aggccagcct ggagatcagc cccatcacct tcctcactgc   1500
ccagaccctg ctgatggacc tcggacagtt cctgctgttc tgccacatca gctcccacca   1560
gcatgatggc atggaggcct atgtcaaggt ggacagctgc cctgaggagc cacagctcag   1620
gatgaagaac aatgaggagg ctgaggacta tgatgatgac ctgactgact ctgagatgga   1680
tgtggtccgc tttgatgatg acaacagccc atccttcatt cagatcaggt ctgtggccaa   1740
gaaacacccc aagacctggg tgcactacat tgctgctgag gaggaggact gggactatgc   1800
cccactggtc ctggcccctg atgacaggag ctacaagagc cagtacctca acaatggccc   1860
acagaggatt ggacgcaagt acaagaaagt caggttcatg gcctacactg atgaaacctt   1920
caagaccagg gaggccattc agcatgagtc tggcatcctg ggcccactcc tgtatgggga   1980
ggtgggggac accctgctca tcatcttcaa gaaccaggcc tccaggccct acaacatcta   2040
cccacatggc atcactgatg tcaggcccct gtacagccgc aggctgccaa agggggtgaa   2100
acacctcaag gacttcccca ttctgcctgg ggagatcttc aagtacaagt ggactgtcac   2160
tgtggaggat ggaccaacca aatctgaccc caggtgcctc accagatact actccagctt   2220
tgtgaacatg gagagggacc tggcctctgg cctgattggc ccactgctca tctgctacaa   2280
ggagtctgtg gaccagaggg gaaaccagat catgtctgac aagaggaatg tgattctgtt   2340
ctctgtcttt gatgagaaca ggagctggta cctgactgag aacattcagc gcttcctgcc   2400
```

```
caaccctgct ggggtgcagc tggaggaccc tgagttccag gccagcaaca tcatgcactc   2460
catcaatggc tatgtgtttg acagcctcca gctttctgtc tgcctgcatg aggtggccta   2520
ctggtacatt ctttctattg ggcccagac tgacttcctt tctgtcttct tctctggcta   2580
caccttcaaa cacaagatgg tgtatgagga caccctgacc ctcttcccat tctctgggga   2640
gactgtgttc atgagcatgg agaaccctgg cctgtggatt ctgggatgcc acaactctga   2700
cttccgcaac aggggcatga ctgccctgct caaagtctcc tcctgtgaca agaacactgg   2760
ggactactat gaggacagct atgaggacat ctctgcctac ctgctcagca agaacaatgc   2820
cattgagccc aggagcttca gccagaatgt gagcaataat gccaccaacc cacctgtcct   2880
gaaacgccac cagagggaga tcaccaggac caccctccag tctgaccagg aggagattga   2940
ctatgatgac accatttctg tggagatgaa gaaagaggac tttgacatct atgacgagga   3000
cgagaaccag agcccaagga gcttccagaa gaagaccagg cactacttca ttgctgctgt   3060
ggagcgcctg tgggactatg gcatgagctc cagcccccat gtcctcagga acagggccca   3120
gtctggctct gtgccacagt tcaagaaagt ggtcttccaa gagttcactg atggcagctt   3180
cacccagccc ctgtacagag gggagctgaa tgagcacctg ggactcctgg gcccatacat   3240
cagggctgag gtggaggaca acatcatggt gaccttccgc aaccaggcct ccaggcccta   3300
cagcttctac agctccctca tcagctatga ggaggaccag aggcaggggg ctgagccacg   3360
caagaacttt gtgaaaccca atgaaaccaa gacctacttc tggaaagtcc agcaccacat   3420
ggcccccacc aaggatgagt ttgactgcaa ggcctgggcc tacttctctg atgtggacct   3480
ggagaaggat gtgcactctg gcctgattgg cccactcctg gtctgccaca ccaacaccct   3540
gaaccctgcc catggaaggc aagtgactgt gcaggagttt gccctcttct tcaccatctt   3600
tgatgaaacc aagagctggt acttcactga gaacatggag cgcaactgca gggccccatg   3660
caacattcag atggaggacc ccaccttcaa agagaactac cgcttccatg ccatcaatgg   3720
ctacatcatg gacaccctgc ctgggcttgt catggcccag gaccagagga tcaggtggta   3780
cctgctttct atgggctcca atgagaacat tcactccatc cacttctctg ggcatgtctt   3840
cactgtgcgc aagaaggagg agtacaagat ggccctgtac aacctctacc ctggggtctt   3900
tgagactgtg gagatgctgc cctccaaagc tggcatctgg agggtggagt gcctcattgg   3960
ggagcacctg catgctggca tgagcaccct gttcctggtc tacagcaaca agtgccagac   4020
cccccctggga atggcctctg gccacatcag ggacttccag atcactgcct ctggccagta   4080
tggccagtgg gcccccaagc tggccaggct ccactactct ggatccatca atgcctggag   4140
caccaaggag ccattcagct ggatcaaagt ggacctgctg gcccccatga tcatccatgg   4200
catcaagacc caggggggcca ggcagaagtt ctccagcctg tacatcagcc agttcatcat   4260
catgtacagc ctggatggca agaaatggca gacctacaga ggcaactcca ctggaacact   4320
catggtcttc tttggcaatg tggacagctc tggcatcaag cacaacatct tcaacccccc   4380
aatcatcgcc agatacatca ggctgcaccc cacccactac agcatccgca gcaccctcag   4440
gatggagctg atgggctgtg acctgaactc ctgcagcatg cccctgggca tggagagcaa   4500
ggccatttct gatgcccaga tcactgcctc cagctacttc accaacatgt ttgccacctg   4560
gagcccaagc aaggccaggc tgcacctcca gggaaggagc aatgcctgga ggccccaggt   4620
caacaaccca aaggagtggc tgcaggtgga cttccagaag accatgaagg tcactggggt   4680
gaccacccag ggggtcaaga gcctgctcac cagcatgtat gtgaaggagt tcctgatcag   4740
ctccagccag gatggccacc agtggaccct cttcttccag aatggcaagg tcaaggtgtt   4800
```

```
ccagggcaac caggacagct tcacccctgt ggtgaacagc ctggaccccc ccctcctgac   4860

cagatacctg aggattcacc cccagagctg ggtccaccag attgccctga ggatggaggt   4920

cctgggatgt gaggcccagg acctgtactg atgagcggcc gctcttagta gcagtatcga   4980

taataaaaga tctttatttt cattagatct gtgtgttggt tttttgtgtg ttaattaagc   5040

tcgcgaagga acccctagtg atggagttgg ccactccctc tctgcgcgct cgctcgctca   5100

ctgaggccgg gcgaccaaag gtcgcccgac gcccgggctt tgcccgggcg gcctcagtga   5160

gcgagcgagc gcgcagagag ggagtggcca a                                  5191


<210> SEQ ID NO 39
<211> LENGTH: 2351
<212> TYPE: PRT
<213> ORGANISM: Artificial Sequence
<220> FEATURE:
<223> OTHER INFORMATION: Synthetic

<400> SEQUENCE: 39

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285
```

```
Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
```

-continued

```
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
        995                 1000                 1005

Leu Phe  Lys Val Ser Ile Ser  Leu Leu Lys Thr Asn  Lys Thr Ser
    1010                 1015                 1020

Asn Asn  Ser Ala Thr Asn Arg  Lys Thr His Ile Asp  Gly Pro Ser
    1025                 1030                 1035

Leu Leu  Ile Glu Asn Ser Pro  Ser Val Trp Gln Asn  Ile Leu Glu
    1040                 1045                 1050

Ser Asp  Thr Glu Phe Lys Lys  Val Thr Pro Leu Ile  His Asp Arg
    1055                 1060                 1065

Met Leu  Met Asp Lys Asn Ala  Thr Ala Leu Arg Leu  Asn His Met
    1070                 1075                 1080

Ser Asn  Lys Thr Thr Ser Ser  Lys Asn Met Glu Met  Val Gln Gln
    1085                 1090                 1095

Lys Lys  Glu Gly Pro Ile Pro  Pro Asp Ala Gln Asn  Pro Asp Met
    1100                 1105                 1110

Ser Phe  Phe Lys Met Leu Phe  Leu Pro Glu Ser Ala  Arg Trp Ile
    1115                 1120                 1125
```

```
Gln Arg  Thr His Gly Lys Asn  Ser Leu Asn Ser Gly  Gln Gly Pro
    1130                 1135                 1140

Ser Pro  Lys Gln Leu Val Ser  Leu Gly Pro Glu Lys  Ser Val Glu
    1145                 1150                 1155

Gly Gln  Asn Phe Leu Ser Glu  Lys Asn Lys Val Val  Val Gly Lys
    1160                 1165                 1170

Gly Glu  Phe Thr Lys Asp Val  Gly Leu Lys Glu Met  Val Phe Pro
    1175                 1180                 1185

Ser Ser  Arg Asn Leu Phe Leu  Thr Asn Leu Asp Asn  Leu His Glu
    1190                 1195                 1200

Asn Asn  Thr His Asn Gln Glu  Lys Lys Ile Gln Glu  Glu Ile Glu
    1205                 1210                 1215

Lys Lys  Glu Thr Leu Ile Gln  Glu Asn Val Val Leu  Pro Gln Ile
    1220                 1225                 1230

His Thr  Val Thr Gly Thr Lys  Asn Phe Met Lys Asn  Leu Phe Leu
    1235                 1240                 1245

Leu Ser  Thr Arg Gln Asn Val  Glu Gly Ser Tyr Asp  Gly Ala Tyr
    1250                 1255                 1260

Ala Pro  Val Leu Gln Asp Phe  Arg Ser Leu Asn Asp  Ser Thr Asn
    1265                 1270                 1275

Arg Thr  Lys Lys His Thr Ala  His Phe Ser Lys Lys  Gly Glu Glu
    1280                 1285                 1290

Glu Asn  Leu Glu Gly Leu Gly  Asn Gln Thr Lys Gln  Ile Val Glu
    1295                 1300                 1305

Lys Tyr  Ala Cys Thr Thr Arg  Ile Ser Pro Asn Thr  Ser Gln Gln
    1310                 1315                 1320

Asn Phe  Val Thr Gln Arg Ser  Lys Arg Ala Leu Lys  Gln Phe Arg
    1325                 1330                 1335

Leu Pro  Leu Glu Glu Thr Glu  Leu Glu Lys Arg Ile  Ile Val Asp
    1340                 1345                 1350

Asp Thr  Ser Thr Gln Trp Ser  Lys Asn Met Lys His  Leu Thr Pro
    1355                 1360                 1365

Ser Thr  Leu Thr Gln Ile Asp  Tyr Asn Glu Lys Glu  Lys Gly Ala
    1370                 1375                 1380

Ile Thr  Gln Ser Pro Leu Ser  Asp Cys Leu Thr Arg  Ser His Ser
    1385                 1390                 1395

Ile Pro  Gln Ala Asn Arg Ser  Pro Leu Pro Ile Ala  Lys Val Ser
    1400                 1405                 1410

Ser Phe  Pro Ser Ile Arg Pro  Ile Tyr Leu Thr Arg  Val Leu Phe
    1415                 1420                 1425

Gln Asp  Asn Ser Ser His Leu  Pro Ala Ala Ser Tyr  Arg Lys Lys
    1430                 1435                 1440

Asp Ser  Gly Val Gln Glu Ser  Ser His Phe Leu Gln  Gly Ala Lys
    1445                 1450                 1455

Lys Asn  Asn Leu Ser Leu Ala  Ile Leu Thr Leu Glu  Met Thr Gly
    1460                 1465                 1470

Asp Gln  Arg Glu Val Gly Ser  Leu Gly Thr Ser Ala  Thr Asn Ser
    1475                 1480                 1485

Val Thr  Tyr Lys Lys Val Glu  Asn Thr Val Leu Pro  Lys Pro Asp
    1490                 1495                 1500

Leu Pro  Lys Thr Ser Gly Lys  Val Glu Leu Leu Pro  Lys Val His
    1505                 1510                 1515
```

-continued

```
Ile Tyr  Gln Lys Asp Leu Phe  Pro Thr Glu Thr Ser  Asn Gly Ser
    1520                 1525                 1530

Pro Gly  His Leu Asp Leu Val  Glu Gly Ser Leu Leu  Gln Gly Thr
    1535                 1540                 1545

Glu Gly  Ala Ile Lys Trp Asn  Glu Ala Asn Arg Pro  Gly Lys Val
    1550                 1555                 1560

Pro Phe  Leu Arg Val Ala Thr  Glu Ser Ser Ala Lys  Thr Pro Ser
    1565                 1570                 1575

Lys Leu  Leu Asp Pro Leu Ala  Trp Asp Asn His Tyr  Gly Thr Gln
    1580                 1585                 1590

Ile Pro  Lys Glu Glu Trp Lys  Ser Gln Glu Lys Ser  Pro Glu Lys
    1595                 1600                 1605

Thr Ala  Phe Lys Lys Lys Asp  Thr Ile Leu Ser Leu  Asn Ala Cys
    1610                 1615                 1620

Glu Ser  Asn His Ala Ile Ala  Ala Ile Asn Glu Gly  Gln Asn Lys
    1625                 1630                 1635

Pro Glu  Ile Glu Val Thr Trp  Ala Lys Gln Gly Arg  Thr Glu Arg
    1640                 1645                 1650

Leu Cys  Ser Gln Asn Pro Pro  Val Leu Lys Arg His  Gln Arg Glu
    1655                 1660                 1665

Ile Thr  Arg Thr Thr Leu Gln  Ser Asp Gln Glu Glu  Ile Asp Tyr
    1670                 1675                 1680

Asp Asp  Thr Ile Ser Val Glu  Met Lys Lys Glu Asp  Phe Asp Ile
    1685                 1690                 1695

Tyr Asp  Glu Asp Glu Asn Gln  Ser Pro Arg Ser Phe  Gln Lys Lys
    1700                 1705                 1710

Thr Arg  His Tyr Phe Ile Ala  Ala Val Glu Arg Leu  Trp Asp Tyr
    1715                 1720                 1725

Gly Met  Ser Ser Ser Pro His  Val Leu Arg Asn Arg  Ala Gln Ser
    1730                 1735                 1740

Gly Ser  Val Pro Gln Phe Lys  Lys Val Val Phe Gln  Glu Phe Thr
    1745                 1750                 1755

Asp Gly  Ser Phe Thr Gln Pro  Leu Tyr Arg Gly Glu  Leu Asn Glu
    1760                 1765                 1770

His Leu  Gly Leu Leu Gly Pro  Tyr Ile Arg Ala Glu  Val Glu Asp
    1775                 1780                 1785

Asn Ile  Met Val Thr Phe Arg  Asn Gln Ala Ser Arg  Pro Tyr Ser
    1790                 1795                 1800

Phe Tyr  Ser Ser Leu Ile Ser  Tyr Glu Glu Asp Gln  Arg Gln Gly
    1805                 1810                 1815

Ala Glu  Pro Arg Lys Asn Phe  Val Lys Pro Asn Glu  Thr Lys Thr
    1820                 1825                 1830

Tyr Phe  Trp Lys Val Gln His  His Met Ala Pro Thr  Lys Asp Glu
    1835                 1840                 1845

Phe Asp  Cys Lys Ala Trp Ala  Tyr Phe Ser Asp Val  Asp Leu Glu
    1850                 1855                 1860

Lys Asp  Val His Ser Gly Leu  Ile Gly Pro Leu Leu  Val Cys His
    1865                 1870                 1875

Thr Asn  Thr Leu Asn Pro Ala  His Gly Arg Gln Val  Thr Val Gln
    1880                 1885                 1890

Glu Phe  Ala Leu Phe Phe Thr  Ile Phe Asp Glu Thr  Lys Ser Trp
    1895                 1900                 1905

Tyr Phe  Thr Glu Asn Met Glu  Arg Asn Cys Arg Ala  Pro Cys Asn
```

```
    1910                1915                1920

Ile Gln  Met Glu Asp Pro Thr  Phe Lys Glu Asn Tyr  Arg Phe His
    1925                1930                1935

Ala Ile  Asn Gly Tyr Ile Met  Asp Thr Leu Pro Gly  Leu Val Met
    1940                1945                1950

Ala Gln  Asp Gln Arg Ile Arg  Trp Tyr Leu Leu Ser  Met Gly Ser
    1955                1960                1965

Asn Glu  Asn Ile His Ser Ile  His Phe Ser Gly His  Val Phe Thr
    1970                1975                1980

Val Arg  Lys Lys Glu Glu Tyr  Lys Met Ala Leu Tyr  Asn Leu Tyr
    1985                1990                1995

Pro Gly  Val Phe Glu Thr Val  Glu Met Leu Pro Ser  Lys Ala Gly
    2000                2005                2010

Ile Trp  Arg Val Glu Cys Leu  Ile Gly Glu His Leu  His Ala Gly
    2015                2020                2025

Met Ser  Thr Leu Phe Leu Val  Tyr Ser Asn Lys Cys  Gln Thr Pro
    2030                2035                2040

Leu Gly  Met Ala Ser Gly His  Ile Arg Asp Phe Gln  Ile Thr Ala
    2045                2050                2055

Ser Gly  Gln Tyr Gly Gln Trp  Ala Pro Lys Leu Ala  Arg Leu His
    2060                2065                2070

Tyr Ser  Gly Ser Ile Asn Ala  Trp Ser Thr Lys Glu  Pro Phe Ser
    2075                2080                2085

Trp Ile  Lys Val Asp Leu Leu  Ala Pro Met Ile Ile  His Gly Ile
    2090                2095                2100

Lys Thr  Gln Gly Ala Arg Gln  Lys Phe Ser Ser Leu  Tyr Ile Ser
    2105                2110                2115

Gln Phe  Ile Ile Met Tyr Ser  Leu Asp Gly Lys Lys  Trp Gln Thr
    2120                2125                2130

Tyr Arg  Gly Asn Ser Thr Gly  Thr Leu Met Val Phe  Phe Gly Asn
    2135                2140                2145

Val Asp  Ser Ser Gly Ile Lys  His Asn Ile Phe Asn  Pro Pro Ile
    2150                2155                2160

Ile Ala  Arg Tyr Ile Arg Leu  His Pro Thr His Tyr  Ser Ile Arg
    2165                2170                2175

Ser Thr  Leu Arg Met Glu Leu  Met Gly Cys Asp Leu  Asn Ser Cys
    2180                2185                2190

Ser Met  Pro Leu Gly Met Glu  Ser Lys Ala Ile Ser  Asp Ala Gln
    2195                2200                2205

Ile Thr  Ala Ser Ser Tyr Phe  Thr Asn Met Phe Ala  Thr Trp Ser
    2210                2215                2220

Pro Ser  Lys Ala Arg Leu His  Leu Gln Gly Arg Ser  Asn Ala Trp
    2225                2230                2235

Arg Pro  Gln Val Asn Asn Pro  Lys Glu Trp Leu Gln  Val Asp Phe
    2240                2245                2250

Gln Lys  Thr Met Lys Val Thr  Gly Val Thr Thr Gln  Gly Val Lys
    2255                2260                2265

Ser Leu  Leu Thr Ser Met Tyr  Val Lys Glu Phe Leu  Ile Ser Ser
    2270                2275                2280

Ser Gln  Asp Gly His Gln Trp  Thr Leu Phe Phe Gln  Asn Gly Lys
    2285                2290                2295

Val Lys  Val Phe Gln Gly Asn  Gln Asp Ser Phe Thr  Pro Val Val
    2300                2305                2310
```

```
Asn Ser  Leu Asp Pro Pro Leu  Leu Thr Arg Tyr Leu  Arg Ile His
    2315                 2320                 2325

Pro Gln  Ser Trp Val His Gln  Ile Ala Leu Arg Met  Glu Val Leu
    2330                 2335                 2340

Gly Cys  Glu Ala Gln Asp Leu  Tyr
    2345                 2350


<210> SEQ ID NO 40
<211> LENGTH: 42
<212> TYPE: DNA
<213> ORGANISM: Artificial Sequence
<220> FEATURE:
<223> OTHER INFORMATION: Synthetic

<400> SEQUENCE: 40

agcttcagcc agaatccacc tgtcctgaaa cgccaccaga gg                         42


<210> SEQ ID NO 41
<211> LENGTH: 87
<212> TYPE: DNA
<213> ORGANISM: Artificial Sequence
<220> FEATURE:
<223> OTHER INFORMATION: Synthetic

<400> SEQUENCE: 41

agcttcagcc agaatgtgag caacaatgtg agcaacaatg ccaccaataa tgctaccaac     60

ccacctgtcc tgaaacgcca ccagagg                                          87


<210> SEQ ID NO 42
<211> LENGTH: 75
<212> TYPE: DNA
<213> ORGANISM: Artificial Sequence
<220> FEATURE:
<223> OTHER INFORMATION: Synthetic

<400> SEQUENCE: 42

agcttcagcc agaatgtgag caacaatgcc accaacaatg tgagcaaccc acctgtcctg     60

aaacgccacc agagg                                                       75


<210> SEQ ID NO 43
<211> LENGTH: 63
<212> TYPE: DNA
<213> ORGANISM: Artificial Sequence
<220> FEATURE:
<223> OTHER INFORMATION: Synthetic

<400> SEQUENCE: 43

agcttcagcc agaatgtgag caataatgcc accaacccac ctgtcctgaa acgccaccag     60

agg                                                                    63


<210> SEQ ID NO 44
<211> LENGTH: 54
<212> TYPE: DNA
<213> ORGANISM: Artificial Sequence
<220> FEATURE:
<223> OTHER INFORMATION: Synthetic

<400> SEQUENCE: 44

agcttcagcc agaatgtgag caataatcca cctgtcctga aacgccacca gagg            54


<210> SEQ ID NO 45
<211> LENGTH: 51
```

<212> TYPE: DNA
<213> ORGANISM: Artificial Sequence
<220> FEATURE:
<223> OTHER INFORMATION: Synthetic

<400> SEQUENCE: 45
agcttcagcc agaataggag cctgccacct gtcctgaaac gccaccagag g 51

<210> SEQ ID NO 46
<211> LENGTH: 93
<212> TYPE: DNA
<213> ORGANISM: Artificial Sequence
<220> FEATURE:
<223> OTHER INFORMATION: Synthetic

<400> SEQUENCE: 46
agcttcagcc agaatgccac taatgtgtct aacaactctg ctacctctgc tgactctgct 60
gtgagcccac ctgtcctgaa acgccaccag agg 93

<210> SEQ ID NO 47
<211> LENGTH: 69
<212> TYPE: DNA
<213> ORGANISM: Artificial Sequence
<220> FEATURE:
<223> OTHER INFORMATION: Synthetic

<400> SEQUENCE: 47
agcttcagcc agaatgccac caactatgtg aacaggagcc tgccacctgt cctgaaacgc 60
caccagagg 69

<210> SEQ ID NO 48
<211> LENGTH: 105
<212> TYPE: DNA
<213> ORGANISM: Artificial Sequence
<220> FEATURE:
<223> OTHER INFORMATION: Synthetic

<400> SEQUENCE: 48
agcttcagcc agaatgccac caactatgtg aacaggagcc tgtctgccac ctctgctgac 60
tctgctgtga gccagaatcc acctgtcctg aaacgccacc agagg 105

<210> SEQ ID NO 49
<211> LENGTH: 84
<212> TYPE: DNA
<213> ORGANISM: Artificial Sequence
<220> FEATURE:
<223> OTHER INFORMATION: Synthetic

<400> SEQUENCE: 49
agcttcagcc agaatgtgag caacaatgtg agcaatgctg tgtctgctgt gtctgctcca 60
cctgtcctga aacgccacca gagg 84

<210> SEQ ID NO 50
<211> LENGTH: 90
<212> TYPE: DNA
<213> ORGANISM: Artificial Sequence
<220> FEATURE:
<223> OTHER INFORMATION: Synthetic

<400> SEQUENCE: 50
agcttcagcc agaatatcac tgtggcctct gccacctcta acatcactgt ggcctctgct 60
gacccacctg tcctgaaacg ccaccagagg 90

<210> SEQ ID NO 51
<211> LENGTH: 72
<212> TYPE: DNA
<213> ORGANISM: Artificial Sequence
<220> FEATURE:
<223> OTHER INFORMATION: Synthetic

<400> SEQUENCE: 51
agcttcagcc agaatatcac tgtgaccaac atcactgtga ctgccccacc tgtcctgaaa 60
cgccaccaga gg 72

<210> SEQ ID NO 52
<211> LENGTH: 72
<212> TYPE: DNA
<213> ORGANISM: Artificial Sequence
<220> FEATURE:
<223> OTHER INFORMATION: Synthetic

<400> SEQUENCE: 52
agcttcagcc agaatcagac tgtgaccaac atcactgtga ctgccccacc tgtcctgaaa 60
cgccaccaga gg 72

<210> SEQ ID NO 53
<211> LENGTH: 93
<212> TYPE: DNA
<213> ORGANISM: Artificial Sequence
<220> FEATURE:
<223> OTHER INFORMATION: Synthetic

<400> SEQUENCE: 53
agcttcagcc agaatgccac taatgtgtct aacaacagca acaccagcaa tgacagcaat 60
gtgtctccac ctgtcctgaa acgccaccag agg 93

<210> SEQ ID NO 54
<211> LENGTH: 2674
<212> TYPE: DNA
<213> ORGANISM: Artificial Sequence
<220> FEATURE:
<223> OTHER INFORMATION: Synthetic

<400> SEQUENCE: 54
gacgatttaa atgacaagct tggcgtaatc atggtcatag ctgtttcctg tgtgaaattg 60
ttatccgctc acaattccac acaacatacg agccggaagc ataaagtgta aagcctgggg 120
tgcctaatga gtgagctaac tcacattaat tgcgttgcgc tcactgcccg ctttccagtc 180
gggaaacctg tcgtgccagc tgcattaatg aatcggccaa cgcgcgggga gaggcggttt 240
gcgtattggg cgctcttccg cttcctcgct cactgactcg ctgcgctcgg tcgttcggct 300
gcggcgagcg gtatcagctc actcaaaggc ggtaatacgg ttatccacag aatcagggga 360
taacgcagga aagaacatgt gagcaaaagg ccagcaaaag gccaggaacc gtaaaaaggc 420
cgcgttgctg gcgtttttcc ataggctccg cccccctgac gagcatcaca aaaatcgacg 480
ctcaagtcag aggtggcgaa acccgacagg actataaaga taccaggcgt ttccccctgg 540
aagctccctc gtgcgctctc ctgttccgac cctgccgctt accggatacc tgtccgcctt 600
tctcccttcg ggaagcgtgg cgctttctca tagctcacgc tgtaggtatc tcagttcggt 660
gtaggtcgtt cgctccaagc tgggctgtgt gcacgaaccc cccgttcagc ccgaccgctg 720
cgccttatcc ggtaactatc gtcttgagtc caacccggta agacacgact tatcgccact 780
ggcagcagcc actggtaaca ggattagcag agcgaggtat gtaggcggtg ctacagagtt 840

```
cttgaagtgg tggcctaact acggctacac tagaagaaca gtatttggta tctgcgctct    900
gctgaagcca gttaccttcg gaaaaagagt tggtagctct tgatccggca aacaaaccac    960
cgctggtagc ggtggttttt ttgtttgcaa gcagcagatt acgcgcagaa aaaaaggatc   1020
tcaagaagat cctttgatct tttctacggg gtctgacgct cagtggaacg aaaactcacg   1080
ttaagggatt ttggtcatga gattatcaaa aaggatcttc acctagatcc ttttaaatta   1140
aaaatgaagt tttaaatcaa tctaaagtat atatgagtaa acttggtctg acagttacca   1200
atgcttaatc agtgaggcac ctatctcagc gatctgtcta tttcgttcat ccatagttgc   1260
ctgactcccc gtcgtgtaga taactacgat acgggagggc ttaccatctg gccccagtgc   1320
tgcaatgata ccgcgagacc cacgctcacc ggctccagat ttatcagcaa taaaccagcc   1380
agccggaagg gccgagcgca gaagtggtcc tgcaacttta tccgcctcca tccagtctat   1440
taattgttgc cgggaagcta gagtaagtag ttcgccagtt aatagtttgc gcaacgttgt   1500
tgccattgct acaggcatcg tggtgtcacg ctcgtcgttt ggtatggctt cattcagctc   1560
cggttcccaa cgatcaaggc gagttacatg atcccccatg ttgtgcaaaa aagcggttag   1620
ctccttcggt cctccgatcg ttgtcagaag taagttggcc gcagtgttat cactcatggt   1680
tatggcagca ctgcataatt ctcttactgt catgccatcc gtaagatgct tttctgtgac   1740
tggtgagtac tcaaccaagt cattctgaga atagtgtatg cggcgaccga gttgctcttg   1800
cccggcgtca atacgggata ataccgcgcc acatagcaga actttaaaag tgctcatcat   1860
tggaaaacgt tcttcggggc gaaaactctc aaggatctta ccgctgttga gatccagttc   1920
gatgtaaccc actcgtgcac ccaactgatc ttcagcatct tttactttca ccagcgtttc   1980
tgggtgagca aaaacaggaa ggcaaaatgc cgcaaaaaag ggaataaggg cgacacggaa   2040
atgttgaata ctcatactct tcctttttca atattattga agcatttatc agggttattg   2100
tctcatgagc ggatacatat ttgaatgtat ttagaaaaat aaacaaatag gggttccgcg   2160
cacatttccc cgaaaagtgc cacctgacgt ctaagaaacc attattatca tgacattaac   2220
ctataaaaat aggcgtatca cgaggccctt tcgtctcgcg cgtttcggtg atgacggtga   2280
aaacctctga cacatgcagc tcccggagac ggtcacagct tgtctgtaag cggatgccgg   2340
gagcagacaa gcccgtcagg gcgcgtcagc gggtgttggc gggtgtcggg gctggcttaa   2400
ctatgcggca tcagagcaga ttgtactgag agtgcaccat atgcggtgtg aaataccgca   2460
cagatgcgta aggagaaaat accgcatcag gcgccattcg ccattcaggc tgcgcaactg   2520
ttgggaaggg cgatcggtgc gggcctcttc gctattacgc cagctggcga aaggggggatg  2580
tgctgcaagg cgattaagtt gggtaacgcc agggttttcc cagtcacgac gttgtaaaac   2640
gacggccagt gaattcctcg agatttaaat gacg                               2674
```

<210> SEQ ID NO 55
<211> LENGTH: 1015
<212> TYPE: DNA
<213> ORGANISM: Artificial Sequence
<220> FEATURE:
<223> OTHER INFORMATION: Synthetic

<400> SEQUENCE: 55

```
tggcgtaatc atggtcatag ctgtttcctg tgtgaaattg ttatccgctc acaattccac     60
acaacatacg agccggaagc ataaagtgta aagcctgggg tgcctaatga gtgagctaac    120
tcacattaat tgcgttgcgc tcactgcccg ctttccagtc gggaaacctg tcgtgccagc    180
```

```
tgcattaatg aatcggccaa cgcgcgggga gaggcggttt gcgtattggg cgctcttccg     240

cttcctcgct cactgactcg ctgcgctcgg tcgttcggct gcggcgagcg gtatcagctc     300

actcaaaggc ggtaatacgg ttatccacag aatcagggga taacgcagga aagaacatgt     360

gagcaaaagg ccagcaaaag gccaggaacc gtaaaaaggc cgcgttgctg gcgtttttcc     420

ataggctccg cccccctgac gagcatcaca aaaatcgacg ctcaagtcag aggtggcgaa     480

acccgacagg actataaaga taccaggcgt ttccccctgg aagctccctc gtgcgctctc     540

ctgttccgac cctgccgctt accggatacc tgtccgcctt tctcccttcg ggaagcgtgg     600

cgctttctca tagctcacgc tgtaggtatc tcagttcggt gtaggtcgtt cgctccaagc     660

tgggctgtgt gcacgaaccc cccgttcagc ccgaccgctg cgccttatcc ggtaactatc     720

gtcttgagtc caacccggta agacacgact tatcgccact ggcagcagcc actggtaaca     780

ggattagcag agcgaggtat gtaggcggtg ctacagagtt cttgaagtgg tggcctaact     840

acggctacac tagaagaaca gtatttggta tctgcgctct gctgaagcca gttaccttcg     900

gaaaaagagt tggtagctct tgatccggca aacaaaccac cgctggtagc ggtggttttt     960

ttgtttgcaa gcagcagatt acgcgcagaa aaaaaggatc tcaagaagat ccttt         1015
```

<210> SEQ ID NO 56
<211> LENGTH: 861
<212> TYPE: DNA
<213> ORGANISM: Artificial Sequence
<220> FEATURE:
<223> OTHER INFORMATION: Synthetic

<400> SEQUENCE: 56

```
ttaccaatgc ttaatcagtg aggcacctat ctcagcgatc tgtctatttc gttcatccat      60

agttgcctga ctccccgtcg tgtagataac tacgatacgg gagggcttac catctggccc     120

cagtgctgca atgataccgc gagacccacg ctcaccggct ccagatttat cagcaataaa     180

ccagccagcc ggaagggccg agcgcagaag tggtcctgca actttatccg cctccatcca     240

gtctattaat tgttgccggg aagctagagt aagtagttcg ccagttaata gtttgcgcaa     300

cgttgttgcc attgctacag gcatcgtggt gtcacgctcg tcgtttggta tggcttcatt     360

cagctccggt tcccaacgat caaggcgagt tacatgatcc cccatgttgt gcaaaaaagc     420

ggttagctcc ttcggtcctc cgatcgttgt cagaagtaag ttggccgcag tgttatcact     480

catggttatg gcagcactgc ataattctct tactgtcatg ccatccgtaa gatgcttttc     540

tgtgactggt gagtactcaa ccaagtcatt ctgagaatag tgtatgcggc gaccgagttg     600

ctcttgcccg gcgtcaatac gggataatac cgcgccacat agcagaactt taaaagtgct     660

catcattgga aaacgttctt cggggcgaaa actctcaagg atcttaccgc tgttgagatc     720

cagttcgatg taacccactc gtgcacccaa ctgatcttca gcatctttta ctttcaccag     780

cgtttctggg tgagcaaaaa caggaaggca aaatgccgca aaaaagggaa taagggcgac     840

acggaaatgt tgaatactca t                                               861
```

<210> SEQ ID NO 57
<211> LENGTH: 7865
<212> TYPE: DNA
<213> ORGANISM: Artificial Sequence
<220> FEATURE:
<223> OTHER INFORMATION: Synthetic

<400> SEQUENCE: 57

```
tcgcgcgttt cggtgatgac ggtgaaaacc tctgacacat gcagctcccg gagacggtca      60
```

-continued

```
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cctcgagatt taaatgacgt    420
tggccactcc ctctctgcgc gctcgctcgc tcactgaggc cgggcgacca aaggtcgccc    480
gacgcccggg ctttgcccgg gcggcctcag tgagcgagcg agcgcgcaga gagggagtgg    540
ccaactccat cactaggggt tcctgagttt aaacttcgtc gacgggggag gctgctggtg    600
aatattaacc aaggtcaccc cagttatcgg aggagcaaac aggggctaag tccaccgggg    660
gaggctgctg gtgaatatta accaaggtca ccccagttat cggaggagca aacaggggct    720
aagtccacaa atgacctatt aagaatattt catagaacga atgttccgat gctctaatct    780
ctctagacaa ggttcatatt tgtatgggtt acttattctc tctttgttga ctaagtcaat    840
aatcagaatc agcaggtttg cagtcagatt ggcagggata agcagcctag ctcaggagaa    900
gtgagtataa aagccccagg ctgggagcag ccatcacaga agtccactca ttcttggcag    960
gggcgcgccg ccaccatgca gattgagctg agcacctgct tcttcctgtg cctgctgagg   1020
ttctgcttct ctgccaccag gagatactac ctgggggctg tggagctttc ttgggactac   1080
atgcagtctg acctgggga gctgcctgtg gatgccaggt tcccacccag agtgcccaaa   1140
tccttcccat tcaacacctc tgtggtctac aagaagaccc tctttgtgga gttcactgac   1200
cacctgttca acattgccaa acccaggcca ccctggatgg gactcctggg acccaccatt   1260
caggctgagg tgtatgacac tgtggtcgtc accctcaaga acatggcctc ccaccctgtg   1320
agcctgcatg ctgtgggggt cagctactgg aagtcctctg agggggctga gtatgatgac   1380
cagacctccc agagggagaa ggaggatgac aaagtgttcc ctgggaagag ccacacctat   1440
gtgtggcagg tcctcaagga gaatggcccc actgcctctg acccaccctg cctgacctac   1500
tcctaccttt ctcatgtgga cctggtcaag gacctcaact ctggactgat tggggccctg   1560
ctggtgtgca gggagggctc cctggccaaa gagaagaccc agaccctgca caagttcatt   1620
ctcctgtttg ctgtctttga tgagggcaag agctggcact ctgaaaccaa gaactccctg   1680
atgcaggaca gggatgctgc ctctgccagg gcctggccca agatgcacac tgtgaatggc   1740
tatgtgaaca ggagcctgcc tggactcatt ggctgccaca ggaaatctgt ctactggcat   1800
gtgattggca tggggacaac ccctgaggtg cactccattt tcctggaggg ccacaccttc   1860
ctggtcagga accacagaca ggccagcctg gagatcagcc ccatcacctt cctcactgcc   1920
cagaccctgc tgatggacct cggacagttc ctgctgttct gccacatcag ctcccaccag   1980
catgatggca tggaggccta tgtcaaggtg gacagctgcc ctgaggagcc acagctcagg   2040
atgaagaaca atgaggaggc tgaggactat gatgatgacc tgactgactc tgagatggat   2100
gtggtccgct ttgatgatga caacagccca tccttcattc agatcaggtc tgtggccaag   2160
aaacacccca agacctgggt gcactacatt gctgctgagg aggaggactg ggactatgcc   2220
ccactggtcc tggcccctga tgacaggagc tacaagagcc agtacctcaa caatggccca   2280
cagaggattg gacgcaagta caagaaagtc aggttcatgg cctacactga tgaaaccttc   2340
aagaccaggg aggccattca gcatgagtct ggcatcctgg gcccactcct gtatggggag   2400
```

```
gtgggggaca ccctgctcat catcttcaag aaccaggcct ccaggcccta caacatctac   2460
ccacatggca tcactgatgt caggcccctg tacagccgca ggctgccaaa gggggtgaaa   2520
cacctcaagg acttccccat tctgcctggg gagatcttca agtacaagtg gactgtcact   2580
gtggaggatg gaccaaccaa atctgacccc aggtgcctca ccagatacta ctccagcttt   2640
gtgaacatgg agagggacct ggcctctggc ctgattggcc cactgctcat ctgctacaag   2700
gagtctgtgg accagagggg aaaccagatc atgtctgaca agaggaatgt gattctgttc   2760
tctgtctttg atgagaacag gagctggtac ctgactgaga acattcagcg cttcctgccc   2820
aaccctgctg gggtgcagct ggaggaccct gagttccagg ccagcaacat catgcactcc   2880
atcaatggct atgtgtttga cagcctccag ctttctgtct gcctgcatga ggtggcctac   2940
tggtacattc tttctattgg ggcccagact gacttccttt ctgtcttctt ctctggctac   3000
accttcaaac acaagatggt gtatgaggac accctgaccc tcttcccatt ctctggggag   3060
actgtgttca tgagcatgga gaaccctggc ctgtggattc tgggatgcca caactctgac   3120
ttccgcaaca ggggcatgac tgccctgctc aaagtctcct cctgtgacaa gaacactggg   3180
gactactatg aggacagcta tgaggacatc tctgcctacc tgctcagcaa gaacaatgcc   3240
attgagccca ggagcttcag ccagaatgtg agcaataatg ccaccaaccc acctgtcctg   3300
aaacgccacc agagggagat caccaggacc accctccagt ctgaccagga ggagattgac   3360
tatgatgaca ccatttctgt ggagatgaag aaagaggact ttgacatcta tgacgaggac   3420
gagaaccaga gcccaaggag cttccagaag aagaccaggc actacttcat tgctgctgtg   3480
gagcgcctgt gggactatgg catgagctcc agcccccatg tcctcaggaa cagggcccag   3540
tctggctctg tgccacagtt caagaaagtg gtcttccaag agttcactga tggcagcttc   3600
acccagcccc tgtacagagg ggagctgaat gagcacctgg gactcctggg cccatacatc   3660
agggctgagg tggaggacaa catcatggtg accttccgca accaggcctc caggccctac   3720
agcttctaca gctccctcat cagctatgag gaggaccaga ggcagggggc tgagccacgc   3780
aagaactttg tgaaacccaa tgaaaccaag acctacttct ggaaagtcca gcaccacatg   3840
gcccccacca aggatgagtt tgactgcaag gcctgggcct acttctctga tgtggacctg   3900
gagaaggatg tgcactctgg cctgattggc ccactcctgg tctgccacac caacaccctg   3960
aaccctgccc atggaaggca agtgactgtg caggagtttg ccctcttctt caccatcttt   4020
gatgaaacca agagctggta cttcactgag aacatggagc gcaactgcag ggcccccatgc   4080
aacattcaga tggaggaccc caccttcaaa gagaactacc gcttccatgc catcaatggc   4140
tacatcatgg acaccctgcc tgggcttgtc atggcccagg accagaggat caggtggtac   4200
ctgctttcta tgggctccaa tgagaacatt cactccatcc acttctctgg gcatgtcttc   4260
actgtgcgca agaaggagga gtacaagatg gccctgtaca acctctaccc tggggtcttt   4320
gagactgtgg agatgctgcc ctccaaagct ggcatctgga gggtggagtg cctcattggg   4380
gagcacctgc atgctggcat gagcaccctg ttcctggtct acagcaacaa gtgccagacc   4440
cccctgggaa tggcctctgg ccacatcagg gacttccaga tcactgcctc tggccagtat   4500
ggccagtggg cccccaagct ggccaggctc cactactctg gatccatcaa tgcctggagc   4560
accaaggagc cattcagctg gatcaaagtg gacctgctgg cccccatgat catccatggc   4620
atcaagaccc agggggccag gcagaagttc tccagcctgt acatcagcca gttcatcatc   4680
atgtacagcc tggatggcaa gaaatggcag acctacagag gcaactccac tggaacactc   4740
atggtcttct ttggcaatgt ggacagctct ggcatcaagc acaacatctt caacccccca   4800
```

```
atcatcgcca gatacatcag gctgcacccc acccactaca gcatccgcag caccctcagg   4860
atggagctga tgggctgtga cctgaactcc tgcagcatgc ccctgggcat ggagagcaag   4920
gccatttctg atgcccagat cactgcctcc agctacttca ccaacatgtt tgccacctgg   4980
agcccaagca aggccaggct gcacctccag ggaaggagca atgcctggag gccccaggtc   5040
aacaacccaa aggagtggct gcaggtggac ttccagaaga ccatgaaggt cactggggtg   5100
accacccagg gggtcaagag cctgctcacc agcatgtatg tgaaggagtt cctgatcagc   5160
tccagccagg atggccacca gtggaccctc ttcttccaga atggcaaggt caaggtgttc   5220
cagggcaacc aggacagctt caccccctgtg gtgaacagcc tggacccccc cctcctgacc   5280
agatacctga ggattcaccc ccagagctgg gtccaccaga ttgccctgag gatggaggtc   5340
ctgggatgtg aggcccagga cctgtactga tgagcggccg ctcttagtag cagtatcgat   5400
aataaaagat ctttattttc attagatctg tgtgttggtt ttttgtgtgt taattaagct   5460
cgcgaaggaa cccctagtga tggagttggc cactccctct ctgcgcgctc gctcgctcac   5520
tgaggccggg cgaccaaagg tcgcccgacg cccgggcttt gcccgggcgg cctcagtgag   5580
cgagcgagcg cgcagagagg gagtggccaa gacgatttaa atgacaagct tggcgtaatc   5640
atggtcatag ctgtttcctg tgtgaaattg ttatccgctc acaattccac acaacatacg   5700
agccggaagc ataaagtgta aagcctgggg tgcctaatga gtgagctaac tcacattaat   5760
tgcgttgcgc tcactgcccg ctttccagtc gggaaacctg tcgtgccagc tgcattaatg   5820
aatcggccaa cgcgcgggga gaggcggttt gcgtattggg cgctcttccg cttcctcgct   5880
cactgactcg ctgcgctcgg tcgttcggct gcggcgagcg gtatcagctc actcaaaggc   5940
ggtaatacgg ttatccacag aatcagggga taacgcagga aagaacatgt gagcaaaagg   6000
ccagcaaaag gccaggaacc gtaaaaaggc cgcgttgctg gcgtttttcc ataggctccg   6060
cccccctgac gagcatcaca aaaatcgacg ctcaagtcag aggtggcgaa acccgacagg   6120
actataaaga taccaggcgt ttccccctgg aagctccctc gtgcgctctc ctgttccgac   6180
cctgccgctt accggatacc tgtccgcctt tctcccttcg ggaagcgtgg cgctttctca   6240
tagctcacgc tgtaggtatc tcagttcggt gtaggtcgtt cgctccaagc tgggctgtgt   6300
gcacgaaccc cccgttcagc ccgaccgctg cgccttatcc ggtaactatc gtcttgagtc   6360
caacccggta agacacgact tatcgccact ggcagcagcc actggtaaca ggattagcag   6420
agcgaggtat gtaggcggtg ctacagagtt cttgaagtgg tggcctaact acggctacac   6480
tagaagaaca gtatttggta tctgcgctct gctgaagcca gttaccttcg gaaaaagagt   6540
tggtagctct tgatccggca aacaaaccac cgctggtagc ggtggttttt ttgtttgcaa   6600
gcagcagatt acgcgcagaa aaaaaggatc tcaagaagat cctttgatct tttctacggg   6660
gtctgacgct cagtggaacg aaaactcacg ttaagggatt ttggtcatga gattatcaaa   6720
aaggatcttc acctagatcc ttttaaatta aaaatgaagt tttaaatcaa tctaaagtat   6780
atatgagtaa acttggtctg acagttacca atgcttaatc agtgaggcac ctatctcagc   6840
gatctgtcta tttcgttcat ccatagttgc ctgactcccc gtcgtgtaga taactacgat   6900
acgggagggc ttaccatctg gccccagtgc tgcaatgata ccgcgagacc cacgctcacc   6960
ggctccagat ttatcagcaa taaaccagcc agccggaagg gccgagcgca gaagtggtcc   7020
tgcaacttta tccgcctcca tccagtctat taattgttgc cgggaagcta gagtaagtag   7080
ttcgccagtt aatagtttgc gcaacgttgt tgccattgct acaggcatcg tggtgtcacg   7140
```

-continued

```
ctcgtcgttt ggtatggctt cattcagctc cggttcccaa cgatcaaggc gagttacatg   7200

atcccccatg ttgtgcaaaa aagcggttag ctccttcggt cctccgatcg ttgtcagaag   7260

taagttggcc gcagtgttat cactcatggt tatggcagca ctgcataatt ctcttactgt   7320

catgccatcc gtaagatgct tttctgtgac tggtgagtac tcaaccaagt cattctgaga   7380

atagtgtatg cggcgaccga gttgctcttg cccggcgtca atacgggata ataccgcgcc   7440

acatagcaga actttaaaag tgctcatcat tggaaaacgt tcttcggggc gaaaactctc   7500

aaggatctta ccgctgttga gatccagttc gatgtaaccc actcgtgcac ccaactgatc   7560

ttcagcatct tttactttca ccagcgtttc tgggtgagca aaaacaggaa ggcaaaatgc   7620

cgcaaaaaag ggaataaggg cgacacggaa atgttgaata ctcatactct tcctttttca   7680

atattattga agcatttatc agggttattg tctcatgagc ggatacatat ttgaatgtat   7740

ttagaaaaat aaacaaatag gggttccgcg cacatttccc cgaaaagtgc cacctgacgt   7800

ctaagaaacc attattatca tgacattaac ctataaaaat aggcgtatca cgaggccctt   7860

tcgtc                                                                7865
```

VIRAL VECTORS ENCODING RECOMBINANT FVIII VARIANTS WITH INCREASED EXPRESSION FOR GENE THERAPY OF HEMOPHILIA A

CROSS REFERENCE TO RELATED APPLICATION

This application claims priority to U.S. Provisional Patent Application No. 62/793,058, filed Jan. 16, 2019, the disclosure of which is hereby incorporated by reference herein in its entirety for all purposes.

SEQUENCE LISTING

The instant application contains a Sequence Listing which has been submitted electronically in ASCII format and is hereby incorporated by reference in its entirety. Said ASCII copy, created on Apr. 13, 2020, titled 008073-5191-US_Sequence.txt and is 91,312 kilobytes in size.

BACKGROUND OF THE DISCLOSURE

Blood coagulation proceeds through a complex and dynamic biological pathway of interdependent biochemical reactions, referred to as the coagulation cascade. Coagulation Factor VIII (FVIII) is a key component in the cascade. Factor VIII is recruited to bleeding sites, and forms a Xase complex with activated Factor IX (FIXa) and Factor X (FX). The Xase complex activates FX, which in turn activates prothrombin to thrombin, which then activates other components in the coagulation cascade to generate a stable clot (reviewed in Saenko et al., Trends Cardiovasc. Med., 9:185-92 (1999); Lenting et al., Blood, 92:3983-96 (1998)).

Hemophilia A is a congenital X-linked bleeding disorder characterized by a deficiency in Factor VIII activity. Diminished Factor VIII activity inhibits a positive feedback loop in the coagulation cascade. This causes incomplete coagulation, which manifests as bleeding episodes with increased duration, extensive bruising, spontaneous oral and nasal bleeding, joint stiffness and chronic pain, and possibly internal bleeding and anemia in severe cases (Zhang et al., Clinic. Rev. Allerg. Immunol., 37:114-24 (2009)).

Conventionally, hemophilia A is treated by Factor VIII replacement therapy, which consists of administering Factor VIII protein (e.g., plasma-derived or recombinantly-produced Factor VIII) to an individual with hemophilia A. Factor VIII is administered prophylactically to prevent or reduce frequency of bleeding episodes, in response to an acute bleeding episode, and/or perioperatively to manage bleeding during surgery. However, there are several undesirable features of Factor VIII replacement therapy.

First, Factor VIII replacement therapy is used to treat or manage hemophilia A, but does not cure the underlying Factor VIII deficiency. Because of this, individuals with hemophilia A require Factor VIII replacement therapy for the duration of their lives. Continuous treatment is expensive and requires the individual to maintain strict compliance, as missing only a few prophylactic doses can have serious consequences for individuals with severe hemophilia A.

Second, because Factor VIII has a relatively short half-life in vivo, conventional prophylactic Factor VIII replacement therapy requires administration every second or third day. This places a burden on the individual to maintain compliance throughout their life. While third generation “long-acting” Factor VIII drugs may reduce the frequency of administration, prophylactic Factor FVIII replacement therapy with these drugs still requires monthly, weekly, or more frequent administration in perpetuity. For example, prophylactic treatment with ELOCTATE™ [Antihemophilic Factor (Recombinant), Fc Fusion Protein] requires administration every three to five days (ELOCTATE™ Prescribing Information, Biogen Idec Inc., (2015)). Moreover, the long-term effects of chemically modified biologics (e.g., pegylated polypeptides) are not yet fully understood.

Third, between 15% and 30% of all individuals receiving Factor VIII replacement therapy form anti-Factor VIII inhibitor antibodies, rendering the therapy inefficient. Factor VIII bypass therapy (e.g., administration of plasma-derived or recombinantly-produced prothrombin complex concentrates) can be used to treat hemophilia in individuals that form inhibitor antibodies. However, Factor VIII bypass therapy is less effective than Factor VIII replacement therapy (Mannucci P. M., J Thromb Haemost., 1(7):1349-55 (2003)) and may be associated with an increased risk of cardiovascular complication (Luu and Ewenstein, Haemophilia, 10 Suppl. 2:10-16 (2004)).

Somatic gene therapy holds great promise for the treatment of hemophilia A because it would remedy the underlying under-expression functional Factor VIII activity (e.g., due to missense or nonsense mutations), rather than provide a one-time dose of Factor VIII activity to the individual. Because of this difference in the mechanism of action, as compared to Factor VIII replacement therapy, one-time administration of a Factor VIII gene therapy vector may provide an individual with Factor VIII for several years, reducing the cost of treatment and eliminating the need for continued patient compliance.

Coagulation Factor IX (FIX) gene therapy has been used effectively to treat individuals with hemophilia B, a related blood coagulation condition characterized by diminished Factor IX activity (Manno C. S., et al., Nat Med., 12(3): 342-47 (2006)). However, Factor VIII gene therapy presents several unique challenges. For example, the full-length, wild-type Factor VIII polypeptide (2351 amino acids; UniProt accession number P00451) is five times larger than the full-length, wild-type Factor IX polypeptide (461 amino acids; UniProt accession number P00740). As such, the coding sequence of wild-type Factor VIII is 7053 base pairs, which is too large to be packaged in conventional AAV gene therapy vectors. Further, reported recombinant expression of B-domain deleted variants of Factor VIII (BDD-FVIII) has been poor. As such, several groups have attempted to alter the codon usage of BDD-FVIII constructs, with limited success.

BRIEF SUMMARY OF DISCLOSURE

Accordingly, there is a need for Factor VIII variants whose coding sequences are more efficiently packaged into, and delivered via, gene therapy vectors. There is also a need for synthetic, codon-altered nucleic acids which express Factor VIII more efficiently. There is also a need for codon-altered nucleic acids encoding Factor VIII polypeptides with improved folding properties, improved secretion from expressing cells, increased activity, and/or improved circulating half-life in vivo, as compared to wild-type Factor VIII or wild-type B-domain deleted Factor VIII. Such Factor VIII variants and codon-altered nucleic acids allow for improved treatment of Factor VIII deficiencies (e.g., hemophilia A). The above deficiencies and other problems associated with the treatment of Factor VIII deficiencies (e.g., hemophilia A) are reduced or eliminated by the disclosed codon-altered Factor VIII variants.

In one aspect, nucleic acid compositions (e.g., codon-altered polynucleotides) encoding Factor VIII variants are described. In some embodiments, the nucleic acid compositions include polynucleotides with high sequence identity to the CS04 (SEQ ID NO:37) or CS12 (SEQ ID NO:1) sequences encoding Factor VIII variants, as described herein. In some embodiments, the nucleic acid compositions described herein provide increased Factor VIII expression and/or increased Factor VIII activity in the blood of an animal relative to wild-type Factor VIII coding sequences and/or other codon-optimized Factor VIII coding sequences. In some embodiments, the nucleic acid compositions also allow for increased production of AAV-based gene therapy virions. In some embodiments, the nucleic acid compositions described herein have decreased GC content and or include fewer CpG dinucleotides, as compared to wild-type sequences encoding Factor VIII. In some embodiments, the Factor VIII variant encoded by the nucleic acid compositions is secreted into the blood more effectively, in vivo, and/or has an increased circulating half-life in the blood, in vivo, relative to wild-type Factor VIII and/or other Factor VIII variants.

In some embodiments, a nucleic acid composition includes a polynucleotide encoding a Factor VIII polypeptide having an amino acid sequence of CS12-FL-AA (SEQ ID NO:2), where the polynucleotide has a sequence with at least 95% sequence identity (e.g., at least 95%, 96%, 97%, 98%, 99%, 99.5%, or 100% sequence identity) to a CS12-FL-NA (SEQ ID NO:1).

In some embodiments, the nucleic acid composition further includes a promoter polynucleotide operatively linked to the Factor VIII polynucleotide, wherein the promoter polynucleotide has a nucleic acid sequence with at least 90% sequence identity (e.g., at least 90%, 91%, 92%, 93%, 94%, 95%, 96%, 97%, 98%, 99%, 99.5%, or 100%) to hTTR (SEQ ID NO:6). In some embodiments, the promoter is directly attached to the Factor VIII polynucleotide, e.g., as depicted in FIG. 11.

In some embodiments, the nucleic acid composition further includes a liver-specific element operatively linked to the Factor VIII polynucleotide. In some embodiments, the liver-specific element is an enhancer element with at least 90% sequence identity (e.g., at least 90%, 91%, 92%, 93%, 94%, 95%, 96%, 97%, 98%, or 100%) to CRM8 (SEQ ID NO:5). In some embodiments, the nucleic acid composition includes two such liver-specific elements operatively linked to the Factor VIII polynucleotide. In some embodiments, the nucleic acid composition includes three such liver-specific elements operatively linked to the Factor VIII polynucleotide. In some embodiments, the one or more liver-specific elements and the promoter are directly attached, e.g., as depicted in FIG. 11.

In some embodiments, the nucleic acid composition has a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vr (SEQ ID NO:3).

In some embodiments, the acid composition has a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vrp (SEQ ID NO:10).

In one aspect, mammalian gene therapy vectors that include a nucleic acid that encodes a Factor VIII variant are described. In some embodiments, the nucleic acid that encodes the Factor VIII includes a polynucleotide with high sequence identity to the CS04 (SEQ ID NO:37) or CS12 (SEQ ID NO:1) sequences encoding Factor VIII variants, as described herein. In some embodiments, the mammalian gene therapy vectors described herein provide increased Factor VIII expression and/or increased Factor VIII activity in the blood of an animal relative to gene therapy vectors that include a natively encoded Factor VIII variant polynucleotide or other codon-optimized Factor VIII variant polynucleotides. In some embodiments, the mammalian gene therapy vectors described herein encode for a Factor VIII variant protein that is secreted into the blood more effectively, in vivo, and/or has an increased circulating half-life in the blood, in vivo, relative to wild-type Factor VIII and/or other Factor VIII variants.

In some embodiments, the mammalian gene therapy vector includes a polynucleotide encoding a Factor VIII polypeptide having an amino acid sequence of CS12-FL-AA (SEQ ID NO:2), where the polynucleotide has a sequence with at least 95% sequence identity (e.g., at least 95%, 96%, 97%, 98%, 99%, 99.5%, or 100% sequence identity) to a CS12-FL-NA (SEQ ID NO:1).

In some embodiments, the mammalian gene therapy vector further includes a promoter polynucleotide operatively linked to the Factor VIII polynucleotide, wherein the promoter polynucleotide has a nucleic acid sequence with at least 90% sequence identity (e.g., at least 90%, 91%, 92%, 93%, 94%, 95%, 96%, 97%, 98%, 99%, 99.5%, or 100%) to hTTR (SEQ ID NO:6). In some embodiments, the promoter is directly attached to the Factor VIII polynucleotide, e.g., as depicted in FIG. 11.

In some embodiments, the mammalian gene therapy vector further includes a liver-specific element operatively linked to the Factor VIII polynucleotide. In some embodiments, the liver-specific element is an enhancer element with at least 90% sequence identity (e.g., at least 90%, 91%, 92%, 93%, 94%, 95%, 96%, 97%, 98%, or 100%) to CRM8 (SEQ ID NO:5). In some embodiments, the nucleic acid composition includes two such liver-specific elements operatively linked to the Factor VIII polynucleotide. In some embodiments, the nucleic acid composition includes three such liver-specific elements operatively linked to the Factor VIII polynucleotide. In some embodiments, the one or more liver-specific elements and the promoter are directly attached, e.g., as depicted in FIG. 11.

In some embodiments, the mammalian gene therapy vector has a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vr (SEQ ID NO:3).

In some embodiments, the mammalian gene therapy vector is included in a plasmid having a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vrp (SEQ ID NO:10).

In one aspect, adeno-associated virus (AAV) particles that include a nucleic acid that encodes a Factor VIII variant are described. In some embodiments, the nucleic acid that encodes the Factor VIII includes a polynucleotide with high sequence identity to the CS04 (SEQ ID NO:37) or CS12 (SEQ ID NO:1) sequences encoding Factor VIII variants, as described herein. In some embodiments, the AAV particles described herein provide increased Factor VIII expression and/or increased Factor VIII activity in the blood of an animal relative to AAV particles that include a natively encoded Factor VIII variant polynucleotide or other codon-optimized Factor VIII variant polynucleotides. In some embodiments, the AAV particles described herein encode for a Factor VIII variant protein that is secreted into the blood more effectively, in vivo, and/or has an increased circulating half-life in the blood, in vivo, relative to wild-type Factor VIII and/or other Factor VIII variants.

In some embodiments, the nucleic acid contained in the AAV particles includes a polynucleotide encoding a Factor VIII polypeptide having an amino acid sequence of CS12-FL-AA (SEQ ID NO:2), where the polynucleotide has a sequence with at least 95% sequence identity (e.g., at least 95%, 96%, 97%, 98%, 99%, 99.5%, or 100% sequence identity) to a CS12-FL-NA (SEQ ID NO:1).

In some embodiments, the nucleic acid contained in the AAV particles further includes a promoter polynucleotide operatively linked to the Factor VIII polynucleotide, wherein the promoter polynucleotide has a nucleic acid sequence with at least 90% sequence identity (e.g., at least 90%, 91%, 92%, 93%, 94%, 95%, 96%, 97%, 98%, 99%, 99.5%, or 100%) to hTTR (SEQ ID NO:6). In some embodiments, the promoter is directly attached to the Factor VIII polynucleotide, e.g., as depicted in FIG. 11.

In some embodiments, the nucleic acid contained in the AAV particles further includes a liver-specific element operatively linked to the Factor VIII polynucleotide. In some embodiments, the liver-specific element is an enhancer element with at least 90% sequence identity (e.g., at least 90%, 91%, 92%, 93%, 94%, 95%, 96%, 97%, 98%, or 100%) to CRM8 (SEQ ID NO:5). In some embodiments, the nucleic acid composition includes two such liver-specific elements operatively linked to the Factor VIII polynucleotide. In some embodiments, the nucleic acid composition includes three such liver-specific elements operatively linked to the Factor VIII polynucleotide. In some embodiments, the one or more liver-specific elements and the promoter are directly attached, e.g., as depicted in FIG. 11.

In some embodiments, the nucleic acid contained in the AAV particles has a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vr (SEQ ID NO:3).

In some embodiments, the nucleic acid contained in the AAV particles is produced using a plasmid having a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vrp (SEQ ID NO:10).

In one aspect, methods for treating hemophilia A by administering a nucleic acid composition that encodes a Factor VIII variant to a patient with hemophilia A are described. In some embodiments, the nucleic acid composition includes a polynucleotide with high sequence identity to the CS04 (SEQ ID NO:37) or CS12 (SEQ ID NO:1) sequences encoding Factor VIII variants, as described herein. In some embodiments, the methods for treating hemophilia A described herein result in increases in Factor VIII expression and/or increases in Factor VIII activity in the blood of the patient that are greater than increases in Factor VIII expression and/or increases in Factor VIII activity in the blood of a patient administered a nucleic acid composition that includes a wild type Factor VIII coding sequence and/or a different codon-optimized Factor VIII coding sequence. In some embodiments, the Factor VIII variant encoded by the nucleic acid composition is secreted into the blood more effectively, in vivo, and/or has an increased circulating half-life in the blood, in vivo, relative to wild-type Factor VIII and/or other Factor VIII variants.

In some embodiments, the administered nucleic acid composition includes a polynucleotide encoding a Factor VIII polypeptide having an amino acid sequence of CS12-FL-AA (SEQ ID NO:2), where the polynucleotide has a sequence with at least 95% sequence identity (e.g., at least 95%, 96%, 97%, 98%, 99%, 99.5%, or 100% sequence identity) to a CS12-FL-NA (SEQ ID NO:1).

In some embodiments, the administered nucleic acid composition further includes a promoter polynucleotide operatively linked to the Factor VIII polynucleotide, wherein the promoter polynucleotide has a nucleic acid sequence with at least 90% sequence identity (e.g., at least 90%, 91%, 92%, 93%, 94%, 95%, 96%, 97%, 98%, 99%, 99.5%, or 100%) to hTTR (SEQ ID NO:6). In some embodiments, the promoter is directly attached to the Factor VIII polynucleotide, e.g., as depicted in FIG. 11.

In some embodiments, the administered nucleic acid composition further includes a liver-specific element operatively linked to the Factor VIII polynucleotide. In some embodiments, the liver-specific element is an enhancer element with at least 90% sequence identity (e.g., at least 90%, 91%, 92%, 93%, 94%, 95%, 96%, 97%, 98%, or 100%) to CRM8 (SEQ ID NO:5). In some embodiments, the nucleic acid composition includes two such liver-specific elements operatively linked to the Factor VIII polynucleotide. In some embodiments, the nucleic acid composition includes three such liver-specific elements operatively linked to the Factor VIII polynucleotide. In some embodiments, the one or more liver-specific elements and the promoter are directly attached, e.g., as depicted in FIG. 11.

In some embodiments, the administered nucleic acid composition has a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vr (SEQ ID NO:3).

In some embodiments, the administered nucleic acid composition has a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vrp (SEQ ID NO:10).

In one aspect, methods for treating hemophilia A by administering a mammalian gene therapy vector that includes a nucleic acid encoding a Factor VIII variant are described. In some embodiments, the nucleic acid that encodes the Factor VIII includes a polynucleotide with high sequence identity to the CS04 (SEQ ID NO:37) or CS12 (SEQ ID NO:1) sequences encoding Factor VIII variants, as described herein. In some embodiments, the methods for treating hemophilia A described herein result in increases in Factor VIII expression and/or increases in Factor VIII activity in the blood of the patient that are greater than increases in Factor VIII expression and/or increases in Factor VIII activity in the blood of a patient administered a mammalian gene therapy vector that includes a wild type Factor VIII coding sequence and/or a different codon-optimized Factor VIII coding sequence. In some embodiments, the Factor VIII variant encoded by the nucleic acid within the mammalian gene therapy vector is secreted into the blood more effectively, in vivo, and/or has an increased circulating half-life in the blood, in vivo, relative to wild-type Factor VIII and/or other Factor VIII variants.

In some embodiments, the administered mammalian gene therapy vector includes a polynucleotide encoding a Factor VIII polypeptide having an amino acid sequence of CS12-FL-AA (SEQ ID NO:2), where the polynucleotide has a sequence with at least 95% sequence identity (e.g., at least 95%, 96%, 97%, 98%, 99%, 99.5%, or 100% sequence identity) to a CS12-FL-NA (SEQ ID NO:1).

In some embodiments, the administered mammalian gene therapy vector further includes a promoter polynucleotide operatively linked to the Factor VIII polynucleotide, wherein the promoter polynucleotide has a nucleic acid sequence with at least 90% sequence identity (e.g., at least 90%, 91%, 92%, 93%, 94%, 95%, 96%, 97%, 98%, 99%, 99.5%, or 100%) to hTTR (SEQ ID NO:6). In some embodiments, the promoter is directly attached to the Factor VIII polynucleotide, e.g., as depicted in FIG. 11.

In some embodiments, the administered mammalian gene therapy vector further includes a liver-specific element operatively linked to the Factor VIII polynucleotide. In some embodiments, the liver-specific element is an enhancer element with at least 90% sequence identity (e.g., at least 90%, 91%, 92%, 93%, 94%, 95%, 96%, 97%, 98%, or 100%) to CRM8 (SEQ ID NO:5). In some embodiments, the nucleic acid composition includes two such liver-specific elements operatively linked to the Factor VIII polynucleotide. In some embodiments, the nucleic acid composition includes three such liver-specific elements operatively linked to the Factor VIII polynucleotide. In some embodiments, the one or more liver-specific elements and the promoter are directly attached, e.g., as depicted in FIG. 11.

In some embodiments, the administered mammalian gene therapy vector has a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vr (SEQ ID NO:3).

In some embodiments, the administered mammalian gene therapy vector is included in a plasmid having a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vrp (SEQ ID NO:10).

In one aspect, methods for treating hemophilia A by administering an adeno-associated virus (AAV) particle that includes a nucleic acid encoding a Factor VIII variant are described. In some embodiments, the nucleic acid that encodes the Factor VIII includes a polynucleotide with high sequence identity to the CS04 (SEQ ID NO:37) or CS12 (SEQ ID NO:1) sequences encoding Factor VIII variants, as described herein. In some embodiments, the methods for treating hemophilia A described herein result in increases in Factor VIII expression and/or increases in Factor VIII activity in the blood of the patient that are greater than increases in Factor VIII expression and/or increases in Factor VIII activity in the blood of a patient administered an adeno-associated virus (AAV) particle that includes a wild type Factor VIII coding sequence and/or a different codon-optimized Factor VIII coding sequence. In some embodiments, the Factor VIII variant encoded by the nucleic acid within the adeno-associated virus (AAV) particle is secreted into the blood more effectively, in vivo, and/or has an increased circulating half-life in the blood, in vivo, relative to wild-type Factor VIII and/or other Factor VIII variants.

In some embodiments, the nucleic acid contained in the administered AAV particles includes a polynucleotide encoding a Factor VIII polypeptide having an amino acid sequence of CS12-FL-AA (SEQ ID NO:2), where the polynucleotide has a sequence with at least 95% sequence identity (e.g., at least 95%, 96%, 97%, 98%, 99%, 99.5%, or 100% sequence identity) to a CS12-FL-NA (SEQ ID NO:1).

In some embodiments, the nucleic acid contained in the administered AAV particles further includes a promoter polynucleotide operatively linked to the Factor VIII polynucleotide, wherein the promoter polynucleotide has a nucleic acid sequence with at least 90% sequence identity (e.g., at least 90%, 91%, 92%, 93%, 94%, 95%, 96%, 97%, 98%, 99%, 99.5%, or 100%) to hTTR (SEQ ID NO:6). In some embodiments, the promoter is directly attached to the Factor VIII polynucleotide, e.g., as depicted in FIG. 11.

In some embodiments, the nucleic acid contained in the administered AAV particles further includes a liver-specific element operatively linked to the Factor VIII polynucleotide. In some embodiments, the liver-specific element is an enhancer element with at least 90% sequence identity (e.g., at least 90%, 91%, 92%, 93%, 94%, 95%, 96%, 97%, 98%, or 100%) to CRM8 (SEQ ID NO:5). In some embodiments, the nucleic acid composition includes two such liver-specific elements operatively linked to the Factor VIII polynucleotide. In some embodiments, the nucleic acid composition includes three such liver-specific elements operatively linked to the Factor VIII polynucleotide. In some embodiments, the one or more liver-specific elements and the promoter are directly attached, e.g., as depicted in FIG. 11.

In some embodiments, the nucleic acid contained in the administered AAV particles has a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vr (SEQ ID NO:3).

In some embodiments, the nucleic acid contained in the administered AAV particles is produced using a plasmid having a nucleic acid sequence with at least 90% sequence identity (e.g., at least 90%, 91%, 92%, 93%, 94%, 95%, 96%, 97%, 98%, 99%, 99.5%, or 100%) to CS12-CRM8.2-Vrp (SEQ ID NO:10).

BRIEF DESCRIPTION OF DRAWINGS

FIGS. 1A and 1B collectively show the CS12 codon-optimized nucleotide sequence (SEQ ID NO:1) encoding a Factor VIII variant in accordance with some embodiments ("CS12-FL-NA" for full-length coding sequence).

FIG. 2 shows the Factor VIII variant amino acid sequence (SEQ ID NO: 2) encoded by the CS12 codon-altered nucleotide sequence in accordance with some embodiments ("CS12-FL-AA" for full-length amino acid sequence).

FIGS. 3A and 3B collectively show the nucleic acid sequence (SEQ ID NO:3) of the CS12-CRM8.2-Vr nucleotide-reduced gene therapy vector encoding a Factor VIII variant in accordance with some embodiments.

FIG. 4 shows the nucleic acid sequence of various genetic elements useful for gene therapy vectors encoding a Factor VIII variant, including a 5'-ITR (SEQ ID NO:4), a CRM8 enhancer element (SEQ ID NO:5), a human TTR promoter (SEQ ID NO:6), a minimal Kozak sequence (SEQ ID NO:7), and synthetic poly-adenylation element (SEQ ID NO:8), and a 3'-ITR (SEQ ID NO:9), in accordance with some embodiments.

FIGS. 5A, 5B, and 5C collectively show the nucleic acid sequence (SEQ ID NO:10) of the CS12-CRM8.2-Vrp plasmid containing a gene therapy vector encoding a Factor VIII variant in accordance with some embodiments.

FIGS. 6A and 6B collectively show the nucleic acid sequence (SEQ ID NO:38) of the CS12-CRM8.2-V gene therapy vector encoding a Factor VIII variant in accordance with some embodiments.

FIGS. 7A and 7B collectively show the CS04 codon-optimized nucleotide sequence (SEQ ID NO:37) encoding a Factor VIII variant in accordance with some embodiments ("CS12-FL-NA" for full-length coding sequence).

FIGS. 8A and 8B collectively show amino acid and nucleotide sequences for exemplary glycosylation peptides that are inserted into the B-domain substituted linker of a Factor VIII variant in accordance with some embodiments. "NG1" or NG1-AA" is the code for the amino acid sequence, shown in the top line. "NG1-NA" is the code for the nucleic acid sequence, shown in the bottom line for each set. FIGS. 8A and 8B disclose the amino acid sequences as SEQ ID NOS 11, 13, 15, 17, 19, 21, 23, 25, 27, 29, 31, 33, and 35, and the nucleotide sequences as SEQ ID NOS 12, 14, 16, 18, 20, 22, 24, 26, 28, 30, 32, 34, and 36 all, respectively, in order of appearance.

FIG. 12 shows Factor VIII activity levels in vivo in a "line E" hFVIII tolerant mouse model, and in vitro using HepG2 cells, post-infection with AAV8 gene therapy vectors encoding a Factor VIII variant protein in accordance with some embodiments.

FIG. 14 shows Factor VIII activity levels in vivo in a FVIII F17 knock-in mouse model, and in vitro using HepG2 cells, a human liver cell line (ATCC #HB-8065), post-infection with AAV8 gene therapy vectors encoding a Factor VIII variant protein in accordance with some embodiments.

FIG. 15 shows schematic illustrations of the wild-type and Refacto-type human Factor VIII protein constructs, as well as the Factor VIII protein encoded by the CS12 polynucleotide, which contains the X5 mutations and NG5 glycosylation peptide.

FIG. 16 shows a wild-type human Factor VIII amino acid sequence (SEQ ID NO:39), in accordance with some embodiments ("FVIII-FL-AA").

FIG. 17 shows example coding sequences (SEQ ID NOS 41-53, respectively, in order of appearance) for B-domain substituted linkers in accordance with some embodiments. BDLO04 (SEQ ID NO:41) is the portion of the CS04 codon-altered nucleotide sequences that encodes the B-domain substituted linker.

FIG. 18 shows an example plasmid backbone (SEQ ID NO:54) for integrating a Factor VIII gene therapy genome, in accordance with some embodiments.

FIG. 19 shows an example replicon ("pNMB1 Replicon"—SEQ ID NO:55) and ampicillin resistance marker ("Bla(ApR)"—SEQ ID NO:56) for a plasmid useful for integrating a Factor VIII gene therapy genome, in accordance with some embodiments.

FIGS. 20A, 20B, and 20C collectively show the nucleic acid sequence (SEQ ID NO:57) of the CS12-CRM8.2-Vp plasmid containing a gene therapy vector encoding a Factor VIII variant in accordance with some embodiments.

DETAILED DESCRIPTION OF DISCLOSURE

I. Introduction

Figure 9:
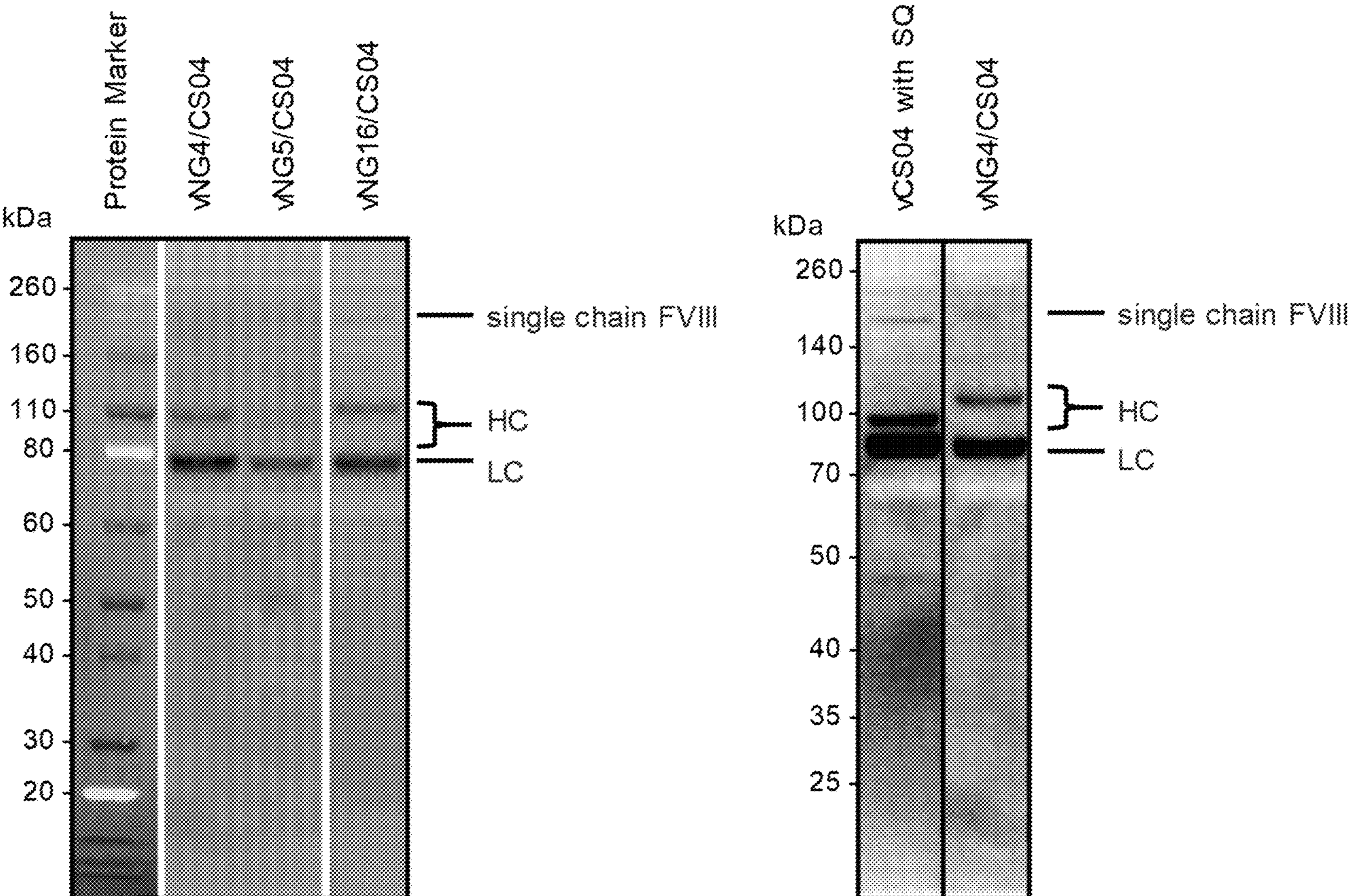
FIG. 9 shows western blot analysis of Factor VIII variants, with (vNG4/CS04, vNG5/CS04, and vNG16/CS04) and without (vCS04 with SQ) glycosylation peptides engineered into the SQ linker, expressed in Huh-7 cells.

AAV-based gene therapy holds great promise for the treatment of hemophiliacs. For hemophilia B, first clinical data are encouraging in that FIX levels of about 10% can be maintained in at least some patients for more than 1 year. For hemophilia A however, achieving therapeutic expression levels of 5-10% with AAV vectors remains challenging for various reasons. First, the Factor VIII coding sequence is too large for conventional AAV-based vectors. Second, engineered B-domain deleted or truncated Factor VIII constructs suffer from poor expression in vivo, even when codon-optimized. Third, these B-domain deleted or truncated Factor VIII variant constructs have short half-lives in vivo, exacerbating the effects of poor expression. Fourth, even when expressed, FVIII is not efficiently secreted from cells, as are other coagulation factors, such as Factor IX.

The present disclosure relates, in part, to the discovery of gene therapy vectors containing codon-altered Factor VIII variant coding sequences that solve these and other problems associated with Factor VIII gene therapy. For example, in some embodiments, the Factor VIII variant polynucleotides, polypeptides, and gene therapy constructs disclosed herein provide improved exogenous Factor VIII expression in mammalian cells. In some embodiments, the Factor VIII variant polynucleotides, polypeptides, and gene therapy constructs disclosed herein provide improved bioavailability (e.g., result in improved Factor VIII activity in the blood of a patient) in vivo. In some embodiments, the Factor VIII variant polynucleotides, polypeptides, and gene therapy constructs disclosed herein provide improved circulating half-life for exogenous Factor VIII in the blood of a patient. As described herein, one or more of these advantages are realized by using any combination of one or more of the following improvements to the gene therapy system.

In some implementations, one or more of these advantages are realized by engineering the X5 mutations into a Factor VIII variant polypeptide that is encoded by a codon-altered Factor VIII polypeptide, as described herein. Advantageously, inclusion of the X5 mutations in an encoded Factor VIII polypeptide, as described herein, provides improved biopotency of exogenously expressed Factor VIII, in vivo and in vitro. For instance, as described in Example 4, inclusion of the five X5 mutations in the A1 domain of the heavy chain of a Refacto FVIII polypeptide increased in vivo exogenous Factor VIII biopotency in line E2 mice by 3-fold following administration of an AAV gene therapy vector encoding the Refacto Factor VIII-X5 variant, as compared to mice administered an otherwise identical gene therapy vector encoding a wild type Refacto Factor VIII variant (compare vX5/CS24 to vCS04 in FIG. 12). Consistent with the in vivo results, inclusion of the five X5 mutations in the A1 domain of the Factor VIII heavy chain increased in vitro exogenous Factor VIII biopotency by 4-fold following infection of HepG2 cells with an AAV gene therapy vector encoding a Refacto Factor VIII-X5 variant, as compared to HepG2 cells infected with an otherwise identical gene therapy vector encoding a wild type Refacto Factor VIII variant (compare vX5/CS24 to vCS04 in FIG. 12).

In some implementations, one or more of these advantages are realized by engineering an NG5 glycosylation peptide into a B-domain linker of a Factor VIII variant polypeptide that is encoded by a codon-altered Factor VIII polypeptide, as described herein. Advantageously, inclusion of the NG5 glycosylation peptide in an encoded Factor VIII polypeptide, as described herein, provides improved biopotency of exogenously expressed Factor VIII, in vivo. For instance, as described in Example 3, inclusion of the NG glycosylation peptide in the SQ-linker of a Refacto FVIII polypeptide increased in vivo exogenous Factor VIII biopotency in line E2 mice by 2-fold following administration of an AAV gene therapy vector encoding the Refacto Factor VIII-NG5 variant, as compared to mice administered an otherwise identical gene therapy vector encoding a wild type Refacto Factor VIII variant (compare vNG5/CS04 to vCS04 in FIG. 12).

In some implementations, one or more of these advantages are realized by engineering both the X5 mutations and the NG5 glycosylation peptide into a Factor VIII variant polypeptide that is encoded by a codon-altered Factor VIII polypeptide, as described herein. Advantageously, inclusion of the X5 mutations and NG5 glycosylation peptide in an encoded Factor VIII polypeptide, as described herein, provides improved biopotency of exogenously expressed Factor VIII, in vivo and in vitro. For instance, as described in Example 5, inclusion of the five X5 mutations in the A1 domain of the heavy chain and the NG5 glycosylation peptide in the SQ-linker of a Refacto FVIII polypeptide increased in vivo exogenous Factor VIII biopotency in line E2 mice by 4.5-fold following administration of an AAV gene therapy vector encoding the Refacto Factor VIII-X5/NG5 variant, as compared to mice administered an otherwise identical gene therapy vector encoding a wild type Refacto Factor VIII variant (compare vX5/NG5/CS125 to vCS04 in FIG. 12). Consistent with the in vivo results, inclusion of the five X5 mutations in the A1 domain of the heavy chain and the NG5 glycosylation peptide in the SQ-linker of a Refacto FVIII polypeptide increased in vitro exogenous Factor VIII biopotency by 3-fold following infection of HepG2 cells with an AAV gene therapy vector encoding a Refacto Factor VIII-X5/NG5 variant, as compared to HepG2 cells infected with an otherwise identical gene therapy vector encoding a wild type Refacto Factor VIII variant (compare vX5/NG5/CS125 to vCS04 in FIG. 12).

In some implementations, one or more of these advantages are realized by using a human hTTR promoter and one or more liver-specific CRM8 elements upstream of the polynucleotide sequence encoding a Factor VIII variant polypeptide. Advantageously, use of the hTTR promoter and one or more liver-specific CRM8 elements provides improved biopotency of exogenously expressed Factor VIII in human cells, in vitro. For instance, as described in Example 2, use of the hTTR promoter and either one or two liver-specific CRM8 elements increased in vivo exogenous Factor VIII biopotency in HepG2 cells by about 2-fold and 4-fold, respectively, as compared to use of mouse TTR promoter and enhancer sequences (compare vCS115 and vCS116 to vCS04 in FIG. 12).

In some implementations, one or more of these advantages are realized by removing extraneous nucleotides positioned between various elements of an AAV gene therapy vector encoding a Factor VIII variant protein. Advantageously, removing extraneous nucleotides between various elements provides improved biopotency of exogenously expressed Factor VIII in human cells, in vitro. For instance, as described in Example 6, removal of only 71 nucleotides from the vX5/NG5/CS120 AAV gene therapy vector encoding a Refacto Factor VIII-X5/NG5 variant improved the in vitro biopotency of the expressed Factor VIII variant by 50% (compare vX5/NG5/CS12 to vX5/NG5/CS120 in FIG. 14).

In some implementations, one or more of these advantages are realized by engineering both the X5 mutations and the NG5 glycosylation peptide into a Factor VIII variant polypeptide that is encoded by a codon-altered Factor VIII polypeptide, and using a human hTTR promoter and one or more liver-specific CRM8 elements upstream of the polynucleotide sequence encoding the Factor VIII variant polypeptide. Advantageously, using this combination of improvements provides improved biopotency of exogenously expressed Factor VIII, in vivo and in vitro. For instance, as described in Example 6, use of this combination of improvements in an AAV gene therapy vector increased in vivo biopotency 14.5-fold, relative to use of an AAV gene therapy vector that includes a polynucleotide having the same codon-alteration for an encoded wild-type Refacto Factor VIII using murine TTR promoter and enhancer sequences (compare vX5/NG5/CS120 to vSC04 in FIG. 14). Consistent with the in vivo results, use of this combination of improvements in an AAV gene therapy vector increased in vitro biopotency 17-fold, relative to use of an AAV gene therapy vector that includes a polynucleotide having the same codon-alteration for an encoded wild-type Refacto Factor VIII using murine TTR promoter and enhancer sequences (compare vX5/NG5/CS120 to vSC04 in FIG. 14). As reported in Table 4 of WO 2017/083762 (the content of which is hereby incorporated herein by reference), the vCS04 vector provides more than 70-fold greater FVIII biopentency in vivo, relative to an equivalent gene therapy vector encoding for a Refacto Factor VIII polynucleotide using the wild-type coding sequence. Accordingly, it would be expected that the vX5/NG5/CS120 gene therapy vector would provide a 1000-fold to 1250-fold increase in FVIII biopotency, relative to use of the wild-type Refacto coding sequence.

In some implementations, one or more of these advantages are realized by engineering both the X5 mutations and the NG5 glycosylation peptide into a Factor VIII variant polypeptide that is encoded by a codon-altered Factor VIII polypeptide, using a human hTTR promoter and one or more liver-specific CRM8 elements upstream of the polynucleotide sequence encoding the Factor VIII variant polypeptide, and removing extraneous nucleotides positioned between various elements of the AAV gene therapy vector. Advantageously, using this combination of improvements provides improved biopotency of exogenously expressed Factor VIII, in vivo and in vitro. For instance, as described in Example 6, use of this combination of improvements in an AAV gene therapy vector increased in vivo biopotency 14-fold, relative to use of an AAV gene therapy vector that includes a polynucleotide having the same codon-alteration for an encoded wild-type Refacto Factor VIII using murine TTR promoter and enhancer sequences (compare vX5/NG5/CS12 to vSC04 in FIG. 14). Consistent with the in vivo results, use of this combination of improvements in an AAV gene therapy vector increased in vitro biopotency 24-fold, relative to use of an AAV gene therapy vector that includes a polynucleotide having the same codon-alteration for an encoded wild-type Refacto Factor VIII using murine TTR promoter and enhancer sequences (compare vX5/NG5/CS12 to vSC04 in FIG. 14). As reported in Table 4 of WO 2017/083762 (the content of which is hereby incorporated herein by reference), the vCS04 vector provides more than 70-fold greater FVIII biopentency in vivo, relative to an equivalent gene therapy vector encoding for a Refacto Factor VIII polynucleotide using the wild-type coding sequence. Accordingly, it would be expected that the vX5/NG5/CS120 gene therapy vector would provide a 1000-fold to 1750-fold increase in FVIII biopotency, relative to use of the wild-type Refacto coding sequence.

II. Definitions

As used herein, the following terms have the meanings ascribed to them unless specified otherwise.

As used herein, the terms "Factor VIII" and "FVIII" are used interchangeably, and refer to any protein with Factor VIII activity (e.g., active FVIII, often referred to as FVIIIa) or protein precursor (e.g., pro-protein or pre-pro-protein) of a protein with Factor IXa cofactor activity under particular conditions, e.g., as measured using the two-step chromogenic Factor X activation assay described in Chapter 2.7.4 of the European Pharmacopoeia 9.0. In an exemplary embodiment, a Factor VIII polypeptide refers to a polypeptide that has sequences with high sequence identity (e.g., at least 70%, 75%, 80%, 85%, 90%, 95%, 99%, or more) to the heavy and light chains of a wild type Factor VIII polypeptide. In some embodiments, the B-domain of a Factor VIII polypeptide is deleted, truncated, or replaced with a linker polypeptide to reduce the size of the polynucleotide encoding the Factor VIII polypeptide.

Non-limiting examples of wild type Factor VIII polypeptides include human pre-pro-Factor VIII (e.g., GenBank accession nos. AAA52485, CAA25619, AAA58466, AAA52484, AAA52420, AAV85964, BAF82636, BAG36452, CAI41660, CAI41666, CAI41672, CAI43241, CAO03404, EAW72645, AAH22513, AAH64380, AAH98389, AAI11968, AAI11970, or AAB61261), corresponding pro-Factor VIII, and natural variants thereof; porcine pre-pro-Factor VIII (e.g., UniProt accession nos. F1RZ36 or K7GSZ5), corresponding pro-Factor VIII, and natural variants thereof, mouse pre-pro-Factor VIII (e.g., GenBank accession nos. AAA37385, CAM15581, CAM26492, or EDL29229), corresponding pro-Factor VIII, and natural variants thereof; rat pre-pro-Factor VIII (e.g., GenBank accession no. AAQ21580), corresponding pro-Factor VIII, and natural variants thereof; rat pre-pro-Factor VIII; and other mammalian Factor VIII homologues (e.g., monkey, ape, hamster, guinea pig, etc.).

As used herein, a Factor VIII polypeptide includes natural variants and artificial constructs with Factor IX cofactor activity. As used in the present disclosure, Factor VIII encompasses any natural variants, alternative sequences, isoforms, or mutant proteins that retain some basal Factor IX cofactor activity (e.g., at least 5%, 10%, 25%, 50%, 75%, or more of the corresponding wild type activity).

Specifically included within the definition of "Factor VIII" are Factor VIII variants, sometimes also referred to as "variant FVIII". Variant FVIII proteins have at least one amino acid modification as compared to human wild type FVIII. Examples of Factor VIII amino acid variations (relative to FVIII-FL-AA (SEQ ID NO: 19)) found in the human population include, without limitation, S19R, R22T, Y24C, Y25C, L26P/R, E30V, W33G, Y35C/H, G41C, R48C/K, K67E/N, L69P, E72K, D75E/V/Y, P83R, G89D/V, G92A/V, A97P, E98K, V99D, D101G/H/V, V104D, K108T, M110V, A111T/V, H113R/Y, L117F/R, G121S, E129V, G130R, E132D, Y133C, D135G/Y, T137A/I, S138R, E141K, D145H, V147D, Y155H, V159A, N163K, G164D/V, P165S, C172W, S176P, S179P, V181E/M, K185T, D186G/N/Y, S189L, L191F, G193R, L195P, C198G, S202N/R, F214V, L217H, A219D/T, V220G, D222V, E223K, G224W, T252I, V253F, N254I, G255V, L261P, P262L, G263S, G266F, C267Y, W274C, H275L, G278R, G280D, E284K, V285G, E291G/K, T294I, F295L, V297A, N299I, R301C/H/L, A303E/P, I307S, S308L, F312S, T314A/I, A315V, G323E, L326P, L327P/V, C329F, I331V, M339T, E340K, V345A/L, C348R/S/Y, Y365C, R391C/H/P, S392L/P, A394S, W401G, I405F/S, E409G, W412G/R, K427I, L431F/S, R437P/W, I438F, G439D/S/V, Y442C, K444R, Y450D/N, T454I, F455C, G466E, P470L/R/T, G474E/R/V, E475K, G477V, D478N, T479R, F484C, A488G, R490G, Y492C/H, Y492H, I494T, P496R, G498R, R503H, G513S/V, I522Y, K529E, W532G, P540T, T541S, D544N, R546W, R550C/G/H, S553P, S554C/G, V556D, R560T, D561G/H/Y, I567T, P569R, S577F, V578A, D579A/H, N583S, Q584H/K/R, I585R/T, M586V, D588G/Y, L594Q, S596P, N601D/K, R602G, S603I/R, W604C, Y605H/S, N609I, R612C, N631K/S, M633I, S635N, N637D/I/S, Y639C, L644V, L650F, V653A/M, L659P, A663V, Q664P, F677L, M681I, V682F, Y683C/N, T686R, F698L, M699T/V, M701I, G705V, G710W, N713I, R717L/W, G720D/S, M721I/L, A723T, L725Q, V727F, E739K, Y742C, R795G, P947R, V1012L, E1057K, H1066Y, D1260E, K1289Q, Q1336K, N1460K, L1481P, A1610S, I1698T, Y1699C/F, E1701K, Q1705H, R1708C/H, T1714S, R1715G, A1720V, E1723K, D1727V, Y1728C, R1740G, K1751Q, F1762L, R1768H, G1769R, L1771P, L1775F/V, L1777P, G1779E/R, P1780L, I1782R, D1788H, M1791T, A1798P, S1799H, R1800C/G/H, P1801A, Y1802C, S1803Y, F1804S, L1808F, M1842I, P1844S, T1845P, E1848G, A1853T/V, S1858C, K1864E, D1865N/Y, H1867P/R, G1869D/V, G1872E, P1873R, L1875P, V1876L, C1877R/Y, L1882P, R1888I, E1894G, I1901F, E1904D/K, S1907C/R, W1908L, Y1909C, A1939T/V, N1941D/S, G1942A, M1945V, L1951F, R1960L/Q, L1963P, S1965I, M1966I/V, G1967D, S1968R, N1971T, H1973L, G1979V, H1980P/Y, F1982I, R1985Q, L1994P, Y1998C, G2000A, T2004R, M2007I, G2013R, W2015C, R2016P/W, E2018G, G2022D, G2028R, S2030N, V2035A, Y2036C, N2038S, 2040Y, G2045E/V, I2051S, I2056N, A2058P, W2065R, P2067L, A2070V, 52082N, S2088F, D2093G/Y, H2101D, T2105N, Q2106E/P/R, G2107S, R2109C, I2117F/S, Q2119R, F2120C/L, Y2124C, R2135P, S2138Y, T2141N, M2143V, F2145C, N2148S, N2157D, P2162L, R2169C/H, P2172L/Q/R, T2173A/I, H2174D, R2178C/H/L, R2182C/H/P, M2183R/V, L2185S/W, 52192I, C2193G, P2196R, G2198V, E2200D, I2204T, I2209N, A2211P, A2220P, P2224L, R2228G/L/P/Q, L2229F, V2242M, W2248C/S, V2251A/E, M2257V, T2264A, Q2265R, F2279C/I, I2281T, D2286G, W2290L, G2304V, D2307A, P2319L/S, R2323C/G/H/L, R2326G/L/P/Q, Q2330P, W2332R, I2336F, R2339T, G2344C/D/S, and C2345S/Y. Factor VIII proteins also include polypeptides containing post-translational modifications.

Generally, polynucleotides encoding Factor VIII encode for an inactive single-chain polypeptide (e.g., a pre-pro-protein) that undergoes post-translational processing to form an active Factor VIII protein (e.g., FVIIIa). For example, referring to FIG. 15, the wild type human Factor VIII pre-pro-protein is first cleaved to release the encoded signal peptide (not shown), forming a first single-chain pro-protein (shown as "human wild-type FVIII). The pro-protein is then cleaved between the B and A3 domains to form a first polypeptide that includes the Factor VIII heavy chain (e.g., the A1 and A2 domains) and B-domain, and a second polypeptide that includes the Factor VIII light chain (e.g., including the A3, C1, and C3 domains). The first polypeptide is further cleaved to remove the B-domain, and also to separate the A1 and A2 domains, which remain associated with the Factor VIII light chain in the mature Factor VIIIa protein. For review of the Factor VIII maturation process, see Graw et al., Nat Rev Genet., 6(6):488-501 (2005), the content of which is incorporated herein by reference in its entirety for all purposes.

As used herein, the terms "Factor VIII heavy chain," or simply "heavy chain," refers to the aggregate of the A1 and A2 domains of a Factor VIII polypeptide. In an exemplary embodiment, amino acids 20-759 of hFVIII-FL-AA (SEQ ID NO:39) constitute a Factor VIII heavy chain.

As used herein, the term "Factor VIII light chain," or simply "light chain," refers to the aggregate of the A3, C1, and C2 domains of a Factor VIII polypeptide. In an exemplary embodiment, amino acids 1668-2351 of hFVIII-FL-AA (SEQ ID NO:39) constitute a Factor VIII light chain. In some embodiments, a Factor VIII light chain excludes the acidic a3 peptide, which is released during maturation in vivo.

Generally, Factor VIII heavy and light chains are expressed as a single polypeptide chain, e.g., along with an optional B-domain or B-domain substituted linker. However, in some embodiments, a Factor VIII heavy chain and Factor VIII light chain are expressed as separate polypeptide chains (e.g., co-expressed), and reconstituted to form a Factor VIII protein (e.g., in vivo or in vitro).

As used herein, the terms "B-domain substituted linker" and "Factor VIII linker" are used interchangeably, and refer to truncated versions of a wild type Factor VIII B-domain (e.g., amino acids 760-1667 of hFVIII-FL-AA (SEQ ID NO:39)) or peptides engineered to replace the B-domain of a Factor VIII polypeptide. As used herein, a Factor VIII linker is positioned between the C-terminus of a Factor VIII heavy chain and the N-terminus of a Factor VIII light chain in a Factor VIII variant polypeptide in accordance with some embodiments. Non-limiting examples of B-domain substituted linkers are disclosed in U.S. Pat. Nos. 4,868,112, 5,112,950, 5,171,844, 5,543,502, 5,595,886, 5,610,278, 5,789,203, 5,972,885, 6,048,720, 6,060,447, 6,114,148, 6,228,620, 6,316,226, 6,346,513, 6,458,563, 6,924,365, 7,041,635, and 7,943,374; U.S. Patent Application Publication Nos. 2013/024960, 2015/0071883, and 2015/0158930; and PCT Publication Nos. WO 2014/064277 and WO 2014/127215, the disclosures of which are hereby incorporated by reference, in their entireties, for all purposes.

Unless otherwise specified herein, the numbering of Factor VIII amino acids refers to the corresponding amino acid in the full-length, wild-type human Factor VIII sequence (hFVIII-FL-AA), presented as SEQ ID NO:39 in FIG. 16. As such, when referring to an amino acid substitution in a Factor VIII variant protein disclosed herein, the recited amino acid number refers to the analogous (e.g., structurally or functionally equivalent) and/or homologous (e.g., evolutionarily conserved in the primary amino acid sequence) amino acid in the full-length, wild-type Factor VIII sequence. For example, a T2105N amino acid substitution refers to a T to N substitution at position 2105 of the full-length, wild-type human Factor VIII sequence (hFVIII-FL-AA; SEQ ID NO:39), a T to N substitution at position 1218 of the Factor VIII variant protein encoded by CS12 (CS12-FL-AA; SEQ ID NO: 2).

As described herein, the Factor VIII amino acid numbering system is dependent on whether the Factor VIII signal peptide (e.g., amino acids 1-19 of the full-length, wild-type human Factor VIII sequence) is included. Where the signal peptide is included, the numbering is referred to as "signal peptide inclusive" or "SPI". Where the signal peptide is not included, the numbering is referred to as "signal peptide exclusive" or "SPE." For example, F328S is SPI numbering for the same amino acid as F309S, in SPE numbering. Unless otherwise indicated, all amino acid numbering refers to the corresponding amino acid in the full-length, wild-type human Factor VIII sequence (hFVIII-FL-AA), presented as SEQ ID NO:39 in FIG. 16.

As described herein, the codon-altered polynucleotides provide increased expression of transgenic Factor VIII in vivo (e.g., when administered as part of a gene therapy vector), as compared to the level of Factor VIII expression provided by a natively-coded Factor VIII construct (e.g., a polynucleotide encoding the same Factor VIII construct using the wild-type human codons). As used herein, the term "increased expression" refers to an increased level of transgenic Factor VIII activity in the blood of an animal administered the codon-altered polynucleotide encoding Factor VIII, as compared to the level of transgenic Factor VIII activity in the blood of an animal administered a natively-coded Factor VIII construct. The activity levels can be measured using any Factor VIII activity known in the art, e.g., the two-step chromogenic Factor X activation assay described in Chapter 2.7.4 of the European Pharmacopoeia 9.0. An exemplary assay for determining Factor VIII activity is the Technochrome FVIII assay (Technoclone, Vienna, Austria).

In some embodiments, increased bioavailability refers to at least 25% greater transgenic Factor VIII polypeptide in the blood of an animal administered the codon-altered Factor VIII polynucleotide, as compared to the level of transgenic Factor VIII polypeptide in the blood of an animal administered a natively coded Factor VIII polynucleotide. In some embodiments, increased bioavailability refers to at least 25% greater transgenic Factor VIII polypeptide in the blood of an animal administered an improved gene therapy vector that includes a codon-altered Factor VIII polynucleotide, as compared to the level of a transgenic Factor VIII polypeptide in the blood of an animal administered a different gene therapy vector that includes the same or a different codon-altered Factor VIII polynucleotide. In some embodiments, increased expression refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, at least 20-fold greater, at least 25-fold greater, at least 30-fold greater, at least 40-fold greater, at least 50-fold greater, at least 60-fold greater, at least 70-fold greater, at least 80-fold greater, at least 90-fold greater, at least 100-fold greater, at least 125-fold greater, at least 150-fold greater, at least 175-fold greater, at least 200-fold greater, at least 225-fold greater, or at least 250-fold greater transgenic Factor VIII activity in the blood of an animal administered the codon-altered Factor VIII polynucleotide.

By "Factor VIII activity" herein is meant the ability to promote cleavage of a Factor X polypeptide by Factor IXa, e.g., Factor IXa co-factor activity, via hydrolysis of the Arg194-Ile195 peptide bond in wild-type Factor IX, thus activating Factor X to Factor Xa. The activity levels can be measured using any Factor VIII activity known in the art; suitable assays are outlined herein. An exemplary assay for determining Factor VIII activity is the two-step chromogenic Factor X activation assay described in Chapter 2.7.4 of the European Pharmacopoeia 9.0.

As used herein, the term "biopotency" refers to the amount of Factor VIII activity in the blood a subject, in vivo, or in a cell culture supernatant, in vitro. In some embodiments, biopotency will refer to an amount of activity per unit volume, such as units of Factor XIa co-factor activity per mL of blood, in vivo, or per mL cell culture supernatant, in vitro. In some embodiments, biopotency will be expressed as a fold increase with respect to a first level, e.g., a natively coded Factor VIII protein or a codon-optimized native Factor VIII (e.g., a 'wild-type' Refecto FVIII protein). In some embodiments, as used herein, the biopotency of exogenously expressed Factor VIII refers to the amount of Factor VIII activity provided by a recombinant Factor VIII protein expressed from a gene therapy vector. That is, the amount of Factor VIII activity in the blood or cell culture supernatant after accounting for any baseline amount of native Factor VIII activity. Thus, increases in biopotency can be achieved by either, or both, increasing the expression level of an exogenous Factor VIII protein and/or increasing the specific activity of an exogenous Factor VIII protein, e.g., by including amino acid substitutions (such as the X5 mutation) that confer greater specific activity.

In some embodiments, the therapeutic potential of a Factor VIII polynucleotide composition is evaluated by the increase in Factor VIII activity in the blood of an animal administered a Factor VIII polynucleotide, e.g., instead of, or in addition to, increased Factor VIII expression and/or bioavailability. In some embodiments, as used herein, increased Factor VIII activity refers to a greater increase in Factor VIII activity in the blood of an animal administered a codon-altered Factor VIII polynucleotide, relative to a baseline Factor VIII activity in the blood of the animal prior to administration of the codon-altered Factor VIII polynucleotide, as compared to the increase in Factor VIII activity in the blood of an animal administered a natively-coded Factor VIII polynucleotide, relative to a baseline Factor VIII activity in the blood of the animal prior to administration of the natively-coded Factor VIII polynucleotide. In some embodiments, increased Factor VIII activity refers to at least a 25% greater increase in Factor VIII activity in the blood of an animal administered the codon-altered Factor VIII polynucleotide, relative to a baseline level of Factor VIII activity in the blood of the animal prior to administration of the codon-altered Factor VIII polynucleotide, as compared to the increase in the level Factor VIII activity in the blood of an animal administered a natively-coded Factor VIII polynucleotide, relative to the baseline level of Factor VIII activity in the animal prior to administration of the natively-coded Factor VIII polynucleotide. In some embodiments, increased Factor VIII activity refers to at least a 25% greater increase in Factor VIII activity in the blood of an animal administered an improved gene therapy vector that includes a codon-altered Factor VIII polynucleotide, relative to a baseline level of Factor VIII activity in the blood of the animal prior to administration of the improved gene therapy vector, as compared to the increase in the level of Factor VIII activity in the blood of an animal administered a different gene therapy vector that includes the same or a different codon-altered Factor VIII polynucleotide, relative to the, relative to the baseline level of Factor VIII activity in the animal prior to administration of the different gene therapy vector. In some embodiments, increased Factor VIII activity refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, at least 20-fold greater, at least 25-fold greater, at least 30-fold greater, at least 40-fold greater, at least 50-fold greater, at least 60-fold greater, at least 70-fold greater, at least 80-fold greater, at least 90-fold greater, at least 100-fold greater, at least 125-fold greater, at least 150-fold greater, at least 175-fold greater, at least 200-fold greater, at least 225-fold greater, or at least 250-fold greater increase in Factor VIII activity in the blood of an animal administered the codon-altered Factor VIII polynucleotide, relative to a baseline level of Factor VIII activity in the blood of the animal prior to administration of the codon-altered Factor VIII polynucleotide, as compared to the increase in the level Factor VIII activity in the blood of an animal administered a natively-coded Factor VIII polynucleotide, or a different gene therapy vector that includes the same or a different codon-altered Factor VIII polynucleotide, relative to the baseline level of Factor VIII activity in the animal prior to administration of the natively-coded Factor VIII polynucleotide or different gene therapy vector that includes the same or a different codon-altered Factor VIII polynucleotide. Activity is measured using the two-step chromogenic Factor X activation assay described in Chapter 2.7.4 of the European Pharmacopoeia 9.0, as described herein.

As described herein, the codon-altered polynucleotides provide increased vector production, as compared to the level of vector production provided by a natively-coded Factor VIII construct (e.g., a polynucleotide encoding the same Factor VIII construct using the wild-type human codons). As used herein, the term "increased virus production" refers to an increased vector yield in cell culture (e.g., titer per liter culture) inoculated with the codon-altered polynucleotide encoding Factor VIII, as compared to the vector yield in cell culture inoculated with a natively-coded Factor VIII construct. The vector yields can be measured using any vector titer assay known in the art. An exemplary assay for determining vector yield (e.g., of an AAV vector) is qPCR targeting the AAV2 inverted terminal repeats (Aurnhammer, Human Gene Therapy Methods: Part B 23:18-28 (2012)).

In some embodiments, increased virus production refers to at least 25% greater codon-altered vector yield, as compared to the yield of a natively-coded Factor VIII construct in the same type of culture. In some embodiments, increased virus production refers to at least 25% greater yield of an improved vector that includes a codon-altered Factor VIII polynucleotide, as compared to the yield of a different vector that includes the same or a different codon-altered Factor VIII polynucleotide. In some embodiments, increased vector production refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, or at least 20-fold greater codon-altered vector yield.

As used herein, the term "hemophilia" refers to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Conventional treatments for hemophilia include both prophylactic and on-demand administration of clotting factors, such as FVIII, FIX, including Bebulin®-VH, and FXI, as well as FEIBA-VH, desmopressin, and plasma infusions.

As used herein, the term "FVIII gene therapy" includes any therapeutic approach of providing a nucleic acid encoding Factor VIII to a patient to relieve, diminish, or prevent the reoccurrence of one or more symptoms (e.g., clinical factors) associated with hemophilia. The term encompasses administering any compound, drug, procedure, or regimen comprising a nucleic acid encoding a Factor VIII molecule, including any modified form of Factor VIII (e.g., Factor VIII variant), for maintaining or improving the health of an individual with hemophilia. One skilled in the art will appreciate that either the course of FVIII therapy or the dose of a FVIII therapeutic agent can be changed, e.g., based upon the results obtained in accordance with the present disclosure.

As used herein, the term "Factor VIII gene therapy," or "FVIII gene therapy," includes any therapeutic approach of providing a nucleic acid encoding a Factor VIII polypeptide to a patient to relieve, diminish, or prevent the reoccurrence of one or more symptoms (e.g., clinical factors) associated with a Factor VIII deficiency (e.g., hemophilia A). The term encompasses administering any compound, drug, procedure, or regimen comprising a nucleic acid encoding a Factor VIII molecule, including any modified form of Factor VIII (e.g., a Factor VIII variant having the X5 mutations, a B-domain deletion, and/or a glycosylation peptide inserted into a B-domain linker polypeptide), for maintaining or improving the health of an individual with a Factor VIII deficiency (e.g., hemophilia A). One skilled in the art will appreciate that either the course of FVIII gene therapy or the dose of a FVIII gene therapy therapeutic agent can be changed, e.g., based upon the results obtained in accordance with the present disclosure.

As used herein, the term "bypass therapy" includes any therapeutic approach of providing non-Factor VIII hemostatic agents, compounds or coagulation factors to a patient to relieve, diminish, or prevent the reoccurrence of one or more symptoms (e.g., clinical factors) associated with hemophilia. Non-Factor VIII compounds and coagulation factors include, but are not limited to, Factor VIII Inhibitor Bypass Activity (FEIBA), recombinant activated factor VII (FVIIa), prothrombin complex concentrates, and activated prothrombin complex concentrates. These non-Factor VIII compounds and coagulation factors may be recombinant or plasma-derived. One skilled in the art will appreciate that either the course of bypass therapy or the dose of bypass therapy can be changed, e.g., based upon the results obtained in accordance with the present disclosure.

As used herein, a "combination therapy" including administration of a nucleic acid encoding a Factor VIII molecule and a conventional hemophilia A therapeutic agent includes any therapeutic approach of providing both a nucleic acid encoding a Factor VIII molecule and a Factor VIII molecule and/or non-Factor VIII hemostatic agent (e.g., bypass therapeutic agent) to a patient to relieve, diminish, or prevent the reoccurrence of one or more symptoms (e.g., clinical factors) associated with hemophilia. The term encompasses administering any compound, drug, procedure, or regimen including a nucleic acid encoding a Factor VIII molecule, including any modified form of factor VIII, which is useful for maintaining or improving the health of an individual with hemophilia and includes any of the therapeutic agents described herein.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia.

In some embodiments, a therapeutically effective treatment results in a decrease in the frequency and/or severity of bleeding incidents in a subject.

In some embodiments, a therapeutically effective treatment results in increased Factor VIII activity in the blood stream of a patient, as compared to the activity prior to the treatment.

As used herein, the term "gene" refers to the segment of a DNA molecule that codes for a polypeptide chain (e.g., the coding region). In some embodiments, a gene is positioned by regions immediately preceding, following, and/or intervening the coding region that are involved in producing the polypeptide chain (e.g., regulatory elements such as a promoter, enhancer, polyadenylation sequence, 5' untranslated region, 3' untranslated region, or intron).

As used herein, the term "regulatory elements" refers to nucleotide sequences, such as promoters, enhancers, terminators, polyadenylation sequences, introns, etc, that provide for the expression of a coding sequence in a cell.

As used herein, the term "promoter element" refers to a nucleotide sequence that assists with controlling expression of a coding sequence. Generally, promoter elements are located 5' of the translation start site of a gene. However, in certain embodiments, a promoter element may be located within an intron sequence, or 3' of the coding sequence. In some embodiments, a promoter useful for a gene therapy vector is derived from the native gene of the target protein (e.g., a Factor VIII promoter). In some embodiments, a promoter useful for a gene therapy vector is specific for expression in a particular cell or tissue of the target organism (e.g., a liver-specific promoter). In yet other embodiments, one of a plurality of well characterized promoter elements is used in a gene therapy vector described herein. Non-limiting examples of well-characterized promoter elements include the CMV early promoter, the j-actin promoter, and the methyl CpG binding protein 2 (MeCP2) promoter. In some embodiments, the promoter is a constitutive promoter, which drives substantially constant expression of the target protein. In other embodiments, the promoter is an inducible promoter, which drives expression of the target protein in response to a particular stimulus (e.g., exposure to a particular treatment or agent). For a review of designing promoters for AAV-mediated gene therapy, see Gray et al. (Human Gene Therapy 22:1143-53 (2011)), the contents of which are expressly incorporated by reference in their entirety for all purposes.

As used herein, a "CRM8" element refers to cis-acting regulatory module derived from the SERPINA1 gene (NCBI accession number NM_000295.4) that enhances expression of an operatively linked gene, e.g., a sequence encoding a Factor VIII polypeptide, in a liver-specific fashion having high sequence identity to SEQ ID NO:5. In some embodiments, the CRM8 element is identical to SEQ ID NO:5. As used herein, a CRM8 element refers to a single copy of the regulatory element which, in some embodiments, is included in one or more copies within a Factor VIII polynucleotide, e.g., 1, 2, 3, or more copies. For further information on CRM elements, such as CRM8, see Chuah M K et al., Mol Ther., 22(9):1605-13 (2014), which is hereby incorporated by reference.

As used herein, the term "operably linked" refers to the relationship between a first reference nucleotide sequence (e.g., a gene) and a second nucleotide sequence (e.g., a regulatory control element) that allows the second nucleotide sequence to affect one or more properties associated with the first reference nucleotide sequence (e.g., a transcription rate). In the context of the present disclosure, a regulatory control element is operably linked to a Factor VIII transgene when the regulatory element is positioned within a gene therapy vector such that it exerts an affect (e.g., a promotive or tissue-selective affect) on transcription of the Factor VIII transgene.

As used herein, the term "vector" refers to any vehicle used to transfer a nucleic acid (e.g., encoding a Factor VIII gene therapy construct) into a host cell. In some embodiments, a vector includes a replicon, which functions to replicate the vehicle, along with the target nucleic acid. Non-limiting examples of vectors useful for gene therapy include plasmids, phages, cosmids, artificial chromosomes, and viruses, which function as autonomous units of replication in vivo. In some embodiments, a vector is a viral vehicle for introducing a target nucleic acid (e.g., a codon-altered polynucleotide encoding a Factor VIII variant). Many modified eukaryotic viruses useful for gene therapy are known in the art. For example, adeno-associated viruses (AAVs) are particularly well suited for use in human gene therapy because humans are a natural host for the virus, the native viruses are not known to contribute to any diseases, and the viruses illicit a mild immune response.

As used herein, the term "Factor VIII viral vector" refers to a recombinant virus comprising a Factor VIII polynucleotide, encoding a Factor VIII polypeptide, which is sufficient for expression of the Factor VIII polypeptide when introduced into a suitable animal host (e.g., a human). Specifically included within the definition of Factor VIII viral vector are recombinant viruses in which a codon-altered Factor VIII polynucleotide, which encodes a Factor VIII polypeptide, has been inserted into the genome of the virus. Also specifically included within the definition of Factor VIII viral vectors are recombinant viruses in which the native genome of the virus has been replaced with a Factor VIII polynucleotide, which encodes a Factor VIII polypeptide. Included within the definition of Factor VIII viral vectors are recombinant viruses comprising a Factor VIII polynucleotide, which encodes a variant of Factor VIII having the X5 mutations, a B-domain deletion, and/or a glycosylation peptide inserted into a B-domain linker polypeptide.

As used herein, the term "Factor VIII viral particle" refers to a viral particle encapsulating a Factor VIII polynucleotide, encoding a Factor VIII polypeptide, which is specific for expression of the Factor VIII polypeptide when introduced into a suitable animal host (e.g., a human). Specifically included within the definition of Factor VIII viral particles are recombinant viral particles encapsulating a genome in which a codon-altered Factor VIII polynucleotide, which encodes a Factor VIII polypeptide, has been inserted. Also specifically included within the definition of Factor VIII viral particles are recombinant viral particles encapsulating a Factor VIII polynucleotide, which encodes a Factor VIII polypeptide, which replaces the native genome of the virus. Included within the definition of Factor VIII viral particles are recombinant viral particles encapsulating a Factor VIII polynucleotide, which encodes a variant of Factor VIII having the X5 mutations, a B-domain deletion, and/or a glycosylation peptide inserted into a B-domain linker polypeptide.

By "AAV" or "adeno-associated virus" herein is meant a Dependoparvovirus within the Parvoviridae genus of viruses. As used herein, AAV can refer to a virus derived from a naturally occurring "wild-type" AAV genome into which a Factor VIII polynucleotide has been inserted, a recombinant virus derived from a recombinant Factor VIII polynucleotide packaged into a capsid using capsid proteins encoded by a naturally occurring AAV cap gene, or a recombinant virus derived from a recombinant Factor VIII polynucleotide packaged into a capsid using capsid proteins encoded by a non-natural capsid cap gene. Included within the definition of AAV are AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), and AAV type 9 (AAV9) viruses encapsulating a Factor VIII polynucleotide and viruses formed by one or more variant AAV capsid proteins encapsulating a Factor VIII polynucleotide.

By "AAV8," "AAV-8," or "AAV serotype 8" herein is meant a virus formed by an AAV8 capsid viral protein that encapsulates a Factor VIII polynucleotide.

As used herein, the term "CpG" refers to a cytosine-guanine dinucleotide along a single strand of DNA, with the "p" representing the phosphate linkage between the two.

As used herein, the term "CpG island" refers to a region within a polynucleotide having a statistically elevated density of CpG dinucleotides. As used herein, a region of a polynucleotide (e.g., a polynucleotide encoding a codon-altered Factor VIII protein) is a CpG island if, over a 200-base pair window: (i) the region has GC content of greater than 50%, and (ii) the ratio of observed CpG dinucleotides per expected CpG dinucleotides is at least 0.6, as defined by the relationship:

$$\frac{N[CpG]*N[\text{length of window}]}{N[C]*N[G]} \geq 0.6.$$

For additional information on methods for identifying CpG islands, see Gardiner-Garden M. et al., J Mol Biol., 196(2): 261-82 (1987), the content of which is expressly incorporated herein by reference, in its entirety, for all purposes.

As used herein, the term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

The term "amino acid" refers to naturally occurring amino acids, including those encoded by the genetic code, as well as those amino acids that are later modified, e.g., hydroxyproline, y-carboxyglutamate, and O-phosphoserine. Naturally occurring amino acids can include, e.g., D- and L-amino acids. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution G151K refers to a variant polypeptide, in which the glycine at position 151 is replaced with lysine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution. Accordingly, each variation of a nucleic acid which encodes a same polypeptide is implicit in each described sequence with respect to the expression product, but not with respect to actual gene therapy constructs.

By "amino acid insertion" or "insertion" as used herein is meant the addition of an amino acid sequence at a particular position in a parent polypeptide sequence. For example, −233E or 233E designates an insertion of glutamic acid after position 233 and before position 234. Additionally, −233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233− or E233#, E233( ) or E233del designates a deletion of glutamic acid at position 233. Additionally, EDA233− or EDA233# designates a deletion of the sequence GluAspAla that begins at position 233. The terms "identical" or percent "identity," in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection.

As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc, all of which are incorporated by reference.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989), both incorporated by reference. Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403-410, (1990); Altschul et al., Nucleic Acids Res. 25:3389-3402 (1997); and Karlin et al., Proc. Natl. Acad. Sci. U.S.A. 90:5873-5787 (1993), both incorporated by reference. A particularly useful BLAST program is the WU-BLAST-2 program which was obtained from Altschul et al., Methods in Enzymology, 266:460-480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389-3402, incorporated by reference. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 1 (SEQ ID NO:1), it is understood that in one embodiment, the percentage of sequence identity will be determined based on the number of identical amino acids or nucleotides in relation to the total number of amino acids or nucleotides. Thus, for example, sequence identity of sequences shorter than that shown in FIG. 1 (SEQ ID NO:1), as discussed below, will be determined using the number of nucleotides in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

The term "allelic variants" refers to polymorphic forms of a gene at a particular genetic locus, as well as cDNAs derived from mRNA transcripts of the genes, and the polypeptides encoded by them. The term "preferred mammalian codon" refers a subset of codons from among the set of codons encoding an amino acid that are most frequently used in proteins expressed in mammalian cells as chosen from the following list: Gly (GGC, GGG); Glu (GAG); Asp (GAC); Val (GTG, GTC); Ala (GCC, GCT); Ser (AGC, TCC); Lys (AAG); Asn (AAC); Met (ATG); Ile (ATC); Thr (ACC); Trp (TGG); Cys (TGC); Tyr (TAT, TAC); Leu (CTG); Phe (TTC); Arg (CGC, AGG, AGA); Gln (CAG); His (CAC); and Pro (CCC).

As used herein, the term codon-altered refers to a polynucleotide sequence encoding a polypeptide (e.g., a Factor VIII variant protein), where at least one codon of the native polynucleotide encoding the polypeptide has been changed to improve a property of the polynucleotide sequence. In some embodiments, the improved property promotes increased transcription of mRNA coding for the polypeptide, increased stability of the mRNA (e.g., improved mRNA half-life), increased translation of the polypeptide, and/or increased packaging of the polynucleotide within the vector. Non-limiting examples of alterations that can be used to achieve the improved properties include changing the usage and/or distribution of codons for particular amino acids, adjusting global and/or local GC content, removing AT-rich sequences, removing repeated sequence elements, adjusting global and/or local CpG dinucleotide content, removing cryptic regulatory elements (e.g., TATA box and CCAAT box elements), removing of intron/exon splice sites, improving regulatory sequences (e.g., introduction of a Kozak consensus sequence), and removing sequence elements capable of forming secondary structure (e.g., stem-loops) in the transcribed mRNA.

As discussed herein, there are various nomenclatures to refer to components of the disclosure herein. "CS-number" (e.g. "CS12", "CS04", etc.) refer to codon altered polynucleotides encoding FVIII polypeptides and/or the encoded polypeptides, including variants. For example, CS12-FL refers to the Full Length codon altered CS12 polynucleotide sequence or amino acid sequence (sometimes referred to herein as "CS12-FL-AA" for the Amino Acid sequence and "CS12-FL-NA" for the Nucleic Acid sequence) encoded by the CS12 polynucleotide sequence. Similarly, "CS12-LC" refers to either the codon altered nucleic acid sequence ("CS12-LC-NA") encoding the light chain of a FVIII polypeptide or the amino acid sequence (also sometimes referred to herein as "CS12-LC-AA") of the FVIII light chain encoded by the CS12 polynucleotide sequence. Likewise, CS12-HC, CS12-HC-AA and CS12-HC-NA are the same for the FVIII heavy chain. As will be appreciated by those in the art, for constructs such as CS04, that are only codon-altered (e.g. they do not contain additional amino acid substitutions as compared to Refacto), the amino acid sequences will be identical, as the amino acid sequences are not altered by the codon optimization. Thus, sequence constructs of the disclosure include, but are not limited to, CS12-FL-NA, CS12-FL-AA, CS12-LC-NA, CS12-LC-AA, CS12-HC-AA, and CS12-HC-NA.

This nomenclature also applies to glycosylation peptides as shown in FIG. 8, such that "NG1-AA" refers to the amino acid sequence and NG1-NA refers to the nucleic acid sequence.

The disclosure also includes additional new Factor VIII variants, as described below, with the appropriate nomenclature.

As used herein, the term "liver-specific expression" refers to the preferential or predominant in vivo expression of a particular gene (e.g., a codon-altered, transgenic Factor VIII gene) in hepatic tissue, as compared to in other tissues. In some embodiments, liver-specific expression means that at least 50% of all expression of the particular gene occurs within hepatic tissues of a subject. In other embodiments, liver-specific expression means that at least 55%, 60%, 65%, 70%, 75%, 80%, 85%, 90%, 95%, 99%, or 100% of all expression of the particular gene occurs within hepatic tissues of a subject. Accordingly, a liver-specific regulatory element is a regulatory element that drives liver-specific expression of a gene in hepatic tissue.

As used herein, the terms "less than" X and "less than" X % refer to a range of from 0 to X, exclusive of the value X, e.g., from 0% to X %, exclusive of X %. As used herein, the terms are used interchangeably with a range starting at 0 or 0% through, but not including, X or X %.

As used herein, the terms "no more than" X or "no more than" X % refer to a range of from 0 to X, inclusive of the value X, e.g., from 0% to X %, inclusive of X %. As used herein, the terms are used interchangeably with a range starting at 0 or 0% through, and including, X or X %.

As used herein, the terms "greater than" X or "greater than" X % refer to a range of from X to an upper limit, exclusive of the value X, e.g., from X % to 100%, exclusive of X %. As used herein, the terms are used interchangeably with a range starting at, but not including, X or X % through an upper limit which is 100% in the context of a percentage.

As used herein, the terms "at least" X or "at least" X % refer to a range of from X to an upper limit, inclusive of the value X, e.g., from X % to 100%, inclusive of X %. As used herein, the terms are used interchangeably with a range starting at, and including, X or X % through an upper limit which is 100% in the context of a percentage.

As used herein, the terms "between 'X' and 'Y'," "between 'X'% and 'Y'%," "from 'X' to 'Y'," and "from 'X'% to 'Y'%" refer to a range of from X to Y, inclusive of the values X and Y, e.g., from X % to Y %, inclusive of X % and Y %. As used herein, the terms are used interchangeably with a range starting at X or X % through, and including, Y or Y %.

III. Codon-Altered Factor VIII Polynucleotides

In some embodiments, the present disclosure provides codon-altered polynucleotides encoding Factor VIII variants. These codon-altered polynucleotides provide markedly improved Factor VIII biopotency (e.g., activity) when administered in an AAV-based gene therapy construct. The codon-altered polynucleotides also demonstrate improved AAV-virion packaging, as compared to conventionally codon-optimized constructs.

Wild-type Factor VIII is encoded with a 19 amino acid signal peptide (amino acids 1-19 of SEQ ID NO:39), which is cleaved from the encoded polypeptide prior to activation of Factor VIII. As appreciated by those in the art the Factor VIII signal peptide may be mutated, replaced by signal peptides from other genes or Factor VIII genes from other organisms, or completely removed, without affecting the sequence of the mature polypeptide left after the signal peptide is removed by cellular processing.

Accordingly, in some embodiments, a codon-altered polynucleotide (e.g., a nucleic acid composition) provided herein has a nucleotide sequence with high sequence identity to the portions of CS12-FL-NA (SEQ ID NO:1) encoding a Factor VIII heavy and light chains, and a short, 14 amino acid, B-domain substituted linker (e.g., the "SQ" linker containing a furin cleavage site to facilitate maturation of an active FVIIIa protein in vivo), that further includes one or more of the five "X5 mutations" (e.g., one, two, three, four, or all five of the I105V/A127S/G151K/M166T/L171P mutations (SPI numbering; (SPE numbering is I86V/A108S/G132K/M147T/L152P, respectively)), relative to the full-length human wild type Factor VIII sequence), and/or a short glycosylation peptide (e.g., NG5; SEQ ID NO:15) inserted into the B-domain substituted linker (e.g., an SQ linker).

Specifically, the X5 mutation set is based on the fact that substitution of porcine amino acids 82-176 for the corresponding human amino acids in a B-domain deleted gene therapy construct increased Factor VIII activity when expressed in HEK293 cells (W. Xiao, communication). Back-mutation of single porcine amino acids into the human BDD-FVIII construct identified five amino acids within the A1 domain that contribute to this phenomenon: I105V, A127S, G151K, M166T, and L171P (SPI). Introduction of the combination of these mutations into the human construct recapitulated the improved activity of the larger porcine substitution. (W. Xiao, communication). Accordingly, in some embodiments, the encoded Factor VIII polypeptides include one or more amino acid substitutions selected from I105V, A127S, G151K, M166T, and L171P, with the entire 5 amino acid set finding particular use in many embodiments.

CS12 Codon Altered Polynucleotides

In some embodiments, a nucleic acid composition provided herein includes a codon-altered Factor VIII polynucleotide that has a nucleotide sequence with high sequence identity to CS12-FL-NA (SEQ ID NO:1) and encodes a Factor VIII polypeptide with human Factor VIII heavy and light chains, and a short, 14 amino acid, B-domain substituted linker (the "SQ" linker) containing a furin cleavage site to facilitate maturation of an active FVIIIa protein in vivo, where the heavy chain of the Factor VIII polypeptide includes the five X5 mutations (I105V, A127S, G151K, M166T, and L171P (SPI), relative to the full-length human wild type Factor VIII sequence), and an NG5 glycosylation peptide (SEQ ID NO:15) inserted into the SQ linker.

In some embodiments, the Factor VIII polynucleotide has a nucleotide sequence has at least 95% identity to CS12-FL-NA (SEQ ID NO:1). In some embodiments, the nucleotide sequence has at least 96% identity to CS12-FL-NA (SEQ ID NO:1). In some embodiments, the nucleotide sequence has at least 97% identity to CS12-FL-NA (SEQ ID NO:1). In some embodiments, the nucleotide sequence has at least 98% identity to CS12-FL-NA (SEQ ID NO:1). In some embodiments, the nucleotide sequence has at least 99% identity to CS12-FL-NA (SEQ ID NO:1). In some embodiments, the nucleotide sequence has at least 99.5% identity to CS12-FL-NA (SEQ ID NO:1). In some embodiments, the nucleotide sequence has at least 99.9% identity to CS12-FL-NA (SEQ ID NO:1). In some embodiments, the nucleotide sequence is identical to CS12-FL-NA (SEQ ID NO:1).

In some embodiments, the Factor VIII variant encoded by the codon-altered polynucleotide has an amino acid sequence with high sequence identity to CS12-FL-AA (SEQ ID NO: 2), including the five X5 mutations (I105V/A127S/G151K/M166T/L171P (SPI), relative to the full-length human wild type Factor VIII sequence), and an NG5 glycosylation peptide (SEQ ID NO:15) inserted into the SQ linker.

In some embodiments, the amino acid sequence of the encoded Factor VIII variant has at least 97% identity to CS12-FL-AA (SEQ ID NO: 2), including the five X5 mutations (I105V/A127S/G151K/M166T/L171P (SPI), relative to the full-length human wild type Factor VIII sequence), and an NG5 glycosylation peptide (SEQ ID NO:15) inserted into the SQ linker.

In some embodiments, the amino acid sequence of the encoded Factor VIII variant has at least 98% identity to CS12-FL-AA (SEQ ID NO: 2), including the five X5 mutations (I105V/A127S/G151K/M166T/L171P (SPI), relative to the full-length human wild type Factor VIII sequence), and an NG5 glycosylation peptide (SEQ ID NO:15) inserted into the SQ linker.

In some embodiments, the amino acid sequence of the encoded Factor VIII variant has at least 99% identity to CS12-FL-AA (SEQ ID NO: 2), including the five X5 mutations (I105V/A127S/G151K/M166T/L171P (SPI), relative to the full-length human wild type Factor VIII sequence), and an NG5 glycosylation peptide (SEQ ID NO:15) inserted into the SQ linker.

In some embodiments, the amino acid sequence of the encoded Factor VIII variant has at least 99.5% identity to CS12-FL-AA (SEQ ID NO: 2), including the five X5 mutations (I105V/A127S/G151K/M166T/L171P (SPI), relative to the full-length human wild type Factor VIII sequence), and an NG5 glycosylation peptide (SEQ ID NO:15) inserted into the SQ linker.

In some embodiments, the amino acid sequence of the encoded Factor VIII variant has at least 99.9% identity to CS12-FL-AA (SEQ ID NO: 2), including the five X5 mutations (I105V/A127S/G151K/M166T/L171P (SPI), relative to the full-length human wild type Factor VIII sequence), and an NG5 glycosylation peptide (SEQ ID NO:15) inserted into the SQ linker.

In some embodiments, the amino acid sequence of the encoded Factor VIII variant is to CS12-FL-AA (SEQ ID NO: 2).

Factor VII B-Domain Substituted Linkers

As described above, the linkage between the FVIII heavy chain and the light chain (e.g., the B-domain in wild-type Factor VIII) is altered in the Factor VIII variants described herein. Removal of the B-domain from wild type Factor VIII constructs does not appear to affect the activity of the activated enzyme (e.g., FVIIIa), presumably because the B-domain is removed during activation. Due to size constraints of AAV packaging capacity, B-domain deleted, truncated, and or linker substituted variants should improve the efficacy of the FVIII gene therapy construct. The most conventionally used B-domain substituted linker is that of SQ FVIII, which retains only 14 amino acids of the B domain as linker sequence. Another variant of porcine VIII ("OBI-1," described in U.S. Pat. No. 6,458,563) is well expressed in CHO cells, and has a slightly longer linker of 24 amino acids. In some embodiments, the Factor VIII constructs encoded by the codon-altered polynucleotides described herein include an SQ-type B-domain linker sequence. In other embodiments, the Factor VIII constructs encoded by the codon-altered polynucleotides described herein include an OBI-1-type B-domain linker sequence.

Although the Factor VIII B-domain is dispensable for activity, the B-domain contains several residues that are post-translationally modified, e.g., by N- or O-linked glycosylation. In silico analysis (Prediction of N-glycosylation sites in human proteins, R. Gupta, E. Jung and S. Brunak, in preparation (2004)) of the wild-type Factor VIII B-domain predicts that at least four of these sites are glycosylated in vivo. It is thought that these modifications within the B-domain contribute to the post-translational regulation and/or half-life of Factor VIII in vivo. Thus, in some embodiments, the polypeptide linker of the encoded Factor VIII constructs described herein includes one or more glycosylation sequences, to allow for glycosylation in vivo. In some embodiments, the polypeptide linker includes at least one consensus glycosylation sequence (e.g., an N- or O-linked glycosylation consensus sequence). In some embodiments, the polypeptide linker includes at least two consensus glycosylation sequences. In some embodiments, the polypeptide linker includes at least three consensus glycosylation sequences. In some embodiments, the polypeptide linker includes at least four consensus glycosylation sequences. In some embodiments, the polypeptide linker includes at least five consensus glycosylation sequences. In some embodiments, the polypeptide linker includes at least 6, 7, 8, 9, 10, or more consensus glycosylation sequences.

In some embodiments, the polypeptide linker contains at least one N-linked glycosylation sequence N-X-S/T, where X is any amino acid other than P, S, or T. In some embodiments, the polypeptide linker contains at least two N-linked glycosylation sequences N-X-S/T, where X is any amino acid other than P, S, or T. In some embodiments, the polypeptide linker contains at least three N-linked glycosylation sequences N-X-S/T, where X is any amino acid other than P, S, or T. In some embodiments, the polypeptide linker contains at least four N-linked glycosylation sequences N-X-S/T, where X is any amino acid other than P, S, or T. In some embodiments, the polypeptide linker contains at least five N-linked glycosylation sequences N-X-S/T, where X is any amino acid other than P, S, or T. In some embodiments, the polypeptide linker contains at least 6, 7, 8, 9, 10, or more N-linked glycosylation sequences N-X-S/T, where X is any amino acid other than P, S, or T.

In some embodiments, the encoded Factor VIII polypeptides described herein include an SQ-type B-domain linker, including amino acids 760-762/1657-1667 of the wild-type human Factor VIII B-domain (FVIII-FL-AA; SEQ ID NO:39) (Sandberg et al. Thromb. Haemost. 85:93 (2001), the content of which is hereby incorporated herein by reference). In some embodiments, the SQ-type B-domain linker has one amino acid substitution relative to the corresponding wild-type sequence. In some embodiments, the SQ-type B-domain linker has two amino acid substitutions relative to the corresponding wild-type sequence.

In some embodiments, a glycosylation peptide is inserted into the SQ-type B-domain linker. In some embodiments, the glycosylation peptide is selected from those shown in FIG. 8 (SEQ ID NOS: 11, 13, 15, 17, 19, 21, 23, 25, 27, 29, 31, 33, and 35, respectively, in order of appearance). In some embodiments, the glycosylation peptide is encoded by a respective polynucleotide shown in FIG. 8 (SEQ ID NOS: 12, 14, 16, 18, 20, 22, 24, 26, 28, 30, 32, 34, and 36, respectively, in order of appearance. In a particular embodiment, the NG5 glycosylation peptide (SEQ ID NO:15) is inserted into the SQ-type B-domain linker of the Factor VIII polypeptides described herein. In a particular embodiment, the NG5 glycosylation peptide is encoded by a polynucleotide having a nucleic acid sequence of SEQ ID NO:16.

In some embodiments, the SQ-type B-domain linker containing the glycosylation peptide encoded by a respective polynucleotide shown in FIG. 17 (SEQ ID NOS: 40-53, respectively, in order of appearance. In a particular embodiment, the SQ-type B-domain linker containing the glycosylation peptide is encoded by a polynucleotide having a nucleic acid sequence of SEQ ID NO:43.

In some embodiments, the polypeptide linker (e.g., the SQ-type B-domain linker) includes a glycosylation peptide with high sequence identity to any one of SEQ ID NOS: 11, 13, 15, 17, 19, 21, 23, 25, 27, 29, 31, 33, and 35, respectively, in order of appearance, as shown in FIGS. 8A-8B. In some embodiments, the glycosylation peptide has no more than two amino acid substitutions relative to any one of SEQ ID NOS: 11, 13, 15, 17, 19, 21, 23, 25, 27, 29, 31, 33, and 35, respectively, in order of appearance, as shown in FIGS. 8A-8B. In some embodiments, the glycosylation peptide has no more than one amino acid substitution relative to any of SEQ ID NOS: 11, 13, 15, 17, 19, 21, 23, 25, 27, 29, 31, 33, and 35, respectively, in order of appearance, as shown in FIGS. 8A-8B. In some embodiments, the glycosylation peptide has an amino acid sequence selected from any of SEQ ID NOS: 11, 13, 15, 17, 19, 21, 23, 25, 27, 29, 31, 33, and 35, respectively, in order of appearance, as shown in FIGS. 8A-8B. In some embodiments, the glycosylation peptide is encoded by a polynucleotide sequence having high sequence identity to a corresponding nucleotide sequence selected from SEQ ID NOS: 12, 14, 16, 18, 20, 22, 24, 26, 28, 30, 32, 34, and 36, respectively, in order of appearance, as shown in FIGS. 8A-8B.

In some embodiments, the glycosylation peptide has no more than two amino acid substitutions relative to SEQ ID NO:15 and is encoded by a polynucleotide sequence having at least 90% identity to SEQ ID NO:16. In some embodiments, the glycosylation peptide has no more than two amino acid substitutions relative to SEQ ID NO:15 and is encoded by a polynucleotide sequence having at least 95% identity to SEQ ID NO:16. In some embodiments, the glycosylation peptide has no more than two amino acid substitutions relative to SEQ ID NO:15 and is encoded by a polynucleotide sequence having at least 98% identity to SEQ ID NO:16.

In some embodiments, the glycosylation peptide has no more than one amino acid substitution relative to SEQ ID NO:15 and is encoded by a polynucleotide sequence having at least 90% identity to SEQ ID NO:16. In some embodiments, the glycosylation peptide has no more than one amino acid substitution relative to SEQ ID NO:15 and is encoded by a polynucleotide sequence having at least 95% identity to SEQ ID NO:16. In some embodiments, the glycosylation peptide has no more than one amino acid substitution relative to SEQ ID NO:15 and is encoded by a polynucleotide sequence having at least 98% identity to SEQ ID NO:16.

In some embodiments, the glycosylation peptide has an amino acid sequence of SEQ ID NO:15 and is encoded by a polynucleotide sequence having at least 90% identity to SEQ ID NO: 16. In some embodiments, the glycosylation peptide has an amino acid sequence of SEQ ID NO:15 and is encoded by a polynucleotide sequence having at least 95% identity to SEQ ID NO:16. In some embodiments, the glycosylation peptide has an amino acid sequence of SEQ ID NO:15 and is encoded by a polynucleotide sequence having at least 98% identity to SEQ ID NO:16.

Cis-Regulatory Elements

In some embodiments, a nucleic acid composition encoding a Factor VIII variant, as provided herein, also includes one or more cis-acting regulatory elements, e.g. promoter and/or enhancer elements, that drives gene expression in vivo, which is operably linked to the polynucleotide encoding the Factor VIII variant. IN this context, “cis acting” means that the regulatory element are present on the same molecule of DNA as the gene they regulate. As will be appreciated by those in the art and discussed below, suitable regulatory elements for use in the invention include, but are not limited to, promoters, enhancer elements, polyadenylation signal elements, and/or inverted terminal repeat elements.

Promoters

The promoters of use in the invention are operably linked to the coding region, generally directly linked (e.g. no additional nucleotides are included between the promoter and the coding region) although in some embodiments, indirect linkages can be used, for example through the use of non-functional linkers, or in cases where additional regulatory elements that function “downstream” of the promoter but “upstream” of the coding region can be used. However, due to the size constraints of the vectors of the invention, this is generally not preferred.

Enhancer Elements

In some embodiments, one or more enhancer element is used in the Factor VIII variant construct. As is known in the art, enhancer elements generally drive expression in a tissue dependent fashion, e.g., predominantly in a specific tissue. In general, as described below, enhancer elements are generally positioned “upstream” of the promoter elements. Because Factor VIII is synthesized primarily in the liver, in some embodiments, the nucleic acid compositions described herein include a liver-specific regulatory element, which substantially limits expression of the encoded Factor VIII variant to hepatic cells.

Generally, liver-specific regulatory elements can be derived from any gene known to be exclusively expressed in the liver. WO 2009/130208 identifies several genes expressed in a liver-specific fashion, including, serpin peptidase inhibitor, clade A member 1, also known as α-antitrypsin (SERPINA1; GeneID 5265), apolipoprotein C-I (APOC1; GeneID 341), apolipoprotein C-IV (APOC4; GeneID 346), apolipoprotein H (APOH; GeneID 350); transthyretin (TTR; GeneID 7276), albumin (ALB; GeneID 213), aldolase B (ALDOB; GeneID 229), cytochrome P450, family 2, subfamily E, polypeptide 1 (CYP2E1; GeneID 1571), fibrinogen alpha chain (FGA; GeneID 2243), transferrin (TF; GeneID 7018), haptoglobin related protein (HPR; GeneID 3250). In some embodiments, the nucleic acid compositions described herein include a liver-specific regulatory element derived from the genomic loci of one or more of these proteins. Several examples of such elements are described in WO 2009/130208, the content of which is expressly incorporated herein by reference, in its entirety, for all purposes.

One example of a liver-specific regulatory element is from the transthyretin (TTR) gene, commonly referred to as “TTRe” or “TTREnh.” Hsieh J. L., et al., Cancer Sci., 100(3):537-45 (2009), the content of which is expressly incorporated herein by reference, in its entirety, for all purposes. In some embodiments, nucleic acid composition encoding a Factor VIII variant, as described herein, includes a human TTR promoter element. In one embodiment, the human TTR promoter has a nucleic acid sequence with high sequence identity to the hTTR promoter shown in FIG. 4 (SEQ ID NO:6). In some embodiments, the human TTR promoter has a nucleic acid sequence that is at least 90%, 95%, 96%, 97%, 98%, 99%, 99.5%, or 100% identical to SEQ ID NO:6.

Another example of a liver-specific regulatory element is from the SERPINA1 gene, as described in PCT Publication No. WO 2016/146757, the content of which is expressly incorporated herein by reference, in its entirety, for all purposes. An example of such an element is the CRM8 regulatory control element shown in FIG. 4 (SEQ ID NO:5). In some embodiments, a SERPINA1-derived regulatory control element has a nucleic acid sequence that is at least 90%, 95%, 96%, 97%, 98%, 99%, or 100% identical to CRM8 (SEQ ID NO:5).

Figure 11:
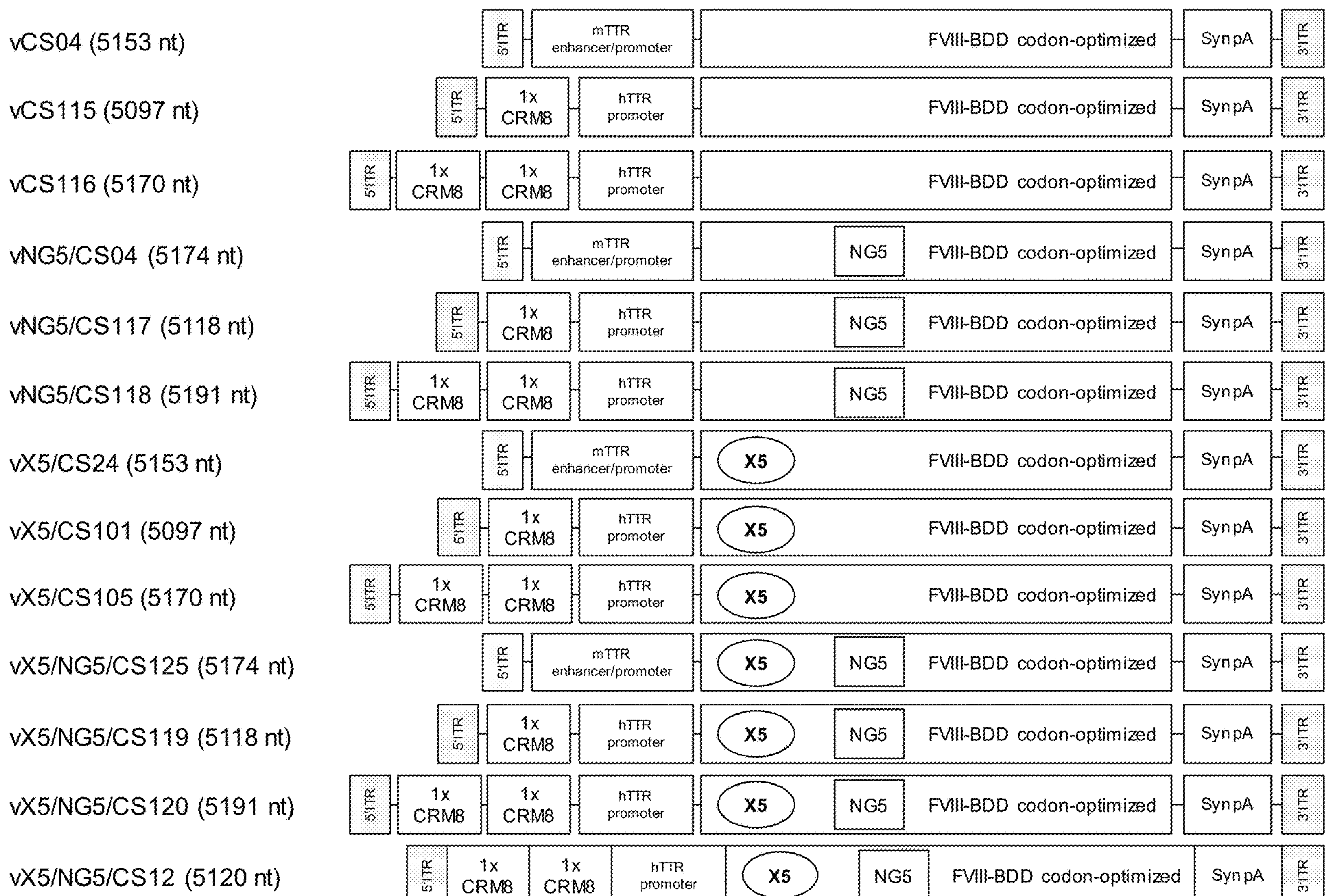
FIG. 11 illustrates exemplary Factor VIII gene therapy constructs encoding a Factor VIII variant in accordance with some implementations.

In some embodiments, a nucleic acid composition encoding a Factor VIII variant, as provided herein, includes one or more SERPINA1-derived regulatory control element, as exemplified by the constructs illustrated in FIG. 11. In one embodiment, a Factor VIII polynucleotide includes one SERPINA1-derived regulatory control element (e.g., CRM8). In another embodiment, a Factor VIII polynucleotide includes two SERPINA1-derived regulatory control elements (e.g., CRM8). In yet other embodiments, a Factor VIII polynucleotide includes 3, 4, 5, 6, or more SERPINA1-derived regulatory control elements (e.g., CRM8).

In one embodiment, a nucleic acid composition encoding a Factor VIII variant, as provided herein, includes one or more SERPINA1-derived regulatory control element (e.g., CRM8) and a human TTR promoter element, as exemplified in FIG. 11. In one embodiment, a nucleic acid composition encoding a Factor VIII variant, as provided herein, includes two CRM8 elements and a human TTR promoter element operably linked to the polynucleotide encoding the Factor VIII variant.

In some embodiments, a nucleic acid composition encoding a Factor VIII variant, as provided herein, includes one or more CRM8 element positioned upstream of a human TTR promoter. E.g., the one or more CRM8 element is positioned 5' of the TTR promoter in a double stranded construct, relative to the transcriptional orientation of the molecule. This means that in a (+) single-stranded construct (e.g., where the single strand encodes for the Factor VIII variant), the one or more CRM8 element is positioned 5' of the TTR promoter.

As reported in Example 6, because of the large size of the Factor VIII variant constructs described herein, a small reduction in the number of nucleotides in a Factor VIII polynucleotide that is part of an AAV gene therapy vector can significantly increase the Factor VIII biopotency of the vector. Accordingly, in some embodiments, the one or more CRM8 element is directly attached to the 5' end of the TTR promoter, e.g., there are no extraneous nucleotides positioned between the CRM8 element and the TTR promoter. Likewise, in some embodiments, the TTR promoter is directly attached to the 5' end of the coding sequence, or to a translational initiation sequence (e.g., a Kozak sequence), for the Factor VIII variant polypeptide, e.g., there are no extraneous nucleotides positioned between the TTR promoter and the Factor VIII variant gene.

Polyadenylation Signals

In some embodiments, the regulatory element for the constructs described herein (e.g. a nucleic acid composition encoding a Factor VIII variant) is a regulatory element that is a polyadenylation signal, e.g., as illustrated in the examples constructs in FIG. 11. The polyadenylation signal directs synthesis of a poly-A tail on the 3' end of the mRNA transcript generated from the Factor VIII polynucleotide.

Accordingly, the polyadenylation signal is positioned 3' to the Factor VIII variant coding sequence. Non-limiting examples of polyadenylation signals that can be used in the Factor IX gene therapy constructs described herein include synthetic polyadenylation signals, poly-adenylation signals derived from a Simian virus 40 (SV40) late gene, a bovine growth hormone (BGH) polyadenylation signal, and a minimal rabbit β-globin (mRBG) gene polyadenylation signal.

In some embodiments, a nucleic acid composition encoding a Factor VIII variant, as provided herein, includes a synthetic polyadenylation signal, as exemplified by the constructs illustrated in FIG. 11. In one embodiment, the synthetic polyadenylation signal has a nucleic acid sequence that is at least 90%, 95%, 97%, or 100% identical to the synthetic Poly-A signal shown in FIG. 4 (SEQ ID NO:8).

As reported in Example 6, because of the large size of the Factor VIII variant constructs described herein, a small reduction in the number of nucleotides in a Factor VIII polynucleotide that is part of an AAV gene therapy vector can significantly increase the Factor VIII biopotency of the vector. Accordingly, in some embodiments, the polyadenylation signal is directly attached to the 3' end of the coding sequence of the Factor VIII variant polypeptide, including one or more stop codons that are positioned at the end of the coding sequence. E.g., there are no extraneous nucleotides positioned between the Factor VIII variant gene and the polyadenylation sequence.

Inverted Terminal Repeats

In some embodiments, a nucleic acid composition encoding a Factor VIII variant, as provided herein, also includes adeno-associated virus (AAV) internal terminal repeats (ITRs) flanking the Factor VIII variant coding sequence and associated regulatory elements (e.g., promoters, enhancers, polyadenylation signals, etc.). The inverted terminal repeats each form a hairpin, which facilitates self-priming for primase-independent synthesis of the second DNA strand. The ITRs also help facilitate encapsulation within an AAV virion and integration of the AAV genome into the host cell genome.

In some embodiments, a nucleic acid composition encoding a Factor VIII variant, as provided herein, includes a 5' ITR having high sequence identity (e.g., at least 90%, 95%, 96%, 97%, 98%, 99%, or 100% identical) to the AAV2 5' ITR shown in FIG. 4 (SEQ ID NO:4). In some embodiments, a nucleic acid composition encoding a Factor VIII variant, as provided herein, includes a 3' ITR having high sequence identity (e.g., at least 90%, 95%, 96%, 97%, 98%, 99%, or 100% identical) to the AAV2 3' ITR shown in FIG. 4 (SEQ ID NO:9).

As reported in Example 6, because of the large size of the Factor VIII variant constructs described herein, a small reduction in the number of nucleotides in a Factor VIII polynucleotide that is part of an AAV gene therapy vector can significantly increase the Factor VIII biopotency of the vector. Accordingly, in some embodiments, the 5' ITR is directly attached to the 5' end of the liver-specific element (e.g., one or more CRM8 elements), such that no extraneous nucleotides are positioned between the 5' ITR sequence and the liver-specific element. Similarly, in some embodiments, the 3' ITR is directly attached to the 3' end of the polyadenylation signal, such that no extraneous nucleotides are positioned between the polyadenylation signal and the 3' ITR sequence.

IV. Factor VIII Expression Vectors

In some embodiments, the codon-altered polynucleotides described herein are integrated into expression vectors. Non-limiting examples of expression vectors include viral vectors (e.g., vectors suitable for gene therapy), plasmid vectors, bacteriophage vectors, cosmids, phagemids, artificial chromosomes, and the like. In general, there are two basic types of expression vectors of use in the invention: those that are used in cell culture to produce the Factor VIII polypeptides, and those that are used as gene therapy vectors to administer to patients such that endogeneous levels of Factor VIII (whether protein or activity) are increased.

Non-limiting examples of viral vectors include: retrovirus, e.g., Moloney murine leukemia virus (MMLV), Harvey murine sarcoma virus, murine mammary tumor virus, and Rous sarcoma virus; adenoviruses, adeno-associated viruses; SV40-type viruses; polyomaviruses; Epstein-Barr viruses; papilloma viruses; herpes viruses; vaccinia viruses; and polio viruses.

In many embodiments, the codon-optimized polynucleotides of the invention are used in gene therapy applications, such that the administration to a patient results in the production of Factor VIII as generally described herein. In general, gene therapy viral vectors are preferably replication deficient, such that the introduction of the gene therapy vector into a patient does not result in viral propagation.

Accordingly, in some embodiments, the codon-altered polynucleotides described herein are integrated into a gene therapy vector. In some embodiments, the gene therapy vector is a retrovirus, and particularly a replication-deficient retrovirus. In some embodiments, the codon-altered polynucleotides described herein are integrated into a retroviral expression vector. These systems have been described previously, and are generally well known in the art (Mann et al., *Cell,* 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., *Science,* 272(5259): 263-267, 1996; Zufferey et al., *Nat Biotechnol,* 15(9):871-875, 1997; Blomer et al., *J Virol.,* 71(9):6641-6649, 1997; U.S. Pat. Nos. 6,013,516 and 5,994,136). Protocols for the production of replication-deficient retroviruses are known in the art. For review, see Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

A wide variety of vectors can be used for the expression of a Factor VIII polypeptide from a codon-altered polypeptide in cell culture, including eukaryotic and prokaryotic expression vectors. In certain embodiments, a plasmid vector is contemplated for use in expressing a Factor VIII polypeptide in cell culture. In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will include the codon-altered polynucleotide encoding the Factor VIII polypeptide, operably linked to one or more control sequences, for example, a promoter.

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

Adeno-Associated Virus (AAV) Vectors

In one embodiment, a codon-altered polynucleotide, as described herein, is integrated into an adeno-associated virus (AAV)-based gene therapy vector. AAV systems have been described previously and are generally well known in the art (Kelleher and Vos, *Biotechniques,* 17(6):1110-17 (1994); Cotten et al., *Proc Natl Acad Sci USA,* 89(13):6094-98 (1992); Curiel, *Nat Immun,* 13(2-3):141-64 (1994); Muzyczka, *Curr Top Microbiol Immunol,* 158:97-129 (1992); and Asokan A, et al., Mol. Ther., 20(4):699-708 (2012), each incorporated herein by reference in their entireties for all purposes). Details concerning the generation and use of rAAV vectors are described, for example, in U.S. Pat. Nos. 5,139,941 and 4,797,368, each incorporated herein by reference in their entireties for all purposes.

Accordingly, in some embodiments, an AAV gene therapy vector is provided that includes a codon-altered polynucleotide (e.g., a nucleic acid composition), as described herein, that includes a nucleotide sequence with high sequence identity to the portions of CS12-FL-NA (SEQ ID NO:1) encoding a Factor VIII heavy and light chains, and a short, 14 amino acid, B-domain substituted linker (e.g., the "SQ" linker containing a furin cleavage site to facilitate maturation of an active FVIIIa protein in vivo), and that further includes one or more of the five X5 mutations (e.g., one, two, three, four, or all five of the I105V, A127S, G151K, M166T, L171P mutations (SPI), relative to the full-length human wild type Factor VIII sequence), and/or a short glycosylation peptide (e.g., NG5; SEQ ID NO:15) inserted into the B-domain substituted linker (e.g., an SQ linker).

In some embodiments, the AAV gene therapy vector includes a codon-altered Factor VIII polynucleotide that has a nucleotide sequence with high sequence identity to CS12-FL-NA (SEQ ID NO:1) and encodes a Factor VIII polypeptide with human Factor VIII heavy and light chains, and a short, 14 amino acid, B-domain substituted linker (the "SQ" linker) containing a furin cleavage site to facilitate maturation of an active FVIIIa protein in vivo, where the heavy chain of the Factor VIII polypeptide includes the five X5 mutations (I105V, A127S, G151K, M166T, and L171P (SPI), relative to the full-length human wild type Factor VIII sequence), and an NG5 glycosylation peptide (SEQ ID NO:15) inserted into the SQ linker. In some embodiments, the Factor VIII polynucleotide has a nucleotide sequence has at least 95%, 96%, 97%, 98%, 99%, 99.5%, 99.9%, or 100% identity to CS12-FL-NA (SEQ ID NO:1).

In some embodiments, the Factor VIII variant encoded by the codon-altered polynucleotide of the AAV gene therapy vector has an amino acid sequence with high sequence identity to CS12-FL-AA (SEQ ID NO: 2), including the five X5 mutations (I105V/A127S/G151K/M166T/L171P (SPI), relative to the full-length human wild type Factor VIII sequence), and an NG5 glycosylation peptide (SEQ ID NO:15) inserted into the SQ linker. In some embodiments, the amino acid sequence of the encoded Factor VIII variant has at least 97%, 98%, 99%, 99.5%, 99.9%, or 100% identity to CS12-FL-AA (SEQ ID NO: 2), including the five X5 mutations (I105V/A127S/G151K/M166T/L171P (SPI), relative to the full-length human wild type Factor VIII sequence), and an NG5 glycosylation peptide (SEQ ID NO:15) inserted into the SQ linker.

In some embodiments, the polynucleotide encoding the Factor VIII variant within the AAV gene therapy vector is operatively linked to a promoter element having a nucleic acid sequence with high sequence identity to the hTTR promoter shown in FIG. 4 (SEQ ID NO:6). In some embodiments, the promoter element has a nucleic acid sequence that is at least 90%, 95%, 96%, 97%, 98%, 99%, 99.5%, or 100% identical to SEQ ID NO:6.

In some embodiments, the polynucleotide encoding the Factor VIII variant within the AAV gene therapy vector is operatively linked to one or more liver-specific regulatory elements having a nucleic acid sequence with high sequence identity to the CRM8 element shown in FIG. 4 (SEQ ID NO:5). In some embodiments, the liver-specific regulatory elements have a nucleic acid sequence that is at least 90%, 95%, 96%, 97%, 98%, 99%, 99.5%, or 100% identical to SEQ ID NO:5. In some embodiments, as illustrated in FIG. 11, the polynucleotide includes one CRM8 element. In some embodiments, as illustrated in FIG. 11, the polynucleotide includes two CRM elements.

In some embodiments, the polynucleotide encoding the Factor VIII variant within the AAV gene therapy vector is operatively linked to one CRM8 element and a human TTR promoter element, as exemplified in FIG. 11. In some embodiments, the polynucleotide encoding the Factor VIII variant within the AAV gene therapy vector is operatively linked to two CRM8 element and a human TTR promoter element, as exemplified in FIG. 11. As described in Example 2, use of the hTTR promoter and either one or two liver-specific CRM8 elements increased in vivo exogenous Factor VIII biopotency in HepG2 cells by about 2-fold and 4-fold, respectively, as compared to use of mouse TTR promoter and enhancer sequences (compare vCS115 and vCS116 to vCS04 in FIG. 12).

As reported in Example 6, because of the large size of the Factor VIII variant constructs described herein, a small reduction in the number of nucleotides in a Factor VIII polynucleotide that is part of an AAV gene therapy vector can significantly increase the Factor VIII biopotency of the vector. Accordingly, in some embodiments, the one or more CRM8 element is directly attached to the 5' end of the TTR promoter, e.g., there are no extraneous nucleotides positioned between the CRM8 element and the TTR promoter. Likewise, in some embodiments, the TTR promoter is directly attached to the 5' end of the coding sequence, or to a translational initiation sequence (e.g., a Kozak sequence), for the Factor VIII variant polypeptide, e.g., there are no extraneous nucleotides positioned between the TTR promoter and the Factor VIII variant gene.

In some embodiments, the polynucleotide encoding the Factor VIII variant within the AAV gene therapy vector is operatively linked to a polyadenylation signal, e.g., as illustrated in the examples constructs in FIG. 11. In one embodiment, the synthetic polyadenylation signal has a nucleic acid sequence that is at least 90%, 95%, 97%, or 100% identical to the synthetic Poly-A signal shown in FIG. 4 (SEQ ID NO:8).

As reported in Example 6, because of the large size of the Factor VIII variant constructs described herein, a small reduction in the number of nucleotides in a Factor VIII polynucleotide that is part of an AAV gene therapy vector can significantly increase the Factor VIII biopotency of the vector. Accordingly, in some embodiments, the polyadenylation signal is directly attached to the 3' end of the coding sequence of the Factor VIII variant polypeptide, including one or more stop codons that are positioned at the end of the coding sequence. E.g., there are no extraneous nucleotides positioned between the Factor VIII variant gene and the polyadenylation sequence.

Internal terminal repeats are required cis-regulatory elements for AAV-based recombinant vectors. Accordingly, the Factor VIII variant encoding polynucleotides used in the AAV gene therapy vectors described herein include 5' and 3' ITR sequences. In some embodiments, the 5' ITR has high sequence identity (e.g., at least 90%, 95%, 96%, 97%, 98%, 99%, or 100% identical) to the AAV2 5' ITR shown in FIG. 4 (SEQ ID NO:4). In some embodiments, the 3' ITR has high sequence identity (e.g., at least 90%, 95%, 96%, 97%, 98%, 99%, or 100% identical) to the AAV2 3' ITR shown in FIG. 4 (SEQ ID NO:9).

As reported in Example 6, because of the large size of the Factor VIII variant constructs described herein, a small reduction in the number of nucleotides in a Factor VIII polynucleotide that is part of an AAV gene therapy vector can significantly increase the Factor VIII biopotency of the vector. Accordingly, in some embodiments, the 5' ITR is directly attached to the 5' end of the liver-specific element (e.g., one or more CRM8 elements), such that no extraneous nucleotides are positioned between the 5' ITR sequence and the liver-specific element. Similarly, in some embodiments, the 3' ITR is directly attached to the 3' end of the polyadenylation signal, such that no extraneous nucleotides are positioned between the polyadenylation signal and the 3' ITR sequence.

In a specific embodiment, as exemplified in FIG. 11, a polynucleotide included within an AAV gene therapy vector provided herein includes, in a 5' to 3' orientation, a 5' ITR sequence (e.g., having high sequence identity to SEQ ID NO:4), one or two CRM elements having high sequence identity to SEQ ID NO:5, an hTTR promoter element having high sequence identity to SEQ ID NO:6, a minimal Kozak consensus sequence having high sequence identity to SEQ ID NO:7, a Factor VIII variant polynucleotide having high sequence identity to SEQ ID NO:1, a polyadenylation sequence (e.g., having high sequence identity to SEQ ID NO: 8), and a 3' AAV ITR sequence (e.g., having high sequence identity to SEQ ID NO:9). In some embodiments, the described polynucleotide has high sequence identity (e.g., at least 90%, 95%, 96%, 97%, 98%, 99%, 99.5%, 99.9%, or 100% identity) to the CS12-CRM8.2-Vr vector shown in FIG. 3 (SEQ ID NO:3).

The AAV gene therapy vectors described herein are used with AAV capsid proteins that encapsulate the polynucleotide encoding the Factor VIII variant polypeptide, as described herein. That is, the delivery of the viral vector that will produce the Factor VIII is done by using a viral particle including the "shell" of capsid proteins that encapsulate the viral vector.

The serotype of an AAV vector is typically defined by the capsid proteins used. Several AAV serotypes have been characterized, including AAV1, AAV2, AAV3, AAV4, AAV5, AAV6, AAV7, AAV8, and AAV9. Generally, any AAV serotype may be used for the Factor VIII gene therapy constructs described herein. However, the serotypes have different tropisms, e.g., they preferentially infect different tissues. In one embodiment, because Factor VIII is produced primarily in the liver, an AAV serotype for the disclosed gene therapy constructs is selected based on a liver tropism, found in at least serotypes AAV7, AAV8, and AAV9. Accordingly, in one embodiment, a Factor VIII gene therapy construct is an AAV7 serotype vector. In another embodiment, a Factor VIII gene therapy construct is an AAV8 serotype vector. In yet another embodiment, a Factor VIII gene therapy construct is an AAV9 serotype vector.

In some embodiments, plasmid polynucleotides that incorporate a codon-altered Factor VIII gene therapy genomes are also provided. The plasmids are useful for the production of the final AAV particles (e.g., AAV virions carrying the polynucleotide encoding the variant Factor VIII polypeptide), e.g., when introduced into a mammalian cell competent for recombinant AAV production (e.g., a cell harboring nucleic acids encoding AAV rep and cap genes, as well as helper genes (e.g., adenovirus genes) for AAV production. In some embodiments, the plasmids include regulatory elements that allow for replication of the plasmid (e.g., to scale-up the plasmid) in a host cell (e.g., a prokaryotic host cell, such as a bacterium, or a eukaryotic host cell, such as a yeast).

For instance, the sequence of an example plasmid carrying a codon-altered Factor VIII gene therapy genome is shown in FIG. 5 (CS12-CRM8.2-Vrp; SEQ ID NO:10), in accordance with an embodiment of the disclosure. The CS12-CRM8.2-Vrp plasmid includes the CS12-CRM8.2-Vr Factor VIII gene therapy genome (shown as SEQ ID NO:3, in FIG. 3), and plasmid backbone (shown as SEQ ID NO:54, in FIG. 18). The genetic elements of the CS12-CRM8.2-Vr Factor VIII gene therapy genome are shown in FIG. 4, as described above. The plasmid backbone of the CS12-CRM8.2-Vrp plasmid includes a pNMB1 replicon (shown as SEQ ID NO:55 in FIG. 19; Bolivar F., Life Sci., 25(10): 807-17 (1979)) that facilitates replication of the plasmid in a bacterial host cell, and a Bla(ApR) ampicillin resistance gene (shown as SEQ ID NO:56 in FIG. 19; Sutcliffe, P.N.A.S. U.S.A, 75(8):3737-41 (1978)) that facilitates selection of bacterial host cells transformed by the plasmid. The location of each element in the CS12-CRM8.2-Vrp plasmid is shown in Table 1 below.

TABLE 1

Elements present in the CS12-CRM8.2-Vrp plasmid.

| Name of element | Nucleotide position | SEQ ID NO: |
|---|---|---|
| AAV2 5'-ITR | 1-145 | SEQ ID NO: 4 |
| CRM8 | 146-217; 219-290 | SEQ ID NO: 5 |
| Human TTR promoter | 291-523 | SEQ ID NO: 6 |
| Kozak sequence | 524-528 | SEQ ID NO: 7 |
| FVIII-BDD coding sequence with X5 and NG5 | 529-4923 | SEQ ID NO: 1 |
| ATG start codon | 529-531 | |
| TGA stop codons | 4921-4923; 4924-4926 | |
| X5 variant (I86V; A108S; G132K; M147T; L152P) | 841-843; 907-909; 979-981; 1024-1026; 1039-1041 | |
| NG5 sequence | 2821-2841 | SEQ ID NO: 16 |
| Synthetic polyA | 4927-4975 | SEQ ID NO: 8 |
| AAV2 3'-ITR | 4976-5120 | SEQ ID NO: 9 |
| Plasmid backbone | 5121-7794 | SEQ ID NO: 54 |
| Rep (pMB1) | 5541-6155 | SEQ ID NO: 55 |
| Bla(ApR) | 6315-7175 | SEQ ID NO: 56 |

In one embodiment, a plasmid incorporating a Factor VIII variant gene therapy genome has high sequence identity to the CS12-CRM8.2-Vrp plasmid shown in FIG. 5 (SEQ ID NO:10). In some embodiments, the described polynucleotide has high sequence identity (e.g., at least 90%, 95%, 96%, 97%, 98%, 99%, 99.5%, 99.9%, or 100% identity) to the CS12-CRM8.2-Vrp plasmid shown in FIG. 5 (SEQ ID NO:10). In some embodiments, the described polypeptide includes a Factor VIII-BDD coding sequence, e.g., a sequence having at least 95%, 96%, 97%, 98%, 99%, 99.5%, 99.9%, or 100% identity to a Factor VIII-BDD coding sequence disclosed herein, and high sequence identity to the remaining portion of the CS12-CRM8.2-Vrp plasmid shown in FIG. 5, e.g., at least 80%, 85%, 90%, 95%, 96%, 97%, 98%, 99%, 99.5%, 99.9%, or 100% identity to nucleotides 1-528 and 4924-7794 of SEQ ID NO:10. In some embodiments, the described polynucleotide is a plasmid that comprises some or all of the elements shown in Table 1. In some embodiments, one or more of the elements shown in Table 1 are replaced by a comparable element.

Production of AAV Vectors

The codon-altered Factor VIII polynucleotides and viral vectors described herein are produced according to conventional methods for nucleic acid amplification and vector production. Several platforms have been developed for large-scale production of recombinant AAV vectors. A first platform is based on introduction of a plasmid containing the sequence for the desired viral genome into a mammalian cell containing polynucleotides encoding AAV rep and cap genes, as well as viral replication helper genes. For review, see, Kotin R. M., Hum. Mol. Genet., 20(R1):R2-6 (2011); Penaud-Budloo, M. et al., Mol Ther Methods Clin Dev., 8(8):166-80 (2018); and Aponte-Ubillus J J et al., Appl Microbiol Biotechnol., 102(3):1045-54 (2018), the contents of which are expressly incorporated herein by reference, in its entirety, for all purposes. A second platform is based on construction of a stable mammalian cell line having the desired viral genome integrated in the mammalian cell genome, e.g., by co-infection of a mammalian cell with wild type adenovirus and recombinant adenovirus harboring the sequence for the desired viral genome. For review, see, Penaud-Budloo, M. et al., Mol Ther Methods Clin Dev., 8(8):166-80 (2018), the content of which is expressly incorporated herein by reference, in its entirety, for all purposes. A third platform is based on co-infection of a mammalian cell with a first recombinant HSV harboring the sequence for the desired viral genome and a second recombinant HSV encoding AAV rep and cap genes. For review, see, Penaud-Budloo, M. et al., Mol Ther Methods Clin Dev., 8(8):166-80 (2018); and Aponte-Ubillus J J et al., Appl Microbiol Biotechnol., 102(3):1045-54 (2018), the contents of which are expressly incorporated herein by reference, in its entirety, for all purposes. A fourth platform is based on co-infection of insect cells with a first recombinant baculovirus harboring the sequence for the desired viral genome and a second recombinant baculovirus encoding AAV rep and cap genes. For review, see, Penaud-Budloo, M. et al., Mol Ther Methods Clin Dev., 8(8):166-80 (2018); and Aponte-Ubillus J J et al., Appl Microbiol Biotechnol., 102 (3):1045-54 (2018), the contents of which are expressly incorporated herein by reference, in its entirety, for all purposes. A fifth platform is based on based on introduction of a plasmid containing the sequence for the desired viral genome into a yeast cell containing polynucleotides encoding AAV rep and cap genes, as well as viral replication helper genes. For review, see, Aponte-Ubillus J J et al., Appl Microbiol Biotechnol., 102(3):1045-54 (2018), the content of which is expressly incorporated herein by reference, in its entirety, for all purposes.

V. Methods of Treating Hemophilia A

In some embodiments, the nucleic acid compositions (e.g., codon-altered polynucleotides encoding a Factor VIII variant) and gene therapy vectors (e.g., AAV particles containing a codon-altered polynucleotide encoding a Factor VIII variant) described herein are administered to a patient with hemophilia A for the treatment of hemophilia A, in accordance with known administrative methods. Methods for administering gene therapy vectors are well known in the art. These include, without limitation, intravenous administration, intramuscular injection, interstitial injection, and intra-hepatic administration (e.g., intra-hepatic artery or vein). For example, see Chuah M K et al., Hum Gene Ther., 23(6):557-65 (2012); Chuah M K et al., J Thromb Haemost., 10(8):1566-69 (2012); Chuah M K et al., J Thromb Haemost. 11 Suppl 1:99-110 (2013); VandenDriessche et al., Hum Gene Ther. 23(1):4-6 (2012); High K A, Blood, 120(23):4482-87 (2012); Matrai et al., Mol Ther., 18(3): 477-90 (2010); and Matrai et al., Curr Opin Hematol., 17(5):387-92 (2010), the content of each of which is hereby incorporated by reference herein, for review.

Accordingly, the disclosure provides methods for treating a Factor VIII deficiency (e.g., hemophilia A). In some embodiments, the methods include administering to a patient in need thereof a nucleic acid composition (e.g., a codon-altered Factor VIII polynucleotide construct and/or recombinant AAV vector), as described herein. In some embodiments, the nuclic acid composition includes a codon-altered polynucleotide encoding a Factor VIII variant polypeptide, e.g., having high nucleic acid sequence identity (e.g., at least 95%, 96%, 97%, 98%, 99%, 99.5%, 99.9%, or 100%) to CS12-FL-NA (SEQ ID NO:1). As described herein, in some embodiments, the codon-altered polynucleotide encoding the Factor VIII variant polypeptide is operably linked to a promoter (e.g., a human TTR promoter, as described herein) and one or more liver-specific regulatory elements (e.g., one or two CRM8 elements, as described herein).

In some embodiments, the nucleic acid composition is part of a mammalian gene therapy vector. In a specific embodiment, the mammalian gene therapy vector is a viral vector, e.g., a lentivirus, retrovirus, adeno virus, or adeno-associated virus vector.

In one embodiment, the gene therapy vector is an adeno-associated virus (AAV) particle harboring a viral vector encoding the codon-altered Factor VIII variant coding sequence. Generally, the viral vector includes inverted terminal repeats (ITR) at each termini, one or more expression regulatory elements (e.g., a promoter (e.g., a human TTR promoter, as described herein) and one or more liver-specific regulatory elements (e.g., one or two CRM8 elements, as described herein)), a codon-altered Factor VIII coding sequence, and a poly-A signal sequence.

Assessing Therapeutic Efficacy

The therapeutic efficacy of a hemophilia A treatment can be evaluated, for example, by measuring the Factor VIII-dependent coagulation potential of blood from a subject being treated. Metrics for assessing coagulation potential include, without limitation, in vitro activated partial thromboplastin time assay (APPT), Factor IX chromogenic activity assays, blood clotting times, and Factor VIII antigen levels (e.g., using a Factor VIII-specific ELISA). It should be noted that a therapeutic dose need not result in wild-type levels of Factor VIII in a patient; rather, sufficient expression to decrease symptoms in a meaningful or measurable way is considered therapeutic for the purposes of the disclosure.

According to the National Hemophilia Foundation, a subject is classified as having mild hemophilia A when their blood plasma contains between 6% and 49% of the Factor VIII activity of normal human blood plasma. Subjects with mild hemophilia A typically experience bleeding only after serious injury, trauma or surgery. In many cases, mild hemophilia is not diagnosed until an injury, surgery or tooth extraction results in prolonged bleeding. The first episode may not occur until adulthood. Women with mild hemophilia often experience menorrhagia, heavy menstrual periods, and can hemorrhage after childbirth.

According to the National Hemophilia Foundation, a subject is classified as having moderate hemophilia A when their blood plasma contains between 1% and 5% of the Factor VIII activity of normal human blood plasma. Subjects with moderate hemophilia A tend to have bleeding episodes after injuries. Bleeds that occur without obvious cause are called spontaneous bleeding episodes.

According to the National Hemophilia Foundation, a subject is classified as having severe hemophilia A when their blood plasma contains less than 1% of the Factor VIII activity of normal human blood plasma. Subjects with severe hemophilia A experience bleeding following an injury and may have frequent spontaneous bleeding episodes, often into their joints and muscles.

In some embodiments, normal human blood plasma is defined as containing 1 IU of Factor VIII activity per mL. Thus, in some embodiments, blood plasma from a subject classified with mild hemophilia A contains between 0.06 and 0.49 IU of Factor VIII activity per mL. In some embodiments, blood plasma from a subject classified with moderate hemophilia A contains between 0.01 and 0.05 IU of Factor VIII activity per mL. In some embodiments, blood plasma from a subject classified with severe hemophilia A contains between 0.01 and 0.05 IU of Factor VIII activity per mL.

In some embodiments, a therapy is therapeutically effective when it lessens the severity of a symptom of hemophilia A, e.g., by raising the average level of Factor VIII activity in the subject's blood. Accordingly, in some embodiments, hemophilia A therapy is therapeutically effective when it raises the average level of Factor VIII activity in the subject's blood/plasma. In some embodiments, a therapeutically affective treatment raises the average level of Factor VIII activity in the subject's blood/plasma by at least 0.5%, 1%, 2%, 3%, 4%, 5%, 6%, 7%, 8%, 9%, 10%, 15%, 20%, 25%, 30%, 35%, 40%, 45%, 50%, or more.

In some embodiments, a therapeutically effective treatment raises the average level of Factor VIII activity in the subject's blood such that the subject is classified as having a less severe form of hemophilia A. For example, in one embodiment, a subject originally classified with severe hemophilia A is reclassified with moderate hemophilia A or mild hemophilia A after undergoing a therapeutically effective treatment. In another embodiment, a subject originally classified with moderate hemophilia A is reclassified with mild hemophilia A after undergoing a therapeutically effective treatment. In another embodiment, a subject originally classified with mild hemophilia A is reclassified as not having hemophilia A after undergoing a therapeutically effective treatment.

Formulations

Compositions for use in treatment of hemophilia A are provided herein. Such compositions contain a therapeutically effective amount of a nucleic acid composition, e.g., an AAV gene therapy vector including a codon-altered polynucleotide encoding for Factor VIII, as described herein. Therapeutically effective amounts of the codon-altered VIII polynucleotide (e.g., an AAV gene therapy vector including the codon-altered Factor VIII coding sequence) are mixed with a suitable pharmaceutical carrier or vehicle for, e.g., systemic administration. Final formulation of the codon-altered Factor VIII polynucleotides disclosed herein will be within the abilities of those skilled in the art.

Dosages

The nucleic acid compositions of the invention are administered to patients in need thereof. The amount or dose of the therapeutic gene therapy agent administered depends on factors such as the particular codon-altered VIII polynucleotide construct, the delivery vector used, the severity of the disease, and the general characteristics of the subject. The exact dose will depend on the purpose of the treatment, and will be ascertainable by one skilled in the art using known techniques (see, e.g., Lieberman, Pharmaceutical Dosage Forms (vols. 1 3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). It is within the abilities of the skilled physician to determine a particular dosage and dosing regimen for treatment of a particular subject.

VI. EXAMPLES

Example 1—Improvement of a Single-Stranded AAV8 Vector Construct Expressing FVIII by Addition of N-Glycosylation Linker Sequences To address whether additional N-glycosylation sites within the SQ sequence of BDD-FVIII increases FVIII protein expression, a set of short peptide sequences containing putative N-linked glycosylation sites were designed. Previously, McIntosh et al. (Blood 121(17):3335-44 (2013)) showed that the concept of N-glycosylation with 6 potential sites ("V3 peptide") resulted in enhanced FVIII expression levels in the plasma of mice. Interestingly, in silico prediction of the "V3 peptide" identified two out of 6 sites to be potentially N-glycosylated in vivo.

12 different linker sequences, shown as NG1-NG21 (SEQ ID NOs: 11, 13, 15, 17, 19, 21, 23, 25, 27, 29, 31, and 33) in FIGS. 8A-8B, were designed within the context of a codon-optimized BDD-FVIII "CS01" sequence (see, WO 2017/083762, the contents of which are hereby incorporated herein by reference) by applying the program NetNGlyc-Database (Steentoft et al., H. EMBO J, 32(10):1478-88, 2013), with the goal of generating short sequences containing multiple N-glycosylation sites. The NetNGly platform combines nine neural networks analyzing human protein sequences for their N-glycosylation pattern. Based on the NetNGly database, the designed peptides were analyzed for the likelihood to transfer N-glycosylation as post-translational modification, as described in Steentoft et al., H. EMBO J, 32(10):1478-88, (2013), the contents of which are hereby incorporated by reference herein. Of the 12 novel alternative peptides, four promising NG linkers with predicted low immunogenicity (as explained below) were inserted into the 14 amino acid-sized SQ sequence (SFSQN—novel peptide—PPVLKRHQR) of a codon-optimized BDD-FVIII sequence termed "CS04" (SEQ ID NO:10).

Figure 10:
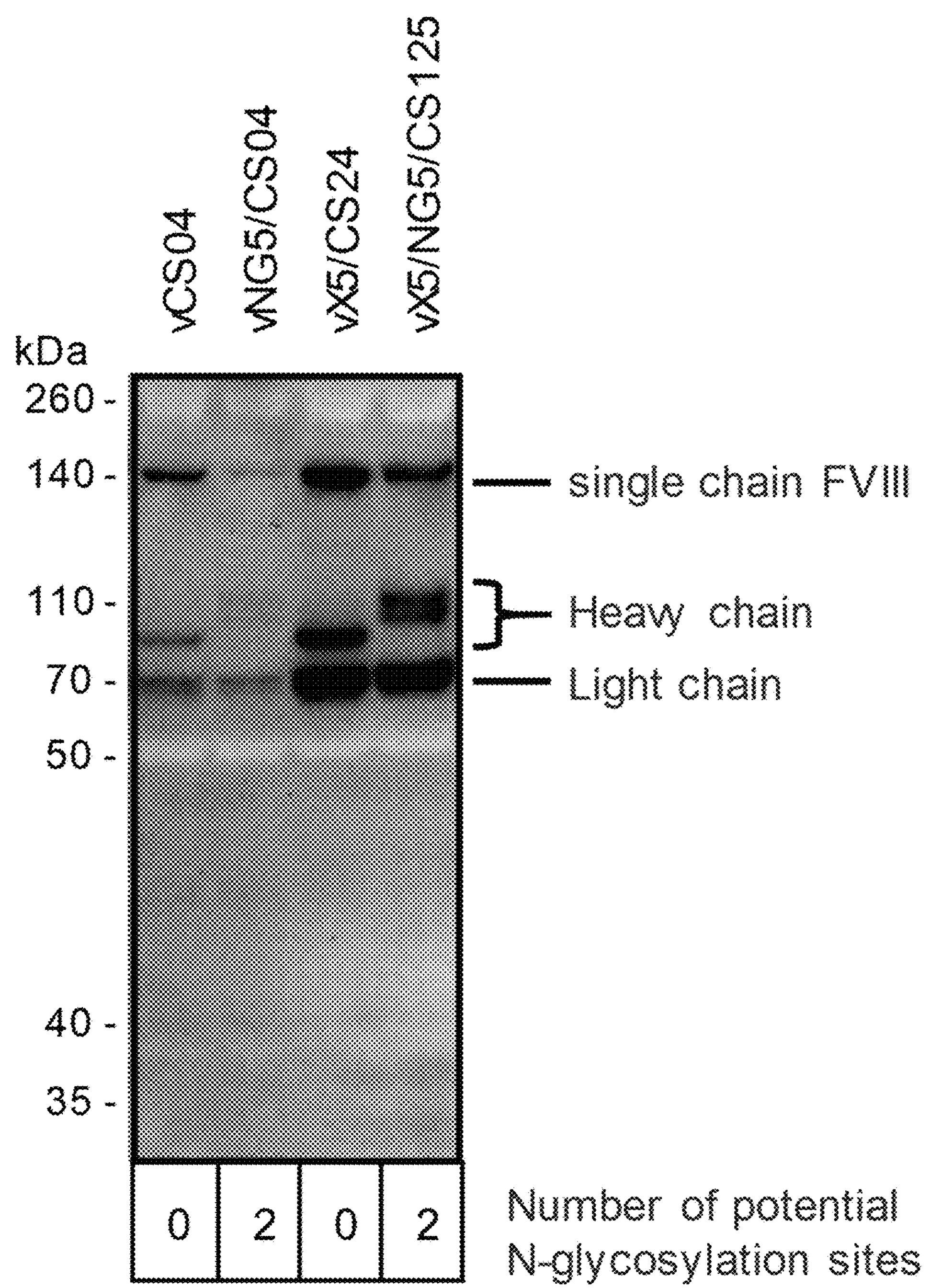
FIG. 10 shows western blot analysis of Factor VIII variants, with (vNG4/CS04, vNG5/CS04, and vNG16/CS04) and without (vCS04 with SQ) glycosylation peptides engineered into the SQ linker, expressed in HepG2 cells following infection of an AAV8 gene therapy vector.

Post-translational modification of the predicted N-glycosylation sites was confirmed experimentally for three vectors including vNG4/CS04, vNG5/CS04, and vNG16/CS04, by transfecting human hepatic Huh-7 cells and detecting modified BDD-FVIII by anti-FVIII Western blot analyses (FIG. 9). In comparison to BDD-FVIII containing the SQ sequence only, larger-sized heavy chains of the modified versions of FVIII were detected by gel electrophoresis, indicating the presence of novel N-glycosylation sites. In addition, AAV8 infection of the human liver cell line HepG2 confirmed the N-glycosylation as shown exemplary for the expression vector vNG5/CS04 and the highly secreting X5 variant vX5/NG5/CS125 (FIG. 10; vX5/NG5/CS125 will be described in Examples 3 and 5).

The focus for the linker sequence design was to generate short peptide sequences (7-17 amino acid residues) accompanied by low risk of immunogenicity. For this, in silico immunogenicity profiling Epibase™ (Lonza) was applied (HLA binding). Epibase™'s epitope prediction method comprises a structural and a statistical layer for the prediction of immunogenicity. The structural part estimates the binding affinity based on the Pepscope technology, as described in Desmet et al., Proteins. 58(1):53-69 (2005), the contents of which are hereby incorporated herein by reference. The statistical part extracts information from peptide sequences and their experimental binding affinities. Based on the critical epitope counts, the affected HLA class II allotypes (Krischmann et al., J Immunol. 15; 155(12):5655-62 (1995); Verreck et al., Int Immunol. 8(3):397-404 (1996), the contents of which are hereby incorporated herein by reference) and DRB1 (Laupeze et al., Hum Immunol. 60(7): 591-7 (1999), the content of which is hereby incorporated herein by reference) risk score were used to estimate the immunogenic risk of the proteins. Based on this scoring system, the immunogenic risk of peptide NG16 is moderate, that of NG4 and NG10 is low and that of NG5 is even lower that the unmodified SQ sequence of BDD-FVIII (Table 2).

TABLE 2

FVIII activity two weeks after AAV treatment in vivo.

| | Linker | | | | FVIII knock-out mice | | "line E" mice | |
|---|---|---|---|---|---|---|---|---|
| AAV construct | ID | Number of amino acid residues | Number of predicted N-glycosylation sites | Epibase Predicted immune-genicity | FVIII activity [IU/mL] | Fold increase vs Orth04 | FVIII activity [IU/mL] | Fold increase vs Orth04 |
| vCS04 | — | 0 | 0 | low | 1.7 ± 0.5 | 1.0 | 1.4 ± 0.6 | 1.0 |
| vNG4/CS04 | NG4 | 11 | 3 | low | 3.1 ± 0.6 | 1.8 | n.d. | n.d. |
| vNG5/CS04 | NG5 | 7 | 2 | very low | 3.8 ± 0.8 | 2.3 | 4.0 ± 2.8 | 3.0 |
| vNG10/CS04 | NG10 | 17 | 2 | low | 4.1 ± 0.5 | 2.4 | n.d. | n.d. |
| vNG16/CS04 | NG16 | 9 | 2 | moderate | 2.5 ± 0.8 | 1.4 | n.d. | n.d. |

Further, vectors vNG4/CS04, vNG5/CS04, vNG10/CS04 and vNG16/CS04 were analyzed in exon 16 FVIII knock-out mouse model generated in the laboratory of Haig Kazazian at the University of Pennsylvania (Table 2). Two weeks post AAV8 infection, FVIII expression levels were determined by chromogenic activity of mouse plasma samples. Two weeks post AAV8 infection at a dose of $4.0\times10^{12}$, FVIII expression levels were 1.4 to 2.4-fold higher than the peptide-free vCS04 construct. Overall, construct vNG5/CS04 displayed the most favorable features, including the high FVIII expression levels (3.8 IU/mL), the lowest immunogenic risk, and the shortest peptide in size (7 amino acid residues). Construct vNG5/CS04 was further tested in another FVIII mouse model, the "line E" model, which is immunologically tolerant to human FVIII (described in Reipert et al., Haemophilia. 16 (Suppl 5):47-53 (2010) and van Helden et al., Blood 118(13):3698-707 (2011), the contents of which are hereby expressly incorporated herein by reference). In this independent mouse model, increased FVIII expression of vNG5/CS04 was confirmed and assessed to be 3-fold higher than vCS04.

Taken together, an improved vector termed vNG5/CS04 containing a short novel N-glycosylation peptide sequence with a very low immunogenic risk and enhanced levels of FVIII expression in vivo was developed.

Example 2—Improvement of a Single-Stranded AAV8 Vector Construct Expressing FVIII by Promoter/Enhancer Replacement The promoter cassette of the initial FVIII-expressing AAV8-based single-stranded vector construct termed vCS04 contains a core promoter and enhancer sequence derived from the liver-specific murine transthyretin (TTR) gene (Yan et al., EMBO J, 9:869-78 (1990), the content of which is hereby incorporated by reference herein), see FIG. 11. This liver-specific mTTR promoter/enhancer cassette was modified two-fold, firstly the murine core (basal) promoter sequence was fully replaced by the corresponding human sequence. Secondly, the murine enhancer sequence was replaced by the recently described liver-specific cis-regulatory module CRM8 (Nair et al., Blood, 123:3195-99 (2014) and Chuah et al., Mol Ther, 22:1605-13 (2014), the contents of which are hereby incorporated herein by reference). One or two CRM8 elements were inserted upstream of the human TTR core (basal) promoter, resulting in vector constructs vCS115 and vCS116, respectively (FIG. 11).

The strength of the novel promoter cassette was assessed by in vitro and in vivo analyses, in a human liver-derived HepG2 cell line and in "line E" mice at a dose of 4.0E+12 vg/kg. In vitro, the constructs with one CRM8 element (vCS115) and two CRM8 elements (vCS116) resulted in 2.2- and 3.7-fold higher biopotency units, respectively, in comparison to the reference (vCS04) (FIG. 12). In vivo, the CRM8/hTTR promoter cassette performed comparable to the mTTR promoter/enhancer (FIG. 12).

The CRM8-related augmenting effect on FVIII expression was further evaluated in triple sets of constructs, in which the described promoter cassettes including mTTR promoter/enhancer, 1×CRM8/hTTR, and 2×CRM8/hTTR were combined with novel modifications of BDD-FVIII (see below, Examples 3-5). Overall, the in vitro data reveal an increase in biopotency units based on the presence of one and two CRM8 elements by directly comparing (1) vNG5/CS04 with vNG5/CS117 (2.5 fold higher) and vNG5/CS118 (4.0-fold higher), (2) vX5/CS24 with vX5/CS101 (1.8-fold higher) and vX5/CS105 (5.3-fold higher) and (3) vX5/NG5/CS125 with vX5/NG5/CS119 (4.4-fold higher) and vX5/NG5/CS120 (6.2-fold higher). No CRM8-dependent effect on FVIII levels was observed in vivo. Nevertheless, the in vivo data clearly show that both the novel 1×CRM8/hTTR and the 2×CRM8/hTTR promotor cassette perform equally well in the mouse model compared to the mTTR promoter/enhancer.

Example 3—Improvement of a Single-Stranded AAV8 Vector Construct Expressing FVIII by Introduction of the "NG5" Variant Based on the data shown in Example 1, the N-glycosylation linker NG5 in construct vNG5/CS04 was selected to be combined with the novel human liver-specific promoters 1×CRM8/hTTR and 2×CRM8/hTTR, resulting in constructs vNG5/CS117 and vNG5/CS118 (FIG. 11). The vNG5/CS04 construct contains the mTTR promoter/enhancer cassette (FIG. 11). The in vivo biopotency levels of vNG5/CS04 were 1.9-fold higher than vCS04, attributing the positive effect on the NG5 linker sequence (FIG. 12). In vitro, an increase in biopotency was observed for the CRM8 element(s)-containing vectors vNG5/CS117 and vNG5/CS118. In vivo, expression levels of vNG5/CS117 and vNG5/CS118 were similar to vNG5/CS04) (FIG. 12).

Example 4—Improvement of a Single-Stranded AAV8 Vector Construct Expressing FVIII by Introduction of the "X5" Variant In order to further improve the FVIII-expressing vectors, the X5 variant (described as mutation 'm2' in WO 2017/083762, the content of which is hereby incorporated herein by reference) was introduced into BDD-FVIII. The X5 variant contains five porcine FVIII amino acid residues within the A1 domain of the heavy chain that confer efficient secretion to human FVIII (Cao et al., 2014, ASGCT abstract #460; details of variants disclosed in oral presentation). Specifically, the X5 variant of BDD-FVIII was combined with the mTTR promoter/enhancer, resulting in vX5/CS24, and with one or two CRM8 element(s) plus hTTR promoter, resulting in constructs vX5/CS101 and vX5/CS105 (FIG. 11). The three novel constructs were analyzed in vitro in a liver-derived HepG2 cell line and in vivo in "line E2" mice, a transgenic FVIII knock-out mouse line which expresses minimal amounts of human FVIII cDNA leading to immunological tolerance to human FVIII (van Helden P M, et al., Blood 118(13):3698-707 (2011), the content of which is incorporated by reference herein, in its entirety, for all purposes), and compared to the reference construct vCS04. In vivo, vX5/CS24, vX5/CS101, and vX5/CS105 resulted in enhanced levels of FVIII activity by a factor of 2.5-3.1 (FIG. 12). In vitro, the increase in biopotency ranged between 4.0 and 21.2. The in vitro test system revealed a 4.0-fold increase stemming from the X5 variant (construct vX5/CS24), and was further increased by a factor of 7.3 and 21.2 by the constructs containing X5 and one or two copies of the CRM8 element (constructs vX5/CS101 and vX5/CS105, respectively).

Example 5—Improvement of a Single-Stranded AAV8 Vector Construct Expressing FVIII by Introducing Both the "X5" and the "NG5" Variant In a further set of vectors, the N-glycosylation linker NG5 (Example 3) and the X5 variant (Example 4) were introduced into BDD-FVIII in parallel, and additionally combined with three different promoters, including the mTTR promoter/enhancer, lx CRM8/hTTR, and 2×CRM8/hTTR, resulting in constructs vX5/NG5/CS125, vX5/NG5/CS119 and vX5/NG5/CS120, respectively (FIG. 11). In comparison to vCS04, in vivo and in vitro biopotencies of vX5/NG5/CS125, vX5/NG5/CS119, and vX5/NG5/CS120 were elevated by a factor of 3.6-5.5 and 3.2-19.8, respectively. The introduction of the two novel modifications X5 and NG5 reveal further increased expression, in vivo, as shown for the three series of constructs each having a common promoter. For example, for the series with the 2×CRM8/hTTR promoter (constructs vCS116, vNG5/CS118, vX5/CS105, and vX5/NG5/CS120), the presence of NG5 alone raises the FVIII expression level from 1.9 to 2.9 IU/mL, the presence of X5 alone raises the FVIII expression from 1.9 to 5.1 IU/mL, and the presence of both X5 and NG5 raises the FVIII expression from 1.9 to 11.4 IU/mL.

Taken together, construct vX5/NG5/CS120 carrying the novel 2×CRM8/hTTR promoter cassette and additionally a codon-optimized BDD-FVIII "CS04" nucleotide sequence with two modifications, the X5 variant and the NG5 sequence, was determined to be the construct with highest in vitro and in vivo biopotencies.

Example 6—Nucleotide Reduction of a Single-Stranded AAV8 Vector Construct

In order to reduce the vector size of the slightly oversized vector construct vX5/NG5/CS120 which should result in more efficient packaging, all non-function DNA sequences within the flanking ITR's were deleted. This resulted in the reduction of a total of 71 nucleotides, from a 5191 to a 5120 nucleotide-sized expression cassette. The deletions included 19 nucleotides between the 5'-ITR and the CRM8 sequence, 9 nucleotides between the human TTR promoter and the Kozak sequence, 27 nucleotides between the BDD-FVIII coding sequence and the synthetic polyadenylation site, and 16 nucleotides between the synthetic polyadenylation site and the 3'-ITR sequence. The size-reduced expression cassette, termed vX5/NG5/CS12, consists of a promoter with two CRM8 elements and the core human TTR promoter sequence, the BDD-FVIII sequence including the X5 variant as well as the NG5 sequence and a synthetic polyadenylation site and is flanked by two AAV2-based inverted terminal repeats. Construct vX5/NG5/CS12 is schematically shown in FIG. 11.

Figure 13:
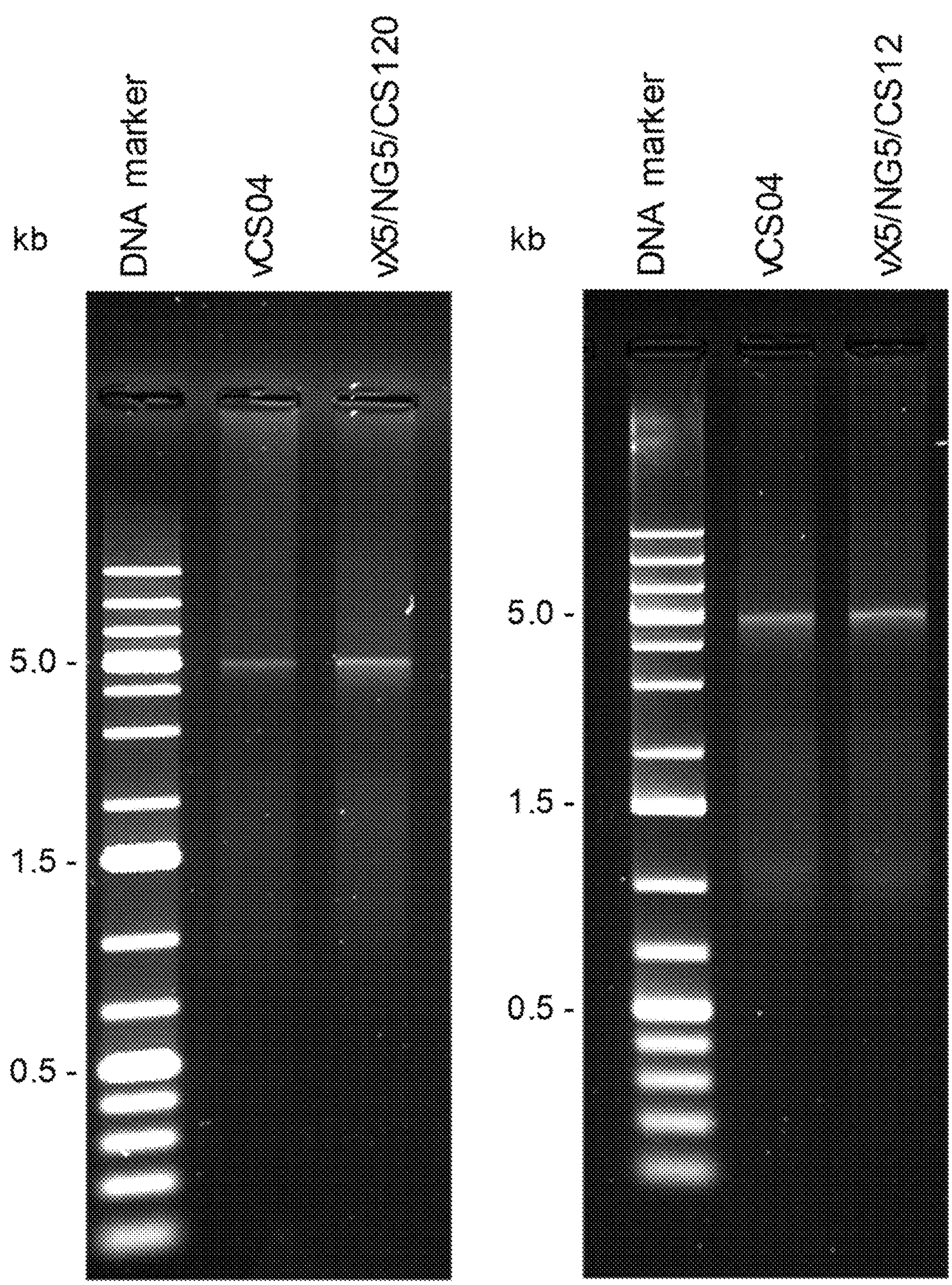
FIG. 13 shows agarose gel electrophoretic analysis of the vCS04, vX5/NG5/CS120, and vX5/NG5/CS12 gene therapy vectors encoding a Factor VIII variant in accordance with some embodiments.

Vector genome integrity of the AAV vector genome preparations vCS04, vX5/NG5/CS120 and vX5/NG5/CS12 was addressed by agarose gel electrophoresis. The results shown in FIG. 13 demonstrate that the vCS04, vX5/NG5/CS120 and vX5/NG5/CS12 viral vectors have a similar-sized genome, indicated by a distinct band of approximately 5 kb. Despite a calculated vector size of approx. 5.2 kb, the genome is a homogenous band confirming correct packaging of the marginally oversized genome (relative to an AAV wild-type genome of 4.7 kb). The shorter vX5/NG5/CS12 variant is preferred.

A set of AAV8-based viral vectors including vCS04, vX5/NG5/CS120, and vX5/NG5/CS12 were administered to FVIII F17 knock-in mice at vector doses of $5\times10^{11}$ vg/kg, $1\times10^{12}$ vg/kg, and $4\times10^{12}$ vg/kg and FVIII activity levels were determined at day 14. As shown in FIG. 14, both vX5/NG5/CS12 and vX5/NG5/CS120 resulted in comparable expression levels of approximately 4 IU/mL at the vector dose of $1\times10^{12}$ vg/kg. In contrast to the reference construct vCS04 with very low FVIII expression levels of 0.3 IU/mL at a dose of $1\times10^{12}$ vg/kg, the improved vectors vX5/NG5/CS12 and vX5/NG5/CS120 showed elevated FVIII expression levels by a factor of approximately 14 (FIG. 14). Even at the dose of $5\times10^{11}$ vg/kg expression levels of 1.5 IU/mL of FVIII could be obtained for the vector vX5/NG5/CS12. In accordance to the in vivo data, the in vitro biopotencies of vX5/NG5/CS120 and vX5/NG5/CS12 are strongly elevated approximately by a factor of 17 and 24, respectively, infecting HepG2 cells at equal multiplicity of infection (MOI) (FIG. 14). Thus, because all vectors were administered at the same concentration (multiplicity of infection), the differences in biopotency are due to the variants used and are not size-dependent.

What is claimed is:

1. A nucleic acid composition comprising a Factor VIII polynucleotide encoding a Factor VIII protein, said Factor VIII polynucleotide having the nucleic acid sequence of SEQ ID NO:1.

2. The nucleic acid composition of claim 1, further comprising a promoter operatively linked to the Factor VIII polynucleotide, wherein the promoter polynucleotide has the nucleic acid sequence of SEQ ID NO:6.

3. The nucleic acid composition of claim 2, wherein there are no nucleotides between the promoter and the Factor VIII polynucleotide.

4. The nucleic acid composition of claim 1, further comprising a liver-specific element operatively linked to the Factor VIII polynucleotide, wherein the liver-specific element has a sequence of SEQ ID NO:5.

5. The nucleic acid composition of claim 4, wherein a second liver-specific element is operatively linked to said Factor VIII polynucleotide.

6. The nucleic acid composition of claim 4, further comprising a promoter operatively linked to the Factor VIII polynucleotide, wherein:

the liver-specific element is positioned upstream of the promoter, the promoter is positioned upstream of the Factor VIII polynucleotide, and there are no nucleotides between the liver-specific element and the promoter.

7. The nucleic acid composition of claim 1, having the nucleic acid sequence comprising SEQ ID NO: 3.

8. A mammalian gene therapy vector comprising the nucleic acid composition according to claim 1.

9. The mammalian gene therapy vector of claim 8, wherein the mammalian gene therapy vector is an adeno-associated virus (AAV) vector.

10. The mammalian gene therapy vector of claim 9, wherein the AAV vector is a serotype 8 adeno-associated virus (AAV-8) vector.

11. The mammalian gene therapy vector according to claim 8, wherein the Factor VIII polynucleotide encoding the Factor VIII protein is a single-stranded polynucleotide having the nucleic acid sequence of SEQ ID NO: 1.

12. An adeno-associated virus (AAV) particle comprising capsid proteins encapsulating the nucleic acid composition according to claim 1.

13. The AAV particle of claim 12, wherein the capsid proteins comprise serotype 8 adeno-associated virus (AAV-8) capsid proteins.

14. The AAV particle of claim 12, wherein the Factor VIII polynucleotide encoding the Factor VIII protein is a single-stranded polynucleotide having the nucleic acid sequence of SEQ ID NO:1.

15. A method for producing an adeno-associated virus (AAV) particle comprising introducing the nucleic acid composition according to claim 1 into a eukaryotic host cell: wherein:

the nucleic acid composition comprises a Factor VIII polynucleotide having the nucleic acid sequence of SEQ ID NO:1 flanked by a 5' inverted terminal repeat sequence (5' ITR) and a 3' inverted terminal repeat sequence (3' ITR), and the eukaryotic host cell comprises one or more polynucleotides encoding an AAV rep gene, an AAV cap gene, and viral replication helper genes.

16. The method of claim 15, wherein the nucleic acid composition is a plasmid having the nucleic acid sequence of SEQ ID NO:10.

17. The method of claim 15, wherein the AAV cap gene is a serotype 8 adeno-associated virus (AAV-8) cap gene.

* * * * *